(12) United States Patent
Baker et al.

(10) Patent No.: US 8,273,534 B2
(45) Date of Patent: Sep. 25, 2012

(54) PREDICTORS OF PATIENT RESPONSE TO TREATMENT WITH EGF RECEPTOR INHIBITORS

(75) Inventors: Joffre B. Baker, Montara, CA (US); Drew Watson, Los Altos, CA (US); Tara Maddala, Redwood City, CA (US); Steven Shak, Hillsborough, CA (US); David J. Mauro, Redwood City, CA (US); Shirin K. Ford, Redwood City, CA (US)

(73) Assignees: Genomic Health, Inc., Redwood City, CA (US); Bristol-Myers Squibb Company, Princeton, NJ (US)

( * ) Notice: Subject to any disclaimer, the term of this patent is extended or adjusted under 35 U.S.C. 154(b) by 362 days.

(21) Appl. No.: 12/465,503

(22) Filed: May 13, 2009

(65) Prior Publication Data

US 2009/0298701 A1    Dec. 3, 2009

Related U.S. Application Data

(60) Provisional application No. 61/127,816, filed on May 14, 2008.

(51) Int. Cl.
*C12Q 1/68* (2006.01)
(52) U.S. Cl. .................................. 435/6.11; 435/6.1
(58) Field of Classification Search ................. None
See application file for complete search history.

(56) References Cited

U.S. PATENT DOCUMENTS

| | | |
|---|---|---|
| 2003/0109690 A1 | 6/2003 | Ruben et al. |
| 2004/0157255 A1 | 8/2004 | Agus et al. |
| 2004/0191817 A1 | 9/2004 | Scott et al. |
| 2005/0019785 A1 | 1/2005 | Baker et al. |
| 2005/0164218 A1 | 7/2005 | Agus et al. |
| 2007/0065845 A1 | 3/2007 | Baker et al. |
| 2007/0128636 A1 | 6/2007 | Baker et al. |
| 2009/0305277 A1 | 12/2009 | Baker et al. |
| 2010/0285980 A1 | 11/2010 | Shak et al. |

FOREIGN PATENT DOCUMENTS

| | | |
|---|---|---|
| WO | WO2007019899 | 2/2007 |
| WO | 2007/025044 A2 | 3/2007 |
| WO | WO 2007082099 | 7/2007 |
| WO | WO 2008115419 | 9/2008 |

OTHER PUBLICATIONS

Khambata-Ford et al., "Expression of Epiregulin and Amphiregulin and K-ras Mutation Status Predict Disease Control in Metastatic Colorectal Cancer Patients Treated with Cetuximab," Journal of Clinical Oncology, 2007, 25 (22):3230-3237 and Supplemental Online Tables 1-3.
Nishidate, T. et al., "Genome-Wide Gene-Expression Profiles of Breast-Cancer Cells Purified with Laser Microbeam Microdissection: Identification of Genes Associated with Progression and Metastasis," International Journal of Oncology, 2004, 25: 797-819.
Kobayashi et al., Transcriptional profiling identifies Cyclin D1 as a critical downstream effector of mutant Epidermal Growth Factor Receptor signalling. Cancer Res 2006;66(23):11389-98.
EP 09747492, European Search Report, mail date Aug. 18, 2011, 18pgs.
Tejpar, S. et al., High Amphiregulin and Epiregulin Exression in KRAS Wild Type Colorectal Primaries Predicts Response and Survival Benefit After Treatment with Cetuximab and Irinotecan for Metastatic Disease, 2008 Gastrointestinal Cancers Symposium, Abstract No. 411.

*Primary Examiner* — Young J Kim
(74) *Attorney, Agent, or Firm* — Paula A. Borden; Bozicevic, Field & Francis LLP.

(57) ABSTRACT

The present invention provides methods and compositions to facilitate determining whether an EGFR-expressing cancer in an individual is an EGFR inhibitor-responsive cancer, as well as methods for determining the likelihood that a patient having an EGFR-expressing cancer will exhibit a beneficial response to an EGFR inhibitor therapy. The methods generally involve determining a normalized expression level of a gene product that correlates with EGFR inhibitor responsiveness.

12 Claims, 43 Drawing Sheets

| Gene | Accession Num | Official Symbol | FPrimerSeq | SEQ ID NO | RPrimerSeq | SEQ ID NO | ProbeSeq | SEQ ID NO |
|---|---|---|---|---|---|---|---|---|
| ADAM15 | NM_003815 | ADAM15 | GGCGGGATGTGGTAACAG | 1 | ATTTCTGGGCCTCCGAGT | 110 | TCAGCCACAATCACCAACTCCACA | 219 |
| ADAM17 | NM_003183 | ADAM17 | GAAGTGCCAGGAGGCGATTA | 2 | CGGGCACTCACTGCTATTACC | 111 | TGCTACTTGCAAAGGCGTGTCCTACTGC | 220 |
| AMACR1 | NM_014324 | AMACR | GGACAGTCAGTTTTAGGGTTGC | 3 | GACAGCCCAGAGACCCAC | 112 | CAGTAACTCGGGGCCTGTTTCCC | 221 |
| ANXA1 | NM_000700 | ANXA1 | GCCCCTATCCTACCTTCAATCC | 4 | CCTTTAACCATTATGGCCTTATGC | 113 | TCCTGGGATGTCGCTGCT | 222 |
| ANXA2P2 | M62898 | | CGGACACATCTGGTGACTTC | 5 | AGAGCCATCCTCTGCTCTTC | 114 | TACCCTTTGCCAGGGCAACCATC | 223 |
| AREG | NM_001657 | AREG | TGTGAGTGAAATGCCTTCTAGTAGTGA | 6 | TTGTGGTTCGTTATCATACTCTTCTGA | 115 | CCGTCCTCCGGGAGCCGACTATGA | 224 |
| ATP5E | NM_006886 | ATP5E | CCGCTTTCGCTACAGCAT | 7 | TGGGAGTATCGGATGTAGCTG | 116 | TCCAGCCTGTCTCCAGTAGGCCAC | 225 |
| B-Catenin | NM_001904 | CTNNB1 | GGCTCTTGTGCGTACTGTCCTT | 8 | TCAGATGACGAAGAGCACAGATG | 117 | AGGCTCAGTGATGTCTTCCCTGTCACCAG | 226 |
| Bak | NM_001188 | BAK1 | CCATTCCCACCATTCTACCT | 9 | GGGAACATAGACCCACCAAT | 118 | ACACCCCAGACGTCCTGGCCT | 227 |
| Bclx | NM_001191 | BCL2L1 | CTTTTGTGGAACTCTATGGGAACA | 10 | CAGCGGTTGAAGCGTTCCT | 119 | TTCGGCTCTCGGCTGCTGCA | 228 |
| BGN | NM_001711 | BGN | GAGCTCCGCAAGGATGAC | 11 | CTTGTTGTTCACCAGGACGA | 120 | CAAGGGTCTCCAGCACCTCTACGC | 229 |
| BM039 | NM_018455 | CENPN | GTGAGTCCACTGGGCAC | 12 | CTCCGTTAGGACCTGGCTTA | 121 | CGTCTAAGCACAAGCCGAGCAC | 230 |
| BRAF | NM_004333 | BRAF | CCTTCCGACCAGCAGATGAA | 13 | TTTATATGCACATTGGGAGCTGAT | 122 | CAATTTGGGCAACGAGACCGATCCT | 231 |
| BRCA1 | NM_007295 | BRCA1 | TCAGGGGCTAGAAATCTGT | 14 | CCATTCCAGTTGATCTGTGG | 123 | CTATGGGCCCTTCACCAACATGC | 232 |
| BRCA1 | NM_007295 | BRCA1 | TCAGGGGCTAGAAATCTGT | 15 | CCATTCCAGTTGATCTGTGG | 124 | CTATGGGCCCTTCACCAACATGC | 233 |
| BRK | NM_005975 | PTK6 | GTGCAGGAGAAGGTTCACAA | 16 | GCACACACGATGGAGTAAGG | 125 | AGTGTCTGCGTCCAATACACGCGT | 234 |
| BTC | NM_001729 | BTC | AGGGAGATGCCGCTTCGT | 17 | CTCTCACACCTTGCTCCAATGTA | 126 | CCTTCATCACAGACACAGGAGGGGG | 235 |
| C13orf18 | NM_025113 | C13orf18 | TCCTCAACAGAGGTACACATGG | 18 | ATCCTAGGGCTTGTGTGGC | 127 | ACACCCGATGAGAGTATCCTGGGC | 236 |
| CA9 | NM_001216 | CA9 | ATCCTAGCCCTGGTTTTGG | 19 | CTGCCTTCTCATCTGCACAA | 128 | TTTGCTGTCACCAGCGTCGC | 237 |
| Cad17 | NM_004063 | CDH17 | GAAGGCCAAGAACCAGAGTCA | 20 | TCCCCAGTTAGTTCAAAAGTCACA | 129 | TTATATTCCAGTTTAAGGCCAATCCTC | 238 |
| CCNE1 | NM_001238 | CCNE1 | AAAGAAGATGATGACCGGGTTTAC | 21 | GAGCCTCTGGATGGTGCAAT | 130 | CAAACTCAACGTGCAAGCCTCGGA | 239 |
| CCNE2 | NM_057749 | CCNE2 | ATGCTGTGTGGCTCCTTCCTAACT | 22 | ACCCAAATTGTGATATACAAAAGGTT | 131 | TACCAAGCAACCTACATGTCAAGAAAGCCC | 240 |
| CD134 | NM_003327 | TNFRSF4 | GCCCAGTGCGGGAGAACAG | 23 | AATCACACGCACCTGGAGAAC | 132 | CCAGCTTGATTCTCGTCTCTGCACTTAAGC | 241 |
| CD18 | NM_000211 | ITGB2 | CGTCAGGACCCCACCATGTCT | 24 | GGTTAATTGGTGACATCCTCAAGA | 133 | CGGCGCCGAGACATGGCTTG | 242 |
| CD44E | X55150 | | ATCACCGACAGCACAGACA | 25 | ACCTGTGTTTGGATTTGCAG | 134 | CCCTGCTACCAATATGGACTCCAGTCA | 243 |
| CD44v3 | AJ251595v3 | | CACACAAAACAGAACCAGGACT | 26 | CTGAAGTAGCACTTCCGGATT | 135 | ACCCAGTGGAACCAAGCCATTC | 244 |
| CD44v6 | AJ251595v6 | | CTCATACCAGCCATCCAATG | 27 | TTGGGTTGAAGAAATCAGTCC | 136 | CACCAAGCCAGAGGACAGTTCCT | 245 |
| CDC25B | NM_021873 | CDC25B | AAACGAGCAGTTTGCCATCAG | 28 | GTTGGTGATGTTCCGAAGCA | 137 | CCTCACCGGCATAGACTGGAAGCG | 246 |

FIG. 1

| Gene | Accession Num | Official Symbol | FPrimerSeq | SEQ ID NO | RPrimerSeq | SEQ ID NO | ProbeSeq | SEQ ID NO |
|---|---|---|---|---|---|---|---|---|
| CEACAM6 | NM_002483 | CEACAM6 | CACAGCCTCACTTCTAACCTTCTG | 29 | TTGAATGGGCGTGGATTCAATAG | 138 | ACCCACCCACCACTGCCAAGCTC | 247 |
| CGA | NM_001275 | CGA | CTGAAGGAGCTCCAAGACCT | 30 | CAAAACCGCTGTGTTTCTTC | 139 | TGCTGATGTGCCCTCTCCTTGG | 248 |
| CHN2 | NM_004067 | CHN2 | GATCGCTGAGTGGGGTACTG | 31 | CCTCACCTTCACCCTTGTTC | 140 | CTCATAGACATGCGCCACCTCCAC | 249 |
| CKMT2 | NM_001825 | CKMT2 | CTAACTGGCCGCAATGCT | 32 | AGGTACCCGGTGGTCAGG | 141 | TCTGCTGTTTGCTACCATGGGCAC | 250 |
| CLTC | NM_004859 | CLTC | ACCGTATGGACAGCCACAG | 33 | TGACTACAGAGATCAGCGCTTC | 142 | TCTCACATGCTGTACCCAAAGCCA | 251 |
| cMet | NM_000245 | MET | GACATTTCCAGTCTCCTGCAGTCA | 34 | CTCCGATGCGCACACATTTGT | 143 | TGCCTCTCGCCCCACCCTTTGT | 252 |
| CYP2B6 | NM_000767 | CYP2B6 | ATCCAACGCACACAGTGAAT | 35 | AAAGAAGAGCGAGAGCGTGT | 144 | TCAGCCACCAGAACCTCAACCTCA | 253 |
| CYR61 | NM_001554 | CYR61 | TGCTCATTCTTGAGAGAGCAT | 36 | GTGGCTGCATTAGTGTCCAT | 145 | CAGCACCCTTGGCAGTTTCGAAAT | 254 |
| DR5 | NM_003842 | TNFRSF10B | CTCTGAGACAGTGCTTCGATGACT | 37 | CCATGAGGCCCAACTTCCT | 146 | CAGACTTGGTGCCCTTTGACTCC | 255 |
| DUSP1 | NM_004417 | DUSP1 | AGACATCAGCTCCTGGTTCA | 38 | GACAAACACCCTTCCTCCAG | 147 | CGAGGCCATTGACTTCATAGACTCCA | 256 |
| DUSP4 | NM_001394 | DUSP4 | TGGTGACGATGGAGGAGC | 39 | CTCGTCCCGGTTCATCAG | 148 | TTGAGCACACTGCAGTCCATCTCC | 257 |
| DUSP6 | NM_001946 | DUSP6 | CATGCAGGGGACTGGGATT | 40 | TGCTCCTACCCTATCATTTGG | 149 | TCTACCCTATGCGCCTGGAAGTCC | 258 |
| ECOP | NM_030796 | ECOP | AGCCTACTGCAACACGCC | 41 | TGGGCACCCCACTACTTG | 150 | TTCACTACCTGTTCGTACGGGGGC | 259 |
| EGF | NM_001963 | EGF | CTTTGCCTTGCTCTGTCACAGT | 42 | AAATACCTGACACCCTTATGACAAATT | 151 | AGAGTTTAACAGCCCTGCTCTGGCTGACTT | 260 |
| EGFR | NM_005228 | EGFR | TGTCGATGGACTTCCAGAAC | 43 | ATTGGGACAGCTTGGATCA | 152 | CACCTGGGCAGCTGCCAA | 261 |
| EMP1 | NM_001423 | EMP1 | GCTAGTACTTTGATGCTCCCTTGAC | 44 | GAACAGCTGGAGGCCAAGTC | 153 | CCAGAGAGCCTCCCTGCAGCCA | 262 |
| EPHA2 | NM_004431 | EPHA2 | CGCCTGTTCACCAAGATTGAC | 45 | GTGGCGTGCCTCGAAGTC | 154 | TGCGCCCGATGAGATCACCG | 263 |
| ErbB3 | NM_001982 | ERBB3 | CGGTTATGTCATGCCAGATACAC | 46 | GAACTGAGAGCCACTGAAGAAAGG | 155 | CCTCAAAGGTACTCCCTCCTCCGG | 264 |
| ERBB4 | NM_005235 | ERBB4 | TGGCTCTTAATCAGTTTCGTTACCT | 47 | CAAGGCATATCGATCCTCATAAAGT | 156 | TGTCCCACGAATAATGCGTAAATTCTCCAG | 265 |
| EREG | NM_001432 | EREG | ATAACAAAGTGTAGCTCTGACATGAATG | 48 | CACACCCTGCAGTAGTTTGACTCA | 157 | TTGTTTGCATGGACAGTGCATCTATCTGGT | 266 |
| FCGR3A | NM_000569 | FCGR3A | GTCTCCAGTGGAAGGGAAAA | 49 | AGGAATGCAGCTACTCACTGG | 158 | CCCATGATCTTCAAGCAGGGAAGC | 267 |
| FGFR3 | NM_000142 | FGFR3 | CAAGATCTCCCGCTTCCC | 50 | GTTGGAGCTCATGGACGC | 159 | ACTCCAGGGACACCTGTGCCTTG | 268 |
| GCNT3 | NM_004751 | GCNT3 | CTTATGCTCCCTGCTCTGGA | 51 | AATTCAAGTCCCCAGCCC | 160 | CACCAGCGCGGCTATCTGCGTTTAT | 269 |
| GDF15 | NM_004864 | GDF15 | CGCTCCAGACCTATGATGACT | 52 | ACAGTGGAAGGACCAGGACT | 161 | TGTTAGCCAAAGACTGCCACTGCA | 270 |
| GPC3 | NM_004484 | GPC3 | TGATGCGCCTGGAAACAGT | 53 | CGAGGTTGTGAAAGGTGCTTATC | 162 | AGCAGGCAACTCCGAAGGACAACG | 271 |
| GPX1 | NM_000581 | GPX1 | GCTTATGACCGACCCCAA | 54 | AAAGTTCCAGGCAACATGT | 163 | CTCATCACCTGGTCTCCGGTGTGT | 272 |
| GREM1 | NM_013372 | GREM1 | GTGTGGGCAAGGAAGAAGC | 55 | GACCTGATTTGGCCTCACC | 164 | TCCACCCTCCTCCCTTCTCACTCACTCCAC | 273 |

FIG. 1 (Cont. 1)

| Gene | Accession Num | Official Symbol | FPrimerSeq | SEQ ID NO | RPrimerSeq | SEQ ID NO | ProbeSeq | SEQ ID NO |
|---|---|---|---|---|---|---|---|---|
| GRO1 | NM_001511 | CXCL1 | CGAAAAGATGCTGAACAGTGACA | 56 | TCAGGAACAGCCACCAGTGA | 165 | CTTCCTCCTCCCTTCTGGTCAGTTGGAT | 274 |
| GUS | NM_000181 | GUSB | CCCACTCAGTAGCCAAGTCA | 57 | CACGCAGGTGGTATCAGTCT | 166 | TCAAGTAAACGGGCTGTTTTCCAAACA | 275 |
| HB-EGF | NM_001945 | HBEGF | GACTCCTTCGTCCCCAGTTG | 58 | TGGCACTTGAAGGCTCTGGTA | 167 | TTGGGCCTCCCATAATTGCTTTTGCC | 276 |
| HER2 | NM_004448 | ERBB2 | CGGTGTGAGAAGTGCAGCAA | 59 | CCTCTCGCAAGTGCTCCAT | 168 | CCAGACCATAGCACACTCGGGCAC | 277 |
| HGF | M29145 | | CCGAAATCCAGATGATGATG | 60 | CCCAAGGAATGAGTGGATT | 169 | CTCATGGACCCTGGTGCTACACG | 278 |
| ID1 | NM_002165 | ID1 | AGAACCGCAAGGTGAGCAA | 61 | TCCAACTGAAGGTCCCTGATG | 170 | TGGAGATTCTCCAGCACGTCATCGAC | 279 |
| IL-8 | NM_000584 | IL8 | AAGGAAACATCTCACTGTGTGTAAAC | 62 | ATCAGGAAGGCTGCCAAGAG | 171 | TGACTTCCAAGCTGGCCGTGGC | 280 |
| INHBA | NM_002192 | INHBA | GTGCCCGAGCCATATAGCA | 63 | CGGTAGTAGTGGTGATGACTGTTGA | 172 | ACGTCCGGGTCCTCACTGTCCTTCC | 281 |
| ITGB3 | NM_000212 | ITGB3 | ACCGGGAGCCCTACATGAC | 64 | CCTTAAGCTCTTTCACTGACTCAATCT | 173 | AAATACCTGCAACCGTTACTGCCGTGAC | 282 |
| KCNK1 | NM_002245 | KCNK1 | GGAGGTAAGGCCTTCTGCAT | 65 | CAGCCGTCAGGAACAGGA | 174 | CTCCGTCATTGGCATTCCCTTCAC | 283 |
| KLRK1 | NM_007360 | KLRK1 | TGAGAGCCAGGCTTCTTGTA | 66 | ATCCTGGTCCTCTTTGCTGT | 175 | TGTCTCAAAATGCCAGCCTTCTGAA | 284 |
| KRT17 | NM_000422 | KRT17 | CGAGGATTGGTTCTTCAGCAA | 67 | ACTCTGCACCAGCTCACTGTTG | 176 | CACCTCGCGGTTCAGTTCCTCTGT | 285 |
| KRT19 | NM_002276 | KRT19 | TGAGCGGCAGAATCAGGAGTA | 68 | TGCGGTAGGTGGCAATCTC | 177 | CTCATGGACATCAAGTCGCGGCTG | 286 |
| LAMA3 | NM_000227 | LAMA3 | CAGATGAGGCACATGGAGAC | 69 | TTGAAATGGCAGAACGGTAG | 178 | CTGATTCCTCAGGTCCTTGGCCTG | 287 |
| LAMC2 | NM_005562 | LAMC2 | ACTCAAGCGGAAATTGAAGCA | 70 | ACTCCCTGAAGCCGAGACACT | 179 | AGGTCTTATCAGCACAGTCTCCGCCTCC | 288 |
| Maspin | NM_002639 | SERPINB5 | CAGATGGCCACTTTGAGAACATT | 71 | GGCAGCATTAACCACAAGGATT | 180 | AGCTGACAACAGTGTGAACGACCAGACC | 289 |
| MCP1 | NM_002982 | CCL2 | CGCTCAGCCAGATGCAATC | 72 | GCACTGAGATCTTCCTATTGGTGAA | 181 | TGCCCCAGTCACCTGCTGTTA | 290 |
| NCAM1 | NM_000615 | NCAM1 | TAGTTCCCAGCTGACCATCA | 73 | CAGCCTTGTTCTCAGCAATG | 182 | CTCAGCCCTCGTCGTCTTATCCACC | 291 |
| NEDD8 | NM_006156 | NEDD8 | TGCTGGCTACTGGGTGTTAGT | 74 | GACAACCAGGGACACAGTCA | 183 | TGCAGTCGTGTGTGCTTCCCTCTC | 292 |
| NR3C2 | NM_000901.1 | | GCAGAGCTGGCAGAGAGGTT | 75 | GGTGCTCACCAGGTCAT | 184 | CAACTGACCAAGCTGCTGGACTCC | 293 |
| NT5E | NM_002526 | NT5E | CTTAACGTGGGAGTGGAACC | 76 | GTGAAGCCTGCTCAGCTCTGCATA | 185 | CATGAGGCTGCTCAGCTCTGCATA | 294 |
| p14ARF | NM_000077 | CDKN2A | GCGGAAGGTCCCTCAGACA | 77 | TCTAAGTTTCCGGAGGTTTCTCA | 186 | CCCCGATTGAAAGAACCAGAGAGGCT | 295 |
| PDGFB | NM_002608 | PDGFB | ACTGAAGGAGAGACCCCTTGGAG | 78 | TAAATAACCCTGCCCACACA | 187 | TCTCCTGCCGATGCCCCTAGG | 296 |
| PGK1 | NM_000291 | PGK1 | AGAGCCAGTTGCTGTAGAACTCAA | 79 | CTGGGCCTACACAGTCCTTCA | 188 | TCTCTGCTGGGCAAGGATGTTCTGTTC | 297 |
| PHLDA1 | NM_007350 | PHLDA1 | CAAGACCAGGGCTGGAAC | 80 | GGATGGCCTGACGATTCTT | 189 | TACTGCACCATCTGCAGCGTGATC | 298 |
| PLAC8 | NM_016619 | PLAC8 | GAATGAATGCTGTCTGTGTGG | 81 | ATGCCATATCGGGTCCTGT | 190 | ACAAGCGTCGCAATGAGGACTCTC | 299 |
| PLAUR | NM_002659 | PLAUR | CCCATGGATGCTCCTCTGAA | 82 | CCGGTGGCTACCAGACATTG | 191 | CATTGACTGCCGAGGCCCATG | 300 |

FIG. 1 (Cont. 2)

| Gene | Accession Num | Official Symbol | FPrimerSeq | SEQ ID NO | RPrimerSeq | SEQ ID NO | ProbeSeq | SEQ ID NO |
|---|---|---|---|---|---|---|---|---|
| PLTP | NM_006227 | PLTP | GCGCAGGTTCCGAATCTAT | 83 | GGGCCTGTAATGGGATCAG | 192 | AACCATTCTGCACTGGAGTCGCTG | 301 |
| POSTN | NM_006475 | POSTN | GTGGCCCAATTAGGCTTG | 84 | TCACAGGTGCCAGCAAAG | 193 | TTTCTCCATCTGCCTCAGAGCAGA | 302 |
| PTP4A3 | NM_007079 | PTP4A3 | AATATTTGTGCGGGGTATGG | 85 | AACGAGATCCCTGTGCTTGT | 194 | CCAAGAGAAACGAGATTTAAAAACCCACC | 303 |
| PTPD1 | NM_007039 | PTPN21 | CGCTTGCCTAACTCATCTACTTTCC | 86 | CCATTCAGACTGCGCCACTT | 195 | TCCACGCAGCGTGGCACTG | 304 |
| PTTG1 | NM_004219 | PTTG1 | GGCTACTCTGATCTATGTTGATAAGGAA | 87 | GCTTCAGCCATCCTTAGCA | 196 | CACACGGGTGCCTGGTTCTCA | 305 |
| QPRT | NM_014298 | QPRT | TGATTCTCCCTCAAGCTGTT | 88 | TTCCGGTTTAGGACTAGTGGA | 197 | CACTGGAGCCACCTCTTTGGCA | 306 |
| RASSF1 | NM_007182 | RASSF1 | AGTGGGAGACACCTGACCTT | 89 | TGATCTGGGCATTGTACTCC | 198 | TTGATCTTCTGCTCAATCTCAGCTGAGA | 307 |
| SATB2 | NM_015265 | SATB2 | GTAGGCCTGTACCCAGACCA | 90 | GTGTTTGGGGAGATCCAGC | 199 | AAGCCATCCACACTCTTTCGGCTC | 308 |
| SERPINB1 | NM_030666 | SERPINB1 | CTGGCCAGTGTGTGGATTTC | 91 | CTTTGACCCACTGTGTTATGG | 200 | TTCCTTGCATCTTCAGAGGCATGC | 309 |
| SFN | NM_006142 | SFN | GAGAGAGCCAGTCTGATCCA | 92 | AGGCTGCCATGTCCTCATA | 201 | CTGCTCTGCCAGCTTGGCCTTC | 310 |
| SLC26A3 | NM_000111 | SLC26A3 | TAGGAGATTGCTTCGGCATC | 93 | GAATAGACGCTGGCAACTGA | 202 | AAGGCCACTGCAAATGCAACCATT | 311 |
| SORBS1 | NM_006434 | SORBS1 | ACTGCTCCGGCAGGTAGAT | 94 | ATGCCTTGTCGGGATGTC | 203 | CGGGATTCCTCCCTTCGTACCAGTT | 312 |
| SPHK1 | NM_021972 | SPHK1 | GGCAGCTTCCTTGAACCAT | 95 | GCAGTTGGTCAGGAGGTCTT | 204 | TGGTGACCTGCTCATAGCCAGCAT | 313 |
| SPON1 | NM_006108 | SPON1 | GATGCTCCATGTGCAAAG | 96 | GGTGTGTGGCACTGCTGGCAT | 205 | ATGCGCTTCTCGCCTGTGATGTC | 314 |
| TFRC | NM_003234 | TFRC | GCCAACTGCTTTCATTGTG | 97 | ACTCAGGCCCATTTCCTTTA | 206 | AGGGATCTGAACCAATACAGAGCAGACA | 315 |
| TGFA | NM_003236 | TGFA | GGTGTGCCACAGACCTTCCT | 98 | ACGGAGTTCTTGACAGAGTTTTGA | 207 | TTGGCCTGTAATCACCTGTGCAGCCTT | 316 |
| TGFBR2 | NM_003242 | TGFBR2 | AACACCAATGGGTTCCATCT | 99 | CCTCTTCATCAGGCCAAACT | 208 | TTCTGGGCTCCTGATTGCTCAAGC | 317 |
| TIMP1 | NM_003254 | TIMP1 | TCCCTGCGGTCCAGATAG | 100 | GTGGGAACAGGGTGGACACT | 209 | ATCCTGCCCGGAGTGGAACTGAAGC | 318 |
| TITF1 | NM_003317 | NKX2-1 | CGACTCCGTTCTCAGTGTCTGA | 101 | CCCCTCCATGCCCCACTTCT | 210 | ATCTTGAGTCCCCTGGAGGAAAGC | 319 |
| UBB | NM_018955 | UBB | GAGTCGACCCTGCACCTG | 102 | GCGAATGCCATGACTGAA | 211 | AATTAACAGCCACCCCTCAGGCG | 320 |
| upa | NM_002658 | PLAU | GTGGATGTGCCCTGAAGGA | 103 | CTGCGGATCCAGGGTAAGAA | 212 | AAGCCAGGCGTCTACACGAGAGTCTCAC | 321 |
| VAV3 | NM_006113 | VAV3 | CAGGTGTAGCCTCCTCT | 104 | GGGATGTGTCCACTGAACCT | 213 | ATCAATCCGTCTGGGTGCCAGAAC | 322 |
| VEGF | NM_003376 | VEGFA | CTGCTGTCTTGGGTGCATTG | 105 | GCAGCCTGGGACCACTTG | 214 | TTGCCTTGCTGCTCTACCTCCACCA | 323 |
| VEGFC | NM_005429 | VEGFC | CCTCAGCAAGACGTTATTTGAAATT | 106 | AAGTGTGATTGGCAAACTGATTG | 215 | CCTCTCTCTCAAGGCCCCAAACCAGT | 324 |
| VIL2 | NM_003379 | EZR | TCTGAAGCACTCTCGCACAC | 107 | CACTGTCCTCTGCCAGC | 216 | CAGTGATTCCCTCCTCCGTCACT | 325 |
| VIPR1 | NM_004624 | VIPR1 | CCCAAGGACTGAGGGACTCT | 108 | AGACCTAGCATTCGCTGGTG | 217 | TGCCTTCTCATTCCCAGAGGCTT | 326 |
| XIAP | NM_001167 | XIAP | GCAGTTGGAAGACACAGGAAAGT | 109 | TGCGTGGCACTATTTTCAAGA | 218 | TCCCCAAATTGCAGATTTATCAACGGC | 327 |

FIG. 1 (Cont. 3)

| Gene | Accession Num. | Official Symbol | AmpliconSequence | SEQ ID NO. |
|---|---|---|---|---|
| ADAM15 | NM_003815 | ADAM15 | GGCGGGATGTGGTAACAGAGACCAAGACTGTGGAGTTGGTGATCACTCGGAGGCCCAGAAAT | 328 |
| ADAM17 | NM_003183 | ADAM17 | GAAGTGCCAGGAGGCGATTAATGCTACTTGCCTACTGCAGTGTCCTACTGCACAGGTAATAGCAGTGAGTGCCCG | 329 |
| AMACR1 | NM_014324 | AMACR | GGACAGTCAGTTTAGGGTTGCCTGTATCCAGTAACTCGGGCCTGTTTCCCCGTGGGTCTCTGGGCTGTC | 330 |
| ANXA1 | NM_000700 | ANXA1 | GCCCCTATCCTACCTTCAATCCATCCTCGGATGTCGCTGCCTTGCATAAGGCATAATGTTAAAGG | 331 |
| ANXA2P2 | M62898 |  | CGGACACATCTGGTGACTTCTAGTAGTGAAACCGTCCTCGGAGCGACTATGAACTACTCAGAAGAGTATGATAACGAACCACAA | 332 |
| AREG | NM_001657 | AREG | TGTGAGTGAAATGCCTTCTAGTAGTGAAACCGTCCTCGGAGCGACTATGAACTACTCAGAAGAGTATGATAACGAACCACAA | 333 |
| ATP5E | NM_006886 | ATP5E | CCGCTTTCGCTACAGCATGTCCTTCGGGCTGGTGACAGGGAAGACATCACTGAGCCTGCCATCGTGCTCTTCGTCATCTGA | 334 |
| B-Catenin | NM_001904 | CTNNB1 | GGCTCTTGTGCGTACTGTCCTTCGGGCTGGTGACAGGGAAGACATCACTGAGCCTGCCATCGTGCTCTTCGTCATCTGA | 335 |
| Bak | NM_001188 | BAK1 | CCATTCCCACCATTCTACCTGAGGCCAGGAGACGTCTGGGGTGTGGGGATTGGTGGGTCTATGTTCCC | 336 |
| Bcl | NM_001191 | BCL2L1 | CTTTTGTGAACTCTATGGGAACAATGCAGCCGAGCACCTCAAGGGTCTCCAGCACCTCACGCCCCTCGTCTTCAACGCTG | 337 |
| Bdx |  |  |  |  |
| BGN | NM_001711 | BGN | GAGCTCCGCAAGGATGACTTCAAGGTCTCCAAGGATGACTTCAAGGTCTCCAGCACCTCGGTGAACAACAAG | 338 |
| BM039 | NM_018455 | CENPN | GTGAGTCCACTGGGGACTGGCAGGCTCTAAGCACAACAGGCACACAAGCAGTTCCTAACGAG | 339 |
| BRAF | NM_004333 | BRAF | CCTTTCCGACCACCAGCAGATGAAGATCATCGAAATCAATTTGGGAACAGATCCTCATCAGCTCCCAATGTGCATATAAA | 340 |
| BRCA1 | NM_007295 | BRCA1 | TCAGGGGCTAGAAATCTGTTGCTATGGGCCCTTCACCAACATCAATGCCCACAGATCAACTGAATGG | 341 |
| BRCA1 | NM_007295 | BRCA1 | TCAGGGGCTAGAAATCTGTTGCTATGGGCCCTTCACCAACATCAATGCCCACAGATCAACTGAATGG | 342 |
| BRK | NM_005975 | PTK6 | GTGCAGGAAAGGTTCACAAATGTGGAGTGTCGCGTCCAATACACGCGTGTCCTCCTTACTCCATCGTGTGC | 343 |
| BTC | NM_001729 | BTC | AGGGAGAGCCGCTTCGTGGTGGCCGAGCAGAGCTACTCTCATCGGACGTCCGCCCAAGCCCTAGGATGAAGGCTACATTGGAGCAAGGTGTGAGAG | 344 |
| C13orf18 | NM_025113 | C13orf18 | TCCTCAACAGAGGTACACATGGTCCGCCTCCTTTTGCTCTGCACCAAGCCCTAGGAT | 345 |
| CA9 | NM_001216 | CA9 | ATCCTAGCCCTGGTTTTGGCCTCTGTGACCAAGTTATATCCAGTTAAGGCAATCTCCTGCTGTGACTTTGAACTAACTGGGGA | 346 |
| Cad17 | NM_004063 | CDH17 | AAGGCCAAGAACCGAGTCAATTATATTCCAGTTAAGGCAATCTCCTGCTGTGACTTTGAACTAACTGGGGA | 347 |
| CCNE1 | NM_001238 | CCNE1 | AAAGAAGATGATGACCGGCTTCCTAACTGGGGCTTTCTTGACATGTAGGTTGCTTGTCTGCACTTAAGCTGTTCTCCAGTGCGTGTGATT | 348 |
| CCNE2 | NM_057749 | CCNE2 | ATGCTGTGGCCTCCTTACCCGAGAACAGGTCCAGCTTGATTCTCGTCTCTGCACTTAAGCTGTTCTCCAGTGCGTGTGATT | 349 |
| CD134 | NM_003327 | TNFRSF4 | GCCCAGTGCGGAGAACCACCATGTCTGCCCATCACGGCTACCAATATGGACTCATAGTACAAGCTTGAGGATGTCACCAATTAACC | 350 |
| CD18 | NM_000211 | ITGB2 | CGTCAGGAGGACCACCATGTCTGCCCATCACGGCTACCAATATGGACTCATAGTACAAGCTTCAGCCTACTGCAAATCCAAACAC AGGT | 351 |
| CD44E | X55150 |  | ATCACCGACACAGCACAGAACCAGGACTGGACCCAGTGGAACCCAAGCCATTCAAATCCGAAGTGCTACTTCAG | 352 |
| CD44v3 | AJ251595v3 |  | CACACAAAAACAGCAGCATCCAATGCAAGGACAGTTCCTGGACTGATTTCTTCAACCCAA | 353 |
| CD44v6 | AJ251595v6 |  | CTCATATACCAGCATCCAATGCAAGGACAGTTCCTGGACTGATTTCTTCAACCCAA | 354 |
| CDC25B | NM_021873 | CDC25B | AAACGAGCAGTTTGCCATCAGACGCTTCCAGTCTATGCCGGTCATGCCGGTGGGCCCAGCCTCTGGGAACATCACCAA C | 355 |
| CEACAM6 | NM_002483 | CEACAM6 | CACAGCCTCACTTCTAACCTTCTGGAACCTGCCAAGCTCCAAGCACTGCCAAGCTCACTATTGAATCCACGCCATTCAA | 356 |
| CGA | NM_001275 | CHGA | CTGAAGGAGCTCCAAGAACCTGCTCTCCAAGGCGTCACACGTGAACAGACATCAGCAGAAGAAACACAGCGTTTG | 357 |
| CHN2 | NM_004067 | CHN2 | GATCGCTGAGTGGGCTACTGTTCTCTGCTGTTTGCTACCATGGCGTCCTGACCAGTGTCCTGACCAGTGTCCTACCGGGTACCT | 358 |
| CKMT2 | NM_001825 | CKMT2 | CTAACTGGCCGCAATGCTTCGCAGTCAGCCTCCTGCCCCACCCTTGGCTTTGGGTACAGCATGTGAAGCGCTGATCCTGAGTCA | 359 |
| CLTC | NM_004859 | CLTC | ACCGTATGGACAGCCACACCCCTTGTTCAGTGTGCCCACGACACAATAATGTGCGATCGG | 360 |
| cMet | NM_000245 | MET | GACATTTCCAGTCCTGCAGTCAATTGCAGCCAGAACCTGACTGAATTCTTCAACCCAAGTGCTACTTCAG AG | 361 |
| CYP2B6 | NM_000767 | CYP2B6 | ATCCAACGCACACAGTGAATTCAGCCAGAACCTGACTGAATTCTTCAACCCAAGTGCTACTTCAG | 362 |
| CYR61 | NM_001554 | CYR61 | TGCTCATTCTTGAGGAGCATTAAGGTATTTCGAAACTGCCAAGGGTGCTGGTGCGGATGACACTAATGCAGCCAC | 363 |

FIG. 2

| Gene | Accession Num | Official Symbol | AmpliconSequence | SEQ ID NO: |
|---|---|---|---|---|
| DR5 | NM_003842 | TNFRSF10B | CTCTGAGACAGTGCTTCGATGAGACTTTGGTGCCTTTGACTCCTGGGAGCCGCTCATGAGGAAGTTGGGCCTCATGG | 364 |
| DUSP1 | NM_004417 | DUSP1 | AGACATCAGCTCCTGGTTCAACGAGGCCATTCATGAGACTCCATCAAGAATGCTGGAGGAAGGGTGTTTGTC | 365 |
| DUSP4 | NM_001394 | DUSP4 | TGGTGACGATGGGAGCTGCGGAGGACTGGACTGCAGTGCTGCTCAAAGGCTGATGAACCGGGACGAG | 366 |
| DUSP6 | NM_001946 | DUSP6 | CATGCAGGGACTGGGATTCCAGGCGGACTTCCAGGTAGAACAAGGTAGTGAAGGATATAGGGTAGGAGCA | 367 |
| ECOP | NM_030796 | ECOP | AGCCTACTGCAACACGCCTCCGCCCCCGTACGAACAGGTAGTGAAGGCCAAGTAGTGGGGTGCCCA | 368 |
| EGF | NM_001963 | EGF | CTTTGCCTTTGCTCTGTCACAGTGAAGTCAGCCAGAGTGAAACTCTGTGAAATTTGTCATAAGGGTGTCAGGTATTT | 369 |
| EGFR | NM_005228 | EGFR | TGTCGATGGGACTTCCAGAATGGCACCACCTGGGCAGCTGCCAAAAGTGTGATCCAAGCTGTCCCAAT | 370 |
| EMP1 | NM_014423 | EMP1 | GCTAGTACTTTGATGCTCCCTTGATGGGGTCCAGAGAGCCTCTGCAGAGAACGTCAGCAGCGACTTGGCCTCCAGCTGTTC | 371 |
| EPHA2 | NM_004431 | EPHA2 | CGCCTGTTCACCAAGATTGACACCATTGCGCCGATGAGATCAGCAGCGTCAGCAGCGACTTCGAGGCACGCCAC | 372 |
| ErbB3 | NM_001982 | ERBB3 | CGGTTATGTCATGCCAGATACACACCTCAAAGGTACTCCCTGGAGAATTTACGCATTATTCGTGGGACAAAACTTTATGAGGATGTGGTCTCAGTTC | 373 |
| ERBB4 | NM_005235 | ERBB4 | ATGACGCCTCTTAATCAGTTCGTTACCTGCCTCTGGAGAATTGTTTGCATGGCTATATTCGTGGACAGTGCATCTATCTGGTGGACATGAGTCAAAACTACTGCAG | 374 |
| EREG | NM_001432 | EREG | ATAACAAAGTGTAGCTCTGACATGAATGGCTATTGTTTGCAATGGACAGTGCATCTATCTGGTGGACATGAGTCAAAACTACTGCAGGTGTG | 375 |
| FCGR3A | NM_000569 | FCGR3A | GTCTCCAGTGGAAGGGAAAAGCCCATGCTGATCTTCAAGCAGGAGAAGCCCCAGTGAGTAGCTGCATTCCT | 376 |
| FGFR3 | NM_000142 | FGFR3 | CAAGATCTCCCGCCTTGCTCTGCTGGAATCACCAGCGGCTATCTGCGTTTATGGGGCTGGGGACTTGAATT | 377 |
| GCNT3 | NM_004751 | GCNT3 | CTTATGCTCCCAGACCTATGATGACTTGTAGCCAAAGACTGCCACTGCATATGAGCAGTGCATCCTTCCACTGT | 378 |
| GDF15 | NM_004864 | GDF15 | CGCTCCAGATGCGCCTGGAAACAGTCAGCTCATCACCTGGTCTCCGGATGTGTGCAACGATGTTGCCTGGAACTTT | 379 |
| GPC3 | NM_004484 | GPC3 | TGATGCGCCTCTGGAAACAGTCAGCTCATCACCTGGTCTCCGGATGTGTGCAACGATGTTGCCTGGAACTTT | 380 |
| GPX1 | NM_000581 | GPX1 | GCTTATGACCGACCCCAAGCTCACTCACCTGGTCTCCGGATGTGTGCAACGATGTTGCCTGGAACTT | 381 |
| GREM1 | NM_013372 | GREM1 | GTGTGGGCAAGGACAACAAGCAGGATAGTGAGTGAGGAAGCACTGGTGTGGCCAAATCAGGTC | 382 |
| GRO1 | NM_001511 | CXCL1 | CGAAAAGATGCTGAACAGTGACAAATCCAACTGACCAGAGAAGCTCACTGGTGTGCCACTGTTCCTGA | 383 |
| GUS | NM_000181 | GUSB | CCCATCAGTGCCAAGTCACAGTTGTTGGAGAATGGGCCCTGGTCCTTACTGAAGACTGATACCACCTGCGTG | 384 |
| HB-EGF | NM_001945 | HBEGF | GACTCCTTCGTCCCCCAGTTGCCGTCTCAGGATTGGGCCTCCATAATTGCTTGCCAAAATACCAGAGCCTTCAAGTGCCA | 385 |
| HER2 | NM_004448 | ERBB2 | CGGTGTGAGAAGTGCAGCAGGCCCTGCCAGGTGTCCATGTCCTATGGTCTACAGCACTTGCGAGAGG | 386 |
| HGF | M29145 | | CCGAAATCCAGATGATGATGCTAAGGTGGCTGCTACAGCACGTGGTGCTACAGCACGTGGTGGCGGGAAATCCACTCATTCCTTGGG | 387 |
| ID1 | NM_002165 | ID1 | AGAACGCAAGGTGAGCAACTTCACTGTGTGAGCAAGGTGAGCAACTTCAGTGGA | 388 |
| IL-8 | NM_000584 | IL8 | AAGGAACCATCTCACTGTGTGTAAACATGACTTCCAAGCTGGCCGTGGCTCTCTTCCTGAT | 389 |
| INHBA | NM_002192 | INHBA | GTGCCGGGAGCCCTACATAGACCGAATGCCGAAAATACCTCGAACCGTTCACTGCCGTCCTTACTGCCGTTACTGCAACCACTACCG | 390 |
| ITGB3 | NM_000212 | ITGB3 | ACCGGAGGTAAGGCCTTCTTGTTCTGCATCATCCGTCAAAATGCCAGCCTTCGTCCGTGAGGAGATTCAGTCAGTGAAAGAGCTTAAGG | 391 |
| KCNK1 | NM_002245 | KCNK1 | GGAGGTAAGGCCTTCTTGTTCTGCATCATCCGTCAAAATGCCAGCCTTCGTCCTCGTTCCTGACGGCTG | 392 |
| KLRK1 | NM_007360 | KLRK1 | TGAGAGCCAGGCTGGTTCTTCAGCAAGACAGTACCAGCCATCAAATGCCAGCAACAGTGAGCTGAGCGACCAGGAT | 393 |
| KRT17 | NM_000422 | KRT17 | CGAGGATTGGTTCTTCAGCAAGACAGTACCAGCCATCATGGACATCAAGACGCGCCTCGAGCAGGAGATCCACCTACCGCA | 394 |
| KRT19 | NM_002276 | KRT19 | TGAGGGCAGAATCAGGAGTCAGGAGATAGGTCATCAGCACAGTTGCTGCCTCTCTGACCGTTCTGCCATTCAA | 395 |
| LAMA3 | NM_000227 | LAMA3 | CAGATGAGGCAGAATTGAAGCAGACAGAATATTTAGCTGACAACAGTGAACGACCTGGTTGCTCAACACGTTCTGCCATTCAA | 396 |
| LAMC2 | NM_005562 | LAMC2 | ACTCAAGCGAACCACTTGAGAACATCAATGCCCCAGTCACTCTGTTATAACTCAACGACCAGCACCAAAATCCTTGTGTTAATGCTGC | 397 |
| Maspin | NM_002639 | SERPINB5 | CAGATGGCCACCCAGATGCAATCAATGCCCCAGTCACTCTGTTATAACTCAACGACCAGCACCAAAATCCTTGTGTTAATGCTGC | 398 |
| MCP1 | NM_002982 | CCL2 | CGCTCAGCCAGATGCAATCAATGCCCCAGTCACTCTGTTATAACTCAACGACCAGCACCAAAATCCTTGTGTTAATGCTGC | 399 |

FIG. 2 (Cont. 1)

| Gene | Accession Num | Official Symbol | AmpliconSequence | SEQ ID NO: |
|---|---|---|---|---|
| NCAM1 | NM_000615 | NCAM1 | TAGTTCCCAGCTGACCATCAAAAAGGTGGATAAGAACGACGAGGCTGAGTACATCTGCATTGCTGAGAACAAGGCTG | 400 |
| NEDD8 | NM_006156 | NEDD8 | TGCTGGCTACTGGGTGTTAGTTGCAGTCCTGTGCTTCCCTCTCTTATGACTGTGTCCCTGGTTGTC | 401 |
| NR3C2 | NM_000901.1 | | GCAGAGCTGGGACAGAGGTTCTACCAAGTTGCTGGACTCCATGCATGACCTGGTGAGCGACC | 402 |
| NT5E | NM_002526 | NT5E | CTTAACGTGGGAGGTCCCTCAGACATCCCCGATTGAAAGAACCAGGACATCGGCAGGAGAGTGTGTGGGCAGGGTATTA | 403 |
| p14ARF | NM_000077 | CDKN2A | GCGGAAGGAGTCCCTCAGACATCCCCGATTGAAAGAACCAGGACATCGGCAGGAGAGTGTGTGGGCAGGGTATTA | 404 |
| PDGFB | NM_002608 | PDGFB | ACTGAAGGAGAGACCCTTGGAGCTAGAAACTCAAATCTCTGCTGGGCAAGTGTGTGGGCAGGGTATTA | 405 |
| PGK1 | NM_000291 | PGK1 | AGAGCCAGTTGCTGTTAGAACGCCGAGATCACGCTCACAGATGGTGCAGTACAAGAATCGTCAGGCCATCC | 406 |
| PHLDA1 | NM_007350 | PHLDA1 | CAAGACCAGGGCTGGAACGCCGAGATCACGCTCACAGATGGTGCAGTACAAGAATCGTCAGGCCATCC | 407 |
| PLAC8 | NM_016619 | PLAC8 | GAATGAATGCTGTCTGTCTGTGGAACAAGCGTGGCAATGAGGACTCTCTACAGGACCCGATATGGCAT | 408 |
| PLAUR | NM_002659 | PLAUR | CCCATGGATGCTCCTCTGAAGAGACTTTCCTGCATTGACTGCCGAGTCGCGTGGCTCTGATCCCATTACAGCCC | 409 |
| PLTP | NM_006227 | PLTP | GCGCAGGTTCCGAATCTATTCCAACCATTCTGCACTGAGGCCAGATGGAGAATACACTTTGCTGGCACCTGTGA | 410 |
| POSTN | NM_006475 | POSTN | GTGCCCCAATTAGGCTTGGCATGGGGTATGGGGTTTTTAAATCTCGTTTTGGACAAGCACAGGGATCTCGTT | 411 |
| PTP4A3 | NM_007079 | PTP4A3 | AATATTTGTGCGGGTATGGGGGTCCCGTTGACACTTGATCCACCAGCGTGGCACTGGACGTAAGTGGGCAGTCTGAATGG | 412 |
| PTPN21 | NM_007039 | PTPN21 | CGCTTGCCTAACTCATCTCATACTTTCCCGTTGACACTTGATCCACCAGCGTGGCACTGGACGTAAGTGGGCAGTCTGAATGG | 413 |
| PTTG1 | NM_004219 | PTTG1 | GGCTACTCTGATCTATGTTGATAAGGAAAATGGGAAGAGTGGCTCCAGTGCCCAAAATCCACTAGTCCTAAACCGGAA | 414 |
| QPRT | NM_014298 | QPRT | TGATTTCTCCCTCAAGCTGTTTGCCAAAGAGGTGGCTCCAGTGCCCAAAATCCACTAGTCCTAAACCGGAA | 415 |
| RASSF1 | NM_007182 | RASSF1 | AGTGGGAGGCCTGTACCAGAGCTGACCTTTCTCAAGCTGAGATTGAGCAGAAGATCAAGGAGTACAATGCCCAGATCA | 416 |
| SATB2 | NM_015265 | SATB2 | GTAGGCCCAGTGTGATTTTCAGCATGCCTCTCTGAAAGATGCAGGAAAGACCATAAACCAGTGGGTCAAAG | 417 |
| SERPINB1 | NM_030666 | SERPINB1 | CTGGCCAGTGTGGATTTTCAGCATGCCTCTCTGAAAGATGCAGGAAAGACCATAAACCAGTGGGTCAAAG | 418 |
| SFN | NM_006142 | SFN | GAGAGAGCCAGTCTGATCCAGAAGGCCAAGCTGTTGCATTGCAGTGGCCTTTCAGTTGCCAGCGTCTATTC | 419 |
| SLC26A3 | NM_000111 | SLC26A3 | TAGGAGATTGCTCCGGCAGGTAGATGAGAACTGGTACGAAGGGAGGAGCAGGTCACCAATGAAGACCTCCGACCAACTGC | 420 |
| SORBS1 | NM_006434 | SORBS1 | ACTGCTCCGGCAGCTTCCTTGAACCATTATGCTGGCTATGGCAAAGCCGAGACATCACACGAGCAGGTCACCAATGAAGACCTCCGACCAACTGC | 421 |
| SPHK1 | NM_021972 | SPHK1 | GATGAGCTTCCTCATGTGCAAAGCCGAGACATCACACGAGCAGGTCACCAATGAAGACCTCCGACCAACTGC | 422 |
| SPON1 | NM_006108 | SPON1 | GCCAAACTGCTTTCATTTGTGAGGGATCTGAACCAATACAGAGCAGACCATAAAGGAAAATGGGCCTGAGT | 423 |
| TFRC | NM_003234 | TFRC | GGTGTGCCACAATGGGTTCCATCTTTCCTACTTGCGCCTGTAATCACCTGTCGAGCCTTTTGTGCGCCTGAAAACTCTGTCAAGAACTCCGT | 424 |
| TGFA | NM_003236 | TGFA | AACACCAATGGGTTCCCAGATAGCCTAGACATCTTGAGTCCCTGCCGAGTGGAACTGAAGCCTGCACAGTGTCCACCCTGTTCCCAC | 425 |
| TGFBR2 | NM_003242 | TGFBR2 | TCCCTGCGGTCCGTTCTCGAGTGTCTGACATCTTGAGTCCCTGCCGAGTGGAACTGAAGCCTGCACAGTGTCCACCCTGTTCCCAC | 426 |
| TIMP1 | NM_003254 | TIMP1 | CGACTCCGTTCTCGAGTGTCTGACATCTTGAGTCCCTGCCGAGTGGAACTGAAGCCTGCACAGTGTCCACCCTGTTCCCAC | 427 |
| NKX2-1 | NM_003317 | TITF1 | GAGTCGACCCTGGTCCCGAGCGCGTCTACACGACGACAAGCCAGGCGCTCACACACTTCAGTCATGCATTCGCAGTGC | 428 |
| UBB | NM_018955 | UBB | GTGGATGTGCCCTAGCCTGCCCTCTCATCAGAACTCAAGGTTCAGTGGACACATCCC | 429 |
| upa | NM_002658 | PLAU | CAGGTGTGAGCCTGCCCTCTCATCAGAACTCAAGGTTCAGTGGACACATCCC | 430 |
| VAV3 | NM_006113 | VAV3 | TGCTGTCTTGGGTCATTGAAATTATTTGAAATTACAGTGCCTTGCCTCTCTCCCGTCACTCACCAAGGCCCCCAAATCAGTTGGGATGTGGTCCCAGGCTGC | 431 |
| VEGFA | NM_003376 | VEGF | CCTCAGCAAGACACTCTGCACACAACAGTGATTACACCTCGAAGCCTCTGAAGCCTCTCTCCCGTCACTCACCAAGGCCCCCAAATCAGTTGCCAATCACACTT | 432 |
| VEGFC | NM_005429 | VEGFC | TCTGAAGCACTCTCGCACACAACAGTGATTACACCTCGAAGCCTCTGAAGCCTCTCTCCCGTCACTCACCAAGGCCCCCAAATCAGTTGCCAATCACACTT | 433 |
| EZR | NM_003379 | VIL2 | CCCAAGGACTGAGGGACTCTGAAGCCTCTGAAGTATCCCAAATTGCAGATTTTATCTTATCAACGGCTTTATCTTGAAAATAGTGCCACGTG | 434 |
| VIPR1 | NM_004624 | VIPR1 | CCCAAGGACTGAGGGACTCTGAAGCCTCTGAAGTATCCCAAATTGCAGATTTTATCTTATCAACGGCTTTATCTTGAAAATAGTGCCACGTG | 435 |
| XIAP | NM_001167 | XIAP | GCAGTTGGAAGACACACAGGAAGAAGTATCCCAAATTGCAGATTTTATCTTATCAACGGCTTTATCTTGAAAATAGTGCCACGCA | 436 |

FIG. 2 (Cont. 2)

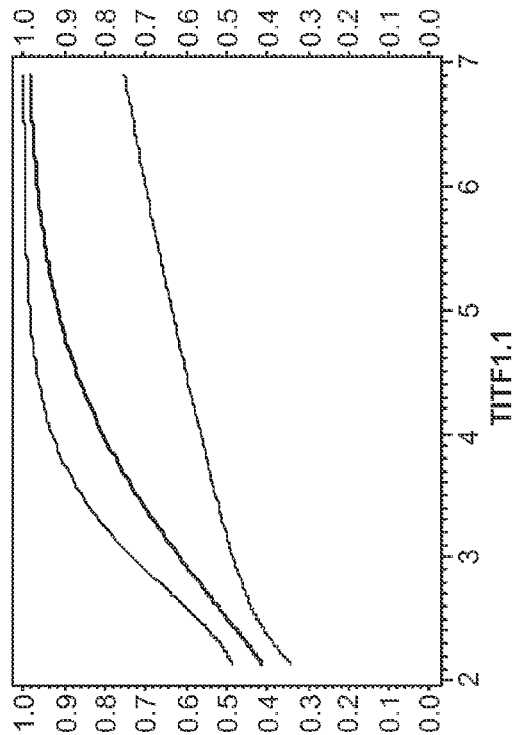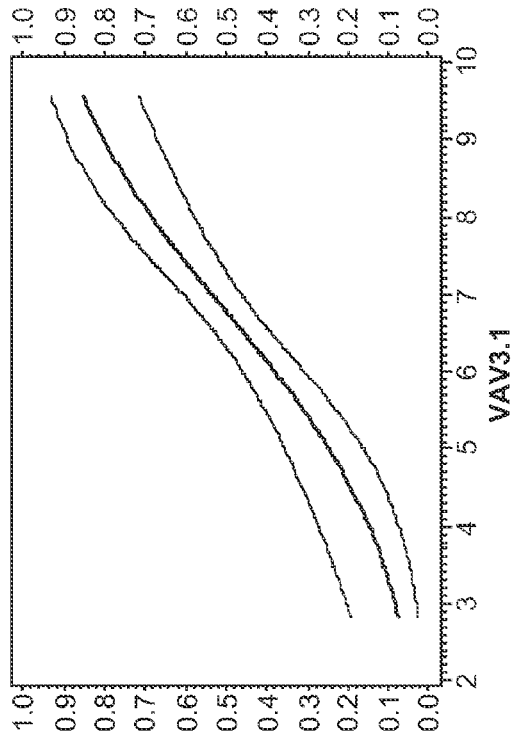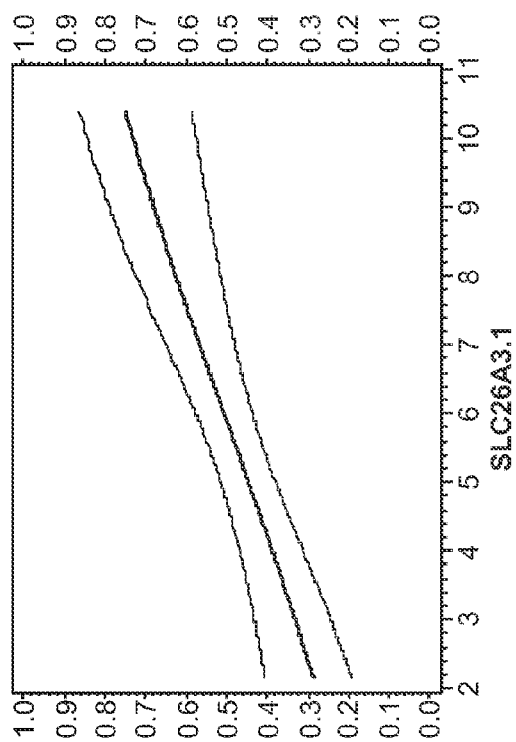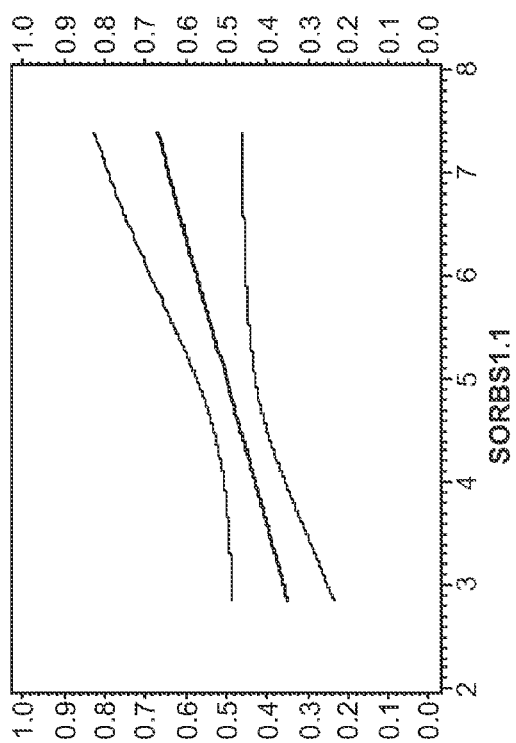
FIG. 3D

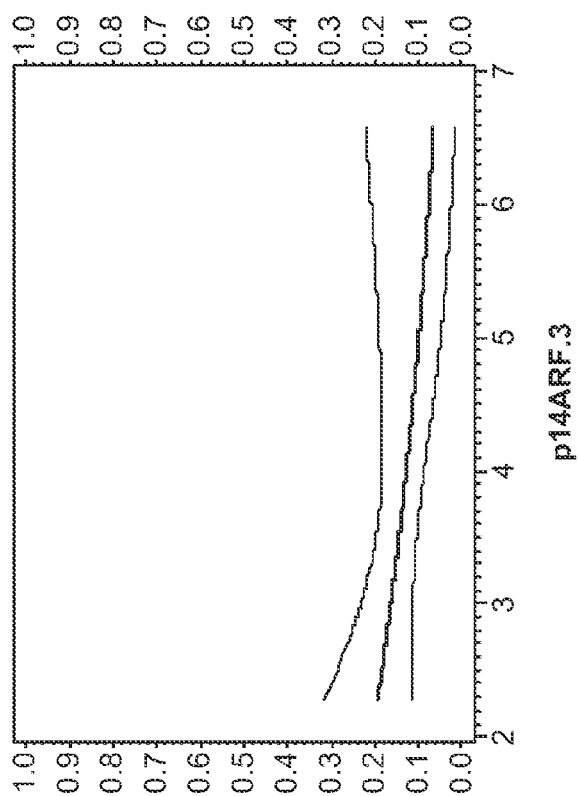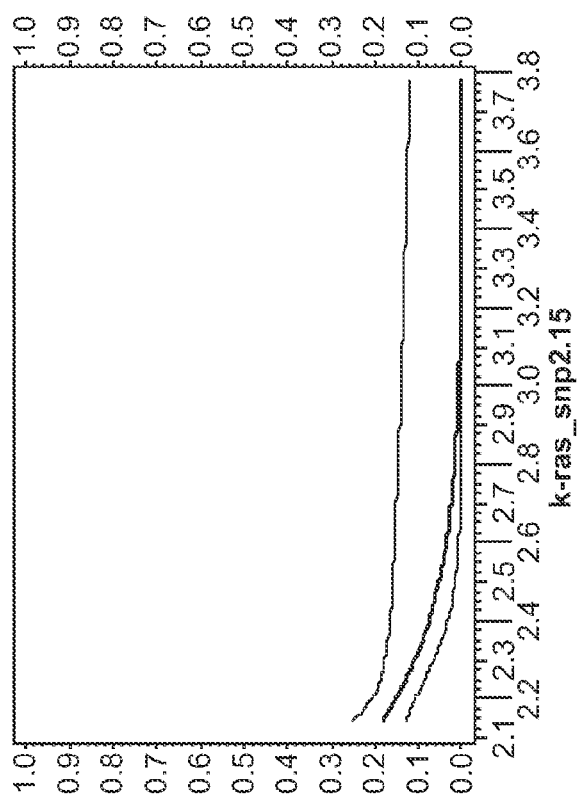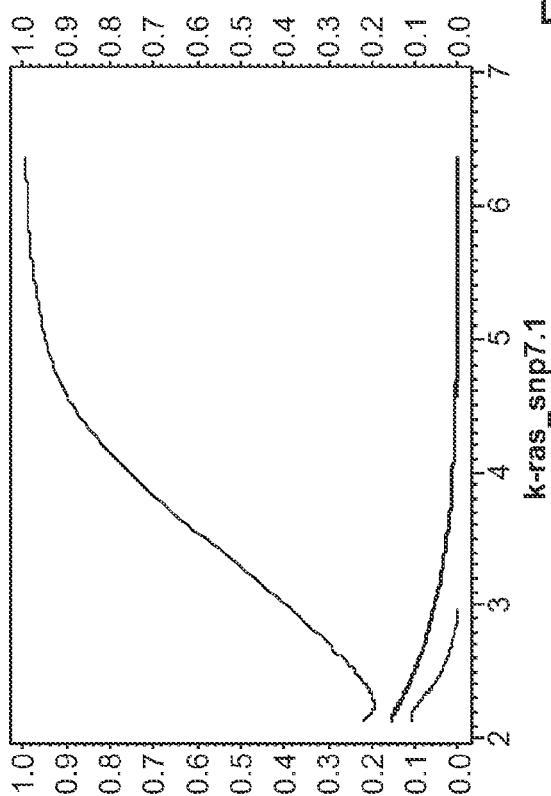
FIG. 6F

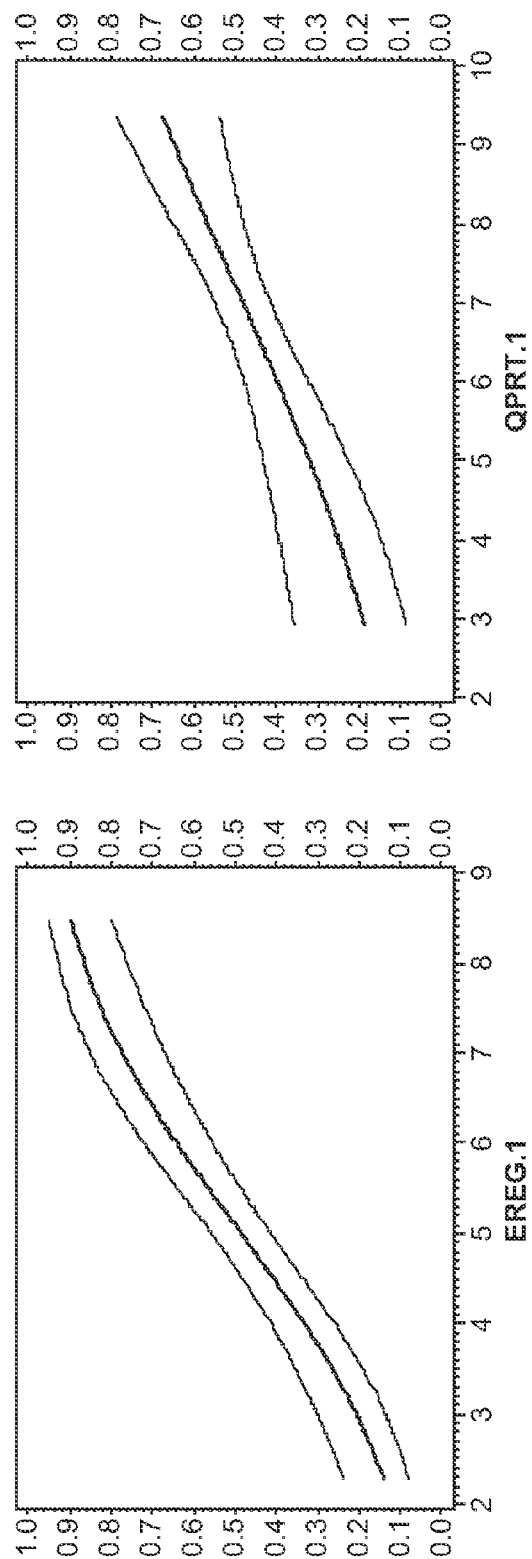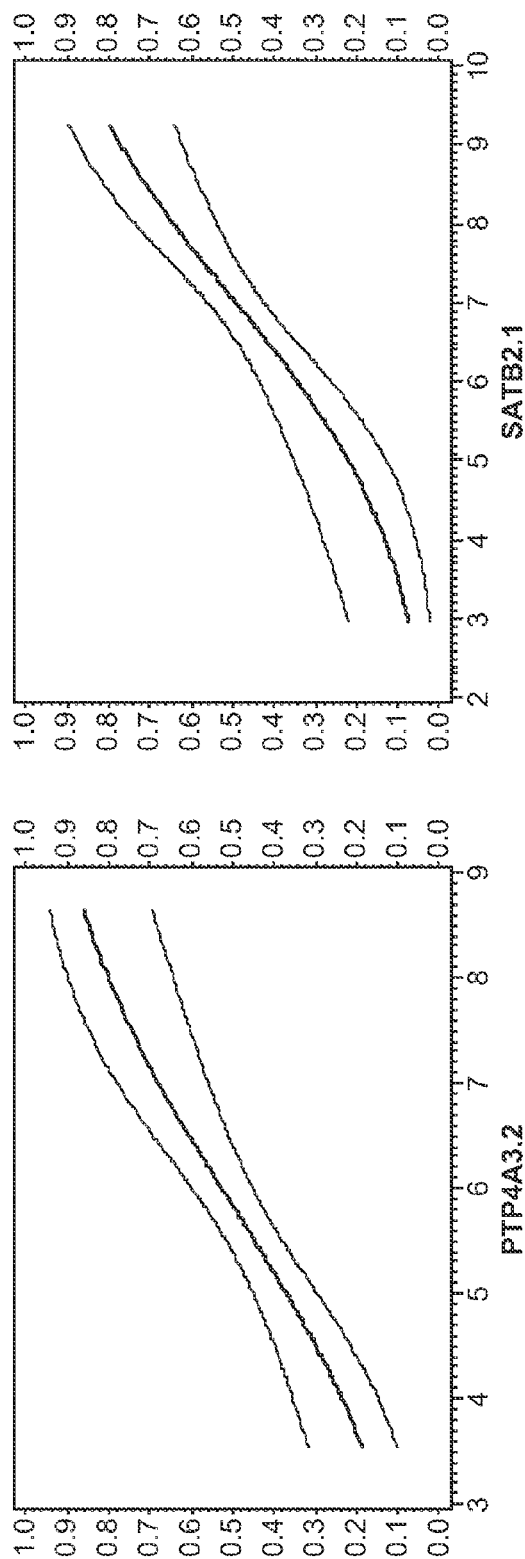
FIG. 7B

SEQUENCE LISTING

```
<160> NUMBER OF SEQ ID NOS: 436

<210> SEQ ID NO 1
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 1
ggcgggatgt ggtaacag                                               18

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
gaagtgccag gaggcgatta                                             20

<210> SEQ ID NO 3
<211> LENGTH: 22
<212> TYPE: DNA
<213> ORGANISM: Artificial Sequence
```

```
<220> FEATURE:
<223> OTHER INFORMATION: Synthetic Oligonucleotide

<400> SEQUENCE: 3
ggacagtcag ttttagggtt gc                                          22

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 4 gccectatcc taccttcaat cc                                          22

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
cggacacatc tggtgacttc                                             20

<210> SEQ ID NO 6
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 6
tgtgagtgaa atgccttcta gtagtga                                     27

<210> SEQ ID NO 7
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 7
ccgctttcgc tacagcat                                               18

<210> SEQ ID NO 8
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 8
ggctcttgtg cgtactgtcc tt                                          22

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
ccattcccac cattctacct                                             20
```

```
<210> SEQ ID NO 10
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 10
cttttgtgga actctatggg aaca                                              24

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 11
gagctccgca aggatgac                                                     18

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 12
gtgagtccac tggggcac                                                     18

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
ccttccgacc agcagatgaa                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
tcagggggct agaaatctgt                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
tcagggggct agaaatctgt                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
```

```
gtgcaggaaa ggttcacaaa                                               20

<210> SEQ ID NO 17
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 17
agggagatgc cgcttcgt                                                 18

<210> SEQ ID NO 18
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 18
tcctcaacag aggtacacat gg                                            22

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
atcctagccc tggttttgg                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
gaaggccaag aaccgagtca                                               20

<210> SEQ ID NO 21
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 21
aaagaagatg atgaccgggt ttac                                          24

<210> SEQ ID NO 22
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 22
atgctgtggc tccttcctaa ct                                            22

<210> SEQ ID NO 23
<211> LENGTH: 18
<212> TYPE: DNA
<213> ORGANISM: Artificial Sequence
```

```
<220> FEATURE:
<223> OTHER INFORMATION: Synthetic Oligonucleotide

<400> SEQUENCE: 23
gcccagtgcg gagaacag                                                  18

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
cgtcaggacc caccatgtct                                                20

<210> SEQ ID NO 25
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 25
atcaccgaca gcacagaca                                                 19

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 26
cacacaaaac agaaccagga ct                                             22

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
ctcataccag ccatccaatg                                                20

<210> SEQ ID NO 28
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 28
aaacgagcag tttgccatca g                                              21

<210> SEQ ID NO 29
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 29
cacagcctca cttctaacct tctg                                           24
```

```
<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
ctgaaggagc tccaagacct                                            20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
gatcgctgag tggggtactg                                            20

<210> SEQ ID NO 32
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 32
ctaactggcc gcaatgct                                              18

<210> SEQ ID NO 33
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 33
accgtatgga cagccacag                                             19

<210> SEQ ID NO 34
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 34
gacatttcca gtcctgcagt ca                                         22

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
atccaacgca cacagtgaat                                            20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
```
tgctcattct tgaggagcat                                           20

<210> SEQ ID NO 37
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 37
ctctgagaca gtgcttcgat gact                                      24

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
agacatcagc tcctggttca                                           20

<210> SEQ ID NO 39
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 39
tggtgacgat ggaggagc                                             18

<210> SEQ ID NO 40
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 40
catgcaggga ctgggatt                                             18

<210> SEQ ID NO 41
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 41
agcctactgc aacacgcc                                             18

<210> SEQ ID NO 42
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 42
ctttgccttg ctctgtcaca gt                                        22

<210> SEQ ID NO 43
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 43
tgtcgatgga cttccagaac                                              20

<210> SEQ ID NO 44
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 44
gctagtactt tgatgctccc ttgat                                        25

<210> SEQ ID NO 45
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 45
cgcctgttca ccaagattga c                                            21

<210> SEQ ID NO 46
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 46
cggttatgtc atgccagata cac                                          23

<210> SEQ ID NO 47
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 47
tggctcttaa tcagtttcgt tacct                                        25

<210> SEQ ID NO 48
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 48
ataacaaagt gtagctctga catgaatg                                     28

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
gtctccagtg gaagggaaaa                                              20
```

```
<210> SEQ ID NO 50
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 50
caagatctcc cgcttccc                                                 18

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
cttatgctcc ctgctctgga                                               20

<210> SEQ ID NO 52
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 52
cgctccagac ctatgatgac t                                             21

<210> SEQ ID NO 53
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 53
tgatgcgcct ggaaacagt                                                19

<210> SEQ ID NO 54
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 54
gcttatgacc gaccccaa                                                 18

<210> SEQ ID NO 55
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 55
gtgtgggcaa ggacaagc                                                 18

<210> SEQ ID NO 56
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 56
```
cgaaaagatg ctgaacagtg aca                                          23

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 57
cccactcagt agccaagtca                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 58
gactccttcg tccccagttg                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
cggtgtgaga agtgcagcaa                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
ccgaaatcca gatgatgatg                                              20

<210> SEQ ID NO 61
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 61
agaaccgcaa ggtgagcaa                                               19

<210> SEQ ID NO 62
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 62
aaggaaccat ctcactgtgt gtaaac                                       26

<210> SEQ ID NO 63
<211> LENGTH: 19
<212> TYPE: DNA
<213> ORGANISM: Artificial Sequence

```
<220> FEATURE:
<223> OTHER INFORMATION: Synthetic Oligonucleotide

<400> SEQUENCE: 63
gtgcccgagc catatagca                                              19

<210> SEQ ID NO 64
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 64
accgggagcc ctacatgac                                              19

<210> SEQ ID NO 65
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 65
ggaggtaagg ccttctgcat                                             20

<210> SEQ ID NO 66
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 66
tgagagccag gcttcttgta                                             20

<210> SEQ ID NO 67
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 67
cgaggattgg ttcttcagca a                                           21

<210> SEQ ID NO 68
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 68
tgagcggcag aatcaggagt a                                           21

<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
cagatgaggc acatggagac                                             20
```

```
<210> SEQ ID NO 70
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 70
actcaagcgg aaattgaagc a                                              21

<210> SEQ ID NO 71
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 71
cagatggcca ctttgagaac att                                            23

<210> SEQ ID NO 72
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 72
cgctcagcca gatgcaatc                                                 19

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
tagttcccag ctgaccatca                                                20

<210> SEQ ID NO 74
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 74
tgctggctac tgggtgttag t                                              21

<210> SEQ ID NO 75
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 75
gcagagctgg cagaggtt                                                  18

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
```
cttaacgtgg gagtggaacc                                              20

<210> SEQ ID NO 77
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 77
gcggaaggtc cctcagaca                                               19

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
actgaaggag acccttggag                                              20

<210> SEQ ID NO 79
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 79
agagccagtt gctgtagaac tcaa                                         24

<210> SEQ ID NO 80
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 80
caagaccagg gctggaac                                                18

<210> SEQ ID NO 81
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 81
gaatgaatgc tgtctgtgtg g                                            21

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
cccatggatg ctcctctgaa                                              20

<210> SEQ ID NO 83
<211> LENGTH: 19
<212> TYPE: DNA
<213> ORGANISM: Artificial Sequence

```
<220> FEATURE:
<223> OTHER INFORMATION: Synthetic Oligonucleotide

<400> SEQUENCE: 83
gcgcaggttc cgaatctat                                          19

<210> SEQ ID NO 84
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 84
gtggcccaat taggcttg                                           18

<210> SEQ ID NO 85
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 85
aatatttgtg cggggtatgg                                         20

<210> SEQ ID NO 86
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 86
cgcttgccta actcatactt tcc                                     23

<210> SEQ ID NO 87
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 87
ggctactctg atctatgttg ataaggaa                                28

<210> SEQ ID NO 88
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 88
tgatttctcc ctcaagctgt t                                       21

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 89
agtgggagac acctgacctt                                         20
```

-continued

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 90
gtaggcctgt acccagacca                                              20

<210> SEQ ID NO 91
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 91
ctggccagtg tggattttc                                               19

<210> SEQ ID NO 92
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 92
gagagagcca gtctgatcca                                              20

<210> SEQ ID NO 93
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 93
taggagattg cttcggcatc                                              20

<210> SEQ ID NO 94
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 94
actgctccgg caggtagat                                               19

<210> SEQ ID NO 95
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 95
ggcagcttcc ttgaaccat                                               19

<210> SEQ ID NO 96
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 96
gatggctcca tgtgcaaag					19

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
gccaactgct ttcatttgtg					20

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 98
ggtgtgccac agaccttcct					20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
aacaccaatg ggttccatct					20

<210> SEQ ID NO 100
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 100
tccctgcggt cccagatag					19

<210> SEQ ID NO 101
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 101
cgactccgtt ctcagtgtct ga					22

<210> SEQ ID NO 102
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 102
gagtcgaccc tgcacctg					18

<210> SEQ ID NO 103
<211> LENGTH: 19
<212> TYPE: DNA
<213> ORGANISM: Artificial Sequence

```
<220> FEATURE:
<223> OTHER INFORMATION: Synthetic Oligonucleotide

<400> SEQUENCE: 103
gtggatgtgc cctgaagga                                               19

<210> SEQ ID NO 104
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 104
caggtgtagc ctgccctct                                               19

<210> SEQ ID NO 105
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 105
ctgctgtctt gggtgcattg                                              20

<210> SEQ ID NO 106
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 106
cctcagcaag acgttatttg aaatt                                        25

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 107
tctgaagcac tctcgcacac                                              20

<210> SEQ ID NO 108
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 108
cccaaggact gagggactct                                              20

<210> SEQ ID NO 109
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 109
gcagttggaa gacacaggaa agt                                          23
```

```
<210> SEQ ID NO 110
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 110
atttctgggc ctccgagt                                                18

<210> SEQ ID NO 111
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 111
cgggcactca ctgctattac c                                            21

<210> SEQ ID NO 112
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 112
gacagcccag agacccac                                                18

<210> SEQ ID NO 113
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 113
cctttaacca ttatggcctt atgc                                         24

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
agagccatcc tctgctcttc                                              20

<210> SEQ ID NO 115
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 115
ttgtggttcg ttatcatact cttctga                                      27

<210> SEQ ID NO 116
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 116
```
tgggagtatc ggatgtagct g                                        21

<210> SEQ ID NO 117
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 117
tcagatgacg aagagcacag atg                                      23

<210> SEQ ID NO 118
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 118
gggaacatag acccaccaat                                          20

<210> SEQ ID NO 119
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 119
cagcggttga agcgttcct                                           19

<210> SEQ ID NO 120
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 120
cttgttgttc accaggacga                                          20

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
ctccgttagg acctggctta                                          20

<210> SEQ ID NO 122
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 122
tttatatgca cattgggagc tgat                                     24

<210> SEQ ID NO 123
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 123
ccattccagt tgatctgtgg                                               20

<210> SEQ ID NO 124
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 124
ccattccagt tgatctgtgg                                               20

<210> SEQ ID NO 125
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 125
gcacacacga tggagtaagg                                               20

<210> SEQ ID NO 126
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 126
ctctcacacc ttgctccaat gta                                           23

<210> SEQ ID NO 127
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 127
atcctagggc ttgtgggc                                                 18

<210> SEQ ID NO 128
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 128
ctgccttctc atctgcacaa                                               20

<210> SEQ ID NO 129
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 129
tccccagtta gttcaaaagt caca                                          24
```

```
<210> SEQ ID NO 130
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 130
gagcctctgg atggtgcaat                                               20

<210> SEQ ID NO 131
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 131
acccaaattg tgatatacaa aaaggtt                                       27

<210> SEQ ID NO 132
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 132
aatcacacgc acctggagaa c                                             21

<210> SEQ ID NO 133
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 133
ggttaattgg tgacatcctc aaga                                          24

<210> SEQ ID NO 134
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 134
acctgtgttt ggatttgcag                                               20

<210> SEQ ID NO 135
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 135
ctgaagtagc acttccggat t                                             21

<210> SEQ ID NO 136
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 136
```
ttgggttgaa gaaatcagtc c                                                       21

<210> SEQ ID NO 137
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 137
gttggtgatg ttccgaagca                                                         20

<210> SEQ ID NO 138
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 138
ttgaatggcg tggattcaat ag                                                      22

<210> SEQ ID NO 139
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 139
caaaaccgct gtgtttcttc                                                         20

<210> SEQ ID NO 140
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 140
cctcaccttc acccttgttc                                                         20

<210> SEQ ID NO 141
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 141
aggtacccgg tggtcagg                                                           18

<210> SEQ ID NO 142
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 142
tgactacagg atcagcgctt c                                                       21

<210> SEQ ID NO 143
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 143
ctccgatcgc acacatttgt                                           20

<210> SEQ ID NO 144
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 144
aaagaagagc gagagcgtgt                                           20

<210> SEQ ID NO 145
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 145
gtggctgcat tagtgtccat                                           20

<210> SEQ ID NO 146
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 146
ccatgaggcc caacttcct                                            19

<210> SEQ ID NO 147
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 147
gacaaacacc cttcctccag                                           20

<210> SEQ ID NO 148
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 148
ctcgtcccgg ttcatcag                                             18

<210> SEQ ID NO 149
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 149
tgctcctacc ctatcatttg g                                         21
```

```
<210> SEQ ID NO 150
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 150
tgggcacccc actacttg                                                 18

<210> SEQ ID NO 151
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 151
aaatacctga cacccttatg acaaatt                                       27

<210> SEQ ID NO 152
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 152
attgggacag cttggatca                                                19

<210> SEQ ID NO 153
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 153
gaacagctgg aggccaagtc                                               20

<210> SEQ ID NO 154
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 154
gtggcgtgcc tcgaagtc                                                 18

<210> SEQ ID NO 155
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 155
gaactgagac ccactgaaga aagg                                          24

<210> SEQ ID NO 156
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 156
```
caaggcatat cgatcctcat aaagt                                          25

<210> SEQ ID NO 157
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 157
cacacctgca gtagttttga ctca                                           24

<210> SEQ ID NO 158
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 158
aggaatgcag ctactcactg g                                              21

<210> SEQ ID NO 159
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 159
gttggagctc atggacgc                                                  18

<210> SEQ ID NO 160
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 160
aattcaagtc cccagccc                                                  18

<210> SEQ ID NO 161
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 161
acagtggaag gaccaggact                                                20

<210> SEQ ID NO 162
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 162
cgaggttgtg aaaggtgctt atc                                            23

<210> SEQ ID NO 163
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 163
aaagttccag gcaacatcgt                                               20

<210> SEQ ID NO 164
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 164
gacctgattt ggcctcacc                                                19

<210> SEQ ID NO 165
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 165
tcaggaacag ccaccagtga                                               20

<210> SEQ ID NO 166
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 166
cacgcaggtg gtatcagtct                                               20

<210> SEQ ID NO 167
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 167
tggcacttga aggctctggt a                                             21

<210> SEQ ID NO 168
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 168
cctctcgcaa gtgctccat                                                19

<210> SEQ ID NO 169
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 169
cccaaggaat gagtggattt                                               20
```

-continued

```
<210> SEQ ID NO 170
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 170
tccaactgaa ggtccctgat g                                              21

<210> SEQ ID NO 171
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 171
atcaggaagg ctgccaagag                                                20

<210> SEQ ID NO 172
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 172
cggtagtggt tgatgactgt tga                                            23

<210> SEQ ID NO 173
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 173
ccttaagctc tttcactgac tcaatct                                        27

<210> SEQ ID NO 174
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 174
cagccgtcag gaacagga                                                  18

<210> SEQ ID NO 175
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 175
atcctggtcc tctttgctgt                                                20

<210> SEQ ID NO 176
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 176
```
actctgcacc agctcactgt tg                                    22

<210> SEQ ID NO 177
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 177
tgcggtaggt ggcaatctc                                        19

<210> SEQ ID NO 178
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 178
ttgaaatggc agaacggtag                                       20

<210> SEQ ID NO 179
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 179
actccctgaa gccgagacac t                                     21

<210> SEQ ID NO 180
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 180
ggcagcatta accacaagga tt                                    22

<210> SEQ ID NO 181
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 181
gcactgagat cttcctattg gtgaa                                 25

<210> SEQ ID NO 182
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 182
cagccttgtt ctcagcaatg                                       20

<210> SEQ ID NO 183
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 183
gacaaccagg gacacagtca                                          20

<210> SEQ ID NO 184
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 184
ggtcgctcac caggtcat                                            18

<210> SEQ ID NO 185
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 185
gtgaagcctc ccatttcttg                                          20

<210> SEQ ID NO 186
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 186
tctaagtttc ccgaggtttc tca                                      23

<210> SEQ ID NO 187
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 187
taaataaccc tgcccacaca                                          20

<210> SEQ ID NO 188
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 188
ctgggcctac acagtccttc a                                        21

<210> SEQ ID NO 189
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 189
ggatggcctg acgattctt                                           19
```

-continued

```
<210> SEQ ID NO 190
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 190
atgccatatc gggtcctgt                                                    19

<210> SEQ ID NO 191
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 191
ccggtggcta ccagacattg                                                   20

<210> SEQ ID NO 192
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 192
gggcctgtaa tgggatcag                                                    19

<210> SEQ ID NO 193
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 193
tcacaggtgc cagcaaag                                                     18

<210> SEQ ID NO 194
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 194
aacgagatcc ctgtgcttgt                                                   20

<210> SEQ ID NO 195
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 195
ccattcagac tgcgccactt                                                   20

<210> SEQ ID NO 196
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 196
```
gcttcagccc atccttagca                                          20

<210> SEQ ID NO 197
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 197
ttccggttta ggactagtgg a                                        21

<210> SEQ ID NO 198
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 198
tgatctgggc attgtactcc                                          20

<210> SEQ ID NO 199
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 199
gtgtttgggg agatccagc                                           19

<210> SEQ ID NO 200
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 200
ctttgaccca ctggtttatg g                                        21

<210> SEQ ID NO 201
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 201
aggctgccat gtcctcata                                           19

<210> SEQ ID NO 202
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 202
gaatagacgc tggcaactga                                          20

<210> SEQ ID NO 203
<211> LENGTH: 18
<212> TYPE: DNA
<213> ORGANISM: Artificial Sequence

```
<220> FEATURE:
<223> OTHER INFORMATION: Synthetic Oligonucleotide

<400> SEQUENCE: 203
atgccttgtc gggatgtc                                              18

<210> SEQ ID NO 204
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 204
gcagttggtc aggaggtctt                                            20

<210> SEQ ID NO 205
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 205
ggtgtggcac tctggcat                                              18

<210> SEQ ID NO 206
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 206
actcaggccc atttcctttta                                           20

<210> SEQ ID NO 207
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 207
acggagttct tgacagagtt ttga                                       24

<210> SEQ ID NO 208
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 208
cctcttcatc aggccaaact                                            20

<210> SEQ ID NO 209
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 209
gtgggaacag ggtggacact                                            20
```

-continued

```
<210> SEQ ID NO 210
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 210
ccctccatgc ccactttct                                                    19

<210> SEQ ID NO 211
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 211
gcgaatgcca tgactgaa                                                     18

<210> SEQ ID NO 212
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 212
ctgcggatcc agggtaagaa                                                   20

<210> SEQ ID NO 213
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 213
gggatgtgtc cactgaacct                                                   20

<210> SEQ ID NO 214
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 214
gcagcctggg accacttg                                                     18

<210> SEQ ID NO 215
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 215
aagtgtgatt ggcaaaactg attg                                              24

<210> SEQ ID NO 216
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 216
```

```
cactgtgctc tctgccagc                                                  19

<210> SEQ ID NO 217
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 217
agacctagca ttcgctggtg                                                 20

<210> SEQ ID NO 218
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 218
tgcgtggcac tattttcaag a                                               21

<210> SEQ ID NO 219
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 219
tcagccacaa tcaccaactc caca                                            24

<210> SEQ ID NO 220
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 220
tgctacttgc aaaggcgtgt cctactgc                                        28

<210> SEQ ID NO 221
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 221
cagtaactcg gggcctgttt ccc                                             23

<210> SEQ ID NO 222
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 222
tcctcggatg tcgctgcct                                                  19

<210> SEQ ID NO 223
<211> LENGTH: 23
<212> TYPE: DNA
<213> ORGANISM: Artificial Sequence
```

```
<220> FEATURE:
<223> OTHER INFORMATION: Synthetic Oligonucleotide

<400> SEQUENCE: 223
taccctttgc cagggcaacc atc                                              23

<210> SEQ ID NO 224
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 224
ccgtcctcgg gagccgacta tga                                              23

<210> SEQ ID NO 225
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 225
tccagcctgt ctccagtagg ccac                                             24

<210> SEQ ID NO 226
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 226
aggctcagtg atgtcttccc tgtcaccag                                        29

<210> SEQ ID NO 227
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 227
acaccccaga cgtcctggcc t                                                21

<210> SEQ ID NO 228
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 228
ttcggctctc ggctgctgca                                                  20

<210> SEQ ID NO 229
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 229
caagggtctc cagcacctct acgc                                             24
```

```
<210> SEQ ID NO 230
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 230
cgtctaagcc acaagccgag cac                                              23

<210> SEQ ID NO 231
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 231
caatttgggc aacgagaccg atcct                                            25

<210> SEQ ID NO 232
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 232
ctatgggccc ttcaccaaca tgc                                              23

<210> SEQ ID NO 233
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 233
ctatgggccc ttcaccaaca tgc                                              23

<210> SEQ ID NO 234
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 234
agtgtctgcg tccaatacac gcgt                                             24

<210> SEQ ID NO 235
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 235
ccttcatcac agacacagga gggcg                                            25

<210> SEQ ID NO 236
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 236
```
acacccgatg agagtatcct gggc                                              24

<210> SEQ ID NO 237
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 237
tttgctgtca ccagcgtcgc                                                   20

<210> SEQ ID NO 238
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 238
ttatattcca gtttaaggcc aatcctc                                           27

<210> SEQ ID NO 239
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 239
caaactcaac gtgcaagcct cgga                                              24

<210> SEQ ID NO 240
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 240
taccaagcaa cctacatgtc aagaaagccc                                        30

<210> SEQ ID NO 241
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 241
ccagcttgat tctcgtctct gcacttaagc                                        30

<210> SEQ ID NO 242
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 242
cgcggccgag acatggcttg                                                   20

<210> SEQ ID NO 243
<211> LENGTH: 27
<212> TYPE: DNA
<213> ORGANISM: Artificial Sequence

```
<220> FEATURE:
<223> OTHER INFORMATION: Synthetic Oligonucleotide

<400> SEQUENCE: 243
ccctgctacc aatatggact ccagtca                                              27

<210> SEQ ID NO 244
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 244
acccagtgga acccaagcca ttc                                                  23

<210> SEQ ID NO 245
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 245
caccaagccc agaggacagt tcct                                                 24

<210> SEQ ID NO 246
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 246
cctcaccggc atagactgga agcg                                                 24

<210> SEQ ID NO 247
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 247
acccacccac cactgccaag ctc                                                  23

<210> SEQ ID NO 248
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 248
tgctgatgtg ccctctcctt gg                                                   22

<210> SEQ ID NO 249
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 249
ctcatagaca tgcgccacct ccac                                                 24
```

```
<210> SEQ ID NO 250
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 250
tctgctgttt gctaccatgg gcac                                            24

<210> SEQ ID NO 251
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 251
tctcacatgc tgtacccaaa gcca                                            24

<210> SEQ ID NO 252
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 252
tgcctctctg ccccaccctt tgt                                             23

<210> SEQ ID NO 253
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 253
tcagccacca gaacctcaac ctca                                            24

<210> SEQ ID NO 254
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 254
cagcacccct tggcagtttc gaaat                                           24

<210> SEQ ID NO 255
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 255
cagacttggt gccctttgac tcc                                             23

<210> SEQ ID NO 256
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 256
```
cgaggccatt gacttcatag actcca 26

<210> SEQ ID NO 257
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 257
ttgagcacac tgcagtccat ctcc 24

<210> SEQ ID NO 258
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 258
tctaccctat gcgcctggaa gtcc 24

<210> SEQ ID NO 259
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 259
ttcactacct gttcgtacgg gggc 24

<210> SEQ ID NO 260
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 260
agagtttaac agccctgctc tggctgactt 30

<210> SEQ ID NO 261
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 261
cacctgggca gctgccaa 18

<210> SEQ ID NO 262
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 262
ccagagagcc tccctgcagc ca 22

<210> SEQ ID NO 263
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 263
tgcgcccgat gagatcaccg                                                    20

<210> SEQ ID NO 264
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 264
cctcaaaggt actccctcct cccgg                                              25

<210> SEQ ID NO 265
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 265
tgtcccacga ataatgcgta aattctccag                                         30

<210> SEQ ID NO 266
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 266
ttgtttgcat ggacagtgca tctatctggt                                         30

<210> SEQ ID NO 267
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 267
cccatgatct tcaagcaggg aagc                                               24

<210> SEQ ID NO 268
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 268
actccaggga cacctgtcgc ttg                                                23

<210> SEQ ID NO 269
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 269
caccagcggg ctatctgcgt ttat                                               24
```

```
<210> SEQ ID NO 270
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 270
tgttagccaa agactgccac tgca                                              24

<210> SEQ ID NO 271
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 271
agcaggcaac tccgaaggac aacg                                              24

<210> SEQ ID NO 272
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 272
ctcatcacct ggtctccggt gtgt                                              24

<210> SEQ ID NO 273
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 273
tccaccctcc ctttctcact ccac                                              24

<210> SEQ ID NO 274
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 274
cttcctcctc ccttctggtc agttggat                                          28

<210> SEQ ID NO 275
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 275
tcaagtaaac gggctgtttt ccaaaca                                           27

<210> SEQ ID NO 276
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 276
```
ttgggcctcc cataattgct ttgcc                                        25

<210> SEQ ID NO 277
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 277
ccagaccata gcacactcgg gcac                                         24

<210> SEQ ID NO 278
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 278
ctcatggacc ctggtgctac acg                                          23

<210> SEQ ID NO 279
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 279
tggagattct ccagcacgtc atcgac                                       26

<210> SEQ ID NO 280
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 280
tgacttccaa gctggccgtg gc                                           22

<210> SEQ ID NO 281
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 281
acgtccgggt cctcactgtc cttcc                                        25

<210> SEQ ID NO 282
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 282
aaatacctgc aaccgttact gccgtgac                                     28

<210> SEQ ID NO 283
<211> LENGTH: 24
<212> TYPE: DNA
<213> ORGANISM: Artificial Sequence

```
<220> FEATURE:
<223> OTHER INFORMATION: Synthetic Oligonucleotide

<400> SEQUENCE: 283
ctccgtcatt ggcattccct tcac                                  24

<210> SEQ ID NO 284
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 284
tgtctcaaaa tgccagcctt ctgaa                                 25

<210> SEQ ID NO 285
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 285
cacctcgcgg ttcagttcct ctgt                                  24

<210> SEQ ID NO 286
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 286
ctcatggaca tcaagtcgcg gctg                                  24

<210> SEQ ID NO 287
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 287
ctgattcctc aggtccttgg cctg                                  24

<210> SEQ ID NO 288
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 288
aggtcttatc agcacagtct ccgcctcc                              28

<210> SEQ ID NO 289
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 289
agctgacaac agtgtgaacg accagacc                              28
```

```
<210> SEQ ID NO 290
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 290
tgccccagtc acctgctgtt a                                              21

<210> SEQ ID NO 291
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 291
ctcagcctcg tcgttcttat ccacc                                          25

<210> SEQ ID NO 292
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 292
tgcagtcctg tgtgcttccc tctc                                           24

<210> SEQ ID NO 293
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 293
caactgacca agctgctgga ctcc                                           24

<210> SEQ ID NO 294
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 294
catgagcctg ctcagctctg cata                                           24

<210> SEQ ID NO 295
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 295
ccccgattga aagaaccaga gaggct                                         26

<210> SEQ ID NO 296
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 296
```
tctcctgccg atgcccctag g                                    21

<210> SEQ ID NO 297
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 297
tctctgctgg gcaaggatgt tctgttc                              27

<210> SEQ ID NO 298
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 298
tactgcacca tctgcagcgt gatc                                 24

<210> SEQ ID NO 299
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 299
acaagcgtcg caatgaggac tctc                                 24

<210> SEQ ID NO 300
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 300
cattgactgc cgaggcccca tg                                   22

<210> SEQ ID NO 301
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 301
aaccattctg cactggagtc gctg                                 24

<210> SEQ ID NO 302
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 302
ttctccatct ggcctcagag caga                                 24

<210> SEQ ID NO 303
<211> LENGTH: 29
<212> TYPE: DNA
<213> ORGANISM: Artificial Sequence

```
<220> FEATURE:
<223> OTHER INFORMATION: Synthetic Oligonucleotide

<400> SEQUENCE: 303
ccaagagaaa cgagatttaa aaacccacc                                29

<210> SEQ ID NO 304
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 304
tccacgcagc gtggcactg                                           19

<210> SEQ ID NO 305
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 305
cacacgggtg cctggttctc ca                                       22

<210> SEQ ID NO 306
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 306
cactggagcc acctctttgg ca                                       22

<210> SEQ ID NO 307
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 307
ttgatcttct gctcaatctc agcttgaga                                29

<210> SEQ ID NO 308
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 308
aagccatcca cactctttcg gctc                                     24

<210> SEQ ID NO 309
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 309
ttccttgcat cttcagaggc atgc                                     24
```

```
<210> SEQ ID NO 310
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 310
ctgctctgcc agcttggcct tc                                              22

<210> SEQ ID NO 311
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 311
aaggccactg caaatgcaac catt                                            24

<210> SEQ ID NO 312
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 312
cgggatcctc ccttcgtacc agtt                                            24

<210> SEQ ID NO 313
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 313
tggtgacctg ctcatagcca gcat                                            24

<210> SEQ ID NO 314
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 314
atgcgcttct ctgcctgtga tgtc                                            24

<210> SEQ ID NO 315
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 315
agggatctga accaatacag agcagaca                                        28

<210> SEQ ID NO 316
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 316
```
ttggcctgta atcacctgtg cagcctt                                27

<210> SEQ ID NO 317
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 317
ttctgggctc ctgattgctc aagc                                   24

<210> SEQ ID NO 318
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 318
atcctgcccg gagtggaact gaagc                                  25

<210> SEQ ID NO 319
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 319
atcttgagtc ccctggagga aagc                                   24

<210> SEQ ID NO 320
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 320
aattaacagc cacccctcag gcg                                    23

<210> SEQ ID NO 321
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 321
aagccaggcg tctacacgag agtctcac                               28

<210> SEQ ID NO 322
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 322
atcaatccgt ctgggtgcca gaac                                   24

<210> SEQ ID NO 323
<211> LENGTH: 25
<212> TYPE: DNA
<213> ORGANISM: Artificial Sequence

```
<220> FEATURE:
<223> OTHER INFORMATION: Synthetic Oligonucleotide

<400> SEQUENCE: 323
ttgccttgct gctctacctc cacca                                          25

<210> SEQ ID NO 324
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 324
cctctctctc aaggccccaa accagt                                         26

<210> SEQ ID NO 325
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 325
cagtgattcc ctcctcccgt cact                                           24

<210> SEQ ID NO 326
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 326
tgccttctca tttcccagag gctt                                           24

<210> SEQ ID NO 327
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 327
tccccaaatt gcagatttat caacggc                                        27

<210> SEQ ID NO 328
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 328
ggcgggatgt ggtaacagag accaagactg tggagttggt gattgtggct gatcactcgg    60
aggcccagaa at                                                        72

<210> SEQ ID NO 329
<211> LENGTH: 73
<212> TYPE: DNA
<213> ORGANISM: Artificial Sequence
<220> FEATURE:
<223> OTHER INFORMATION: Synthetic Oligonucleotide

<400> SEQUENCE: 329
gaagtgccag gaggcgatta atgctacttg caaaggcgtg tcctactgca caggtaatag    60
```

```
cagtgagtgc ccg                                                          73

<210> SEQ ID NO 330
<211> LENGTH: 71
<212> TYPE: DNA
<213> ORGANISM: Artificial Sequence
<220> FEATURE:
<223> OTHER INFORMATION: Synthetic Oligonucleotide

<400> SEQUENCE: 330
ggacagtcag ttttagggtt gcctgtatcc agtaactcgg ggcctgtttc cccgtgggtc      60
tctgggctgt c                                                           71

<210> SEQ ID NO 331
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 331
gcccctatcc taccttcaat ccatcctcgg atgtcgctgc cttgcataag gccataatgg      60
ttaaagg                                                                67

<210> SEQ ID NO 332
<211> LENGTH: 71
<212> TYPE: DNA
<213> ORGANISM: Artificial Sequence
<220> FEATURE:
<223> OTHER INFORMATION: Synthetic Oligonucleotide

<400> SEQUENCE: 332
cggacacatc tggtgacttc cgcaagctga tggttgccct ggcaaagggt agaagagcag      60
aggatggctc t                                                           71

<210> SEQ ID NO 333
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 333
tgtgagtgaa atgccttcta gtagtgaacc gtcctcggga gccgactatg actactcaga      60
agagtatgat aacgaaccac aa                                               82

<210> SEQ ID NO 334
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 334
ccgctttcgc tacagcatgg tggcctactg gagacaggct ggactcagct acatccgata      60
ctccca                                                                 66

<210> SEQ ID NO 335
<211> LENGTH: 80
<212> TYPE: DNA
<213> ORGANISM: Artificial Sequence
<220> FEATURE:
<223> OTHER INFORMATION: Synthetic Oligonucleotide
```

<400> SEQUENCE: 335
ggctcttgtg cgtactgtcc ttcgggctgg tgacagggaa gacatcactg agcctgccat        60
ctgtgctctt cgtcatctga                                                   80

<210> SEQ ID NO 336
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 336
ccattcccac cattctacct gaggccagga cgtctggggt gtggggattg gtgggtctat        60
gttccc                                                                  66

<210> SEQ ID NO 337
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 337
cttttgtgga actctatggg aacaatgcag cagccgagag ccgaaagggc caggaacgct        60
tcaaccgctg                                                              70

<210> SEQ ID NO 338
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 338
gagctccgca aggatgactt caagggtctc cagcacctct acgccctcgt cctggtgaac        60
aacaag                                                                  66

<210> SEQ ID NO 339
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 339
gtgagtccac tggggcacgg cagcgtctaa gccacaagcc gagcacataa gccaggtcct        60
aacggag                                                                 67

<210> SEQ ID NO 340
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 340
ccttccgacc agcagatgaa gatcatcgaa atcaatttgg gcaacgagac cgatcctcat        60
cagctcccaa tgtgcatata aa                                                82

<210> SEQ ID NO 341
<211> LENGTH: 65

```
<212> TYPE: DNA
<213> ORGANISM: Artificial Sequence
<220> FEATURE:
<223> OTHER INFORMATION: Synthetic Oligonucleotide

<400> SEQUENCE: 341 tcaggggct agaaatctgt tgctatgggc ccttcaccaa catgcccaca gatcaactgg    60
aatgg                                                              65

<210> SEQ ID NO 342
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 342 tcaggggct agaaatctgt tgctatgggc ccttcaccaa catgcccaca gatcaactgg    60
aatgg                                                              65

<210> SEQ ID NO 343
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 343
gtgcaggaaa ggttcacaaa tgtggagtgt ctgcgtccaa tacacgcgtg tgctcctctc    60
cttactccat cgtgtgtgc                                                79

<210> SEQ ID NO 344
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 344
agggagatgc cgcttcgtgg tggccgagca gacgccctcc tgtgtctgtg atgaaggcta    60
cattggagca aggtgtgaga g                                             81

<210> SEQ ID NO 345
<211> LENGTH: 71
<212> TYPE: DNA
<213> ORGANISM: Artificial Sequence
<220> FEATURE:
<223> OTHER INFORMATION: Synthetic Oligonucleotide

<400> SEQUENCE: 345
tcctcaacag aggtacacat ggtccgccca ggatactctc atcgggtgtc tctgcccaca    60
agccctagga t                                                       71

<210> SEQ ID NO 346
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 346
atcctagccc tggtttttgg cctcctttt gctgtcacca gcgtcgcgtt ccttgtgcag    60
atgagaaggc ag                                                      72
```

-continued

<210> SEQ ID NO 347
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 347
gaaggccaag aaccgagtca aattatattc cagtttaagg ccaatcctcc tgctgtgact    60
tttgaactaa ctgggga                                                   77

<210> SEQ ID NO 348
<211> LENGTH: 71
<212> TYPE: DNA
<213> ORGANISM: Artificial Sequence
<220> FEATURE:
<223> OTHER INFORMATION: Synthetic Oligonucleotide

<400> SEQUENCE: 348
aaagaagatg atgaccgggt ttacccaaac tcaacgtgca agcctcggat tattgcacca    60
tccagaggct c                                                         71

<210> SEQ ID NO 349
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 349
atgctgtggc tccttcctaa ctggggcttt cttgacatgt aggttgcttg gtaataacct    60
ttttgtatat cacaatttgg gt                                             82

<210> SEQ ID NO 350
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 350
gcccagtgcg gagaacaggt ccagcttgat tctcgtctct gcacttaagc tgttctccag    60
gtgcgtgtga tt                                                        72

<210> SEQ ID NO 351
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 351
cgtcaggacc caccatgtct gccccatcac gcggccgaga catggcttgg ccacagctct    60
tgaggatgtc accaattaac c                                              81

<210> SEQ ID NO 352
<211> LENGTH: 90
<212> TYPE: DNA
<213> ORGANISM: Artificial Sequence
<220> FEATURE:
<223> OTHER INFORMATION: Synthetic Oligonucleotide

<400> SEQUENCE: 352

```
atcaccgaca gcacagacag aatccctgct accaatatgg actccagtca tagtacaacg      60
cttcagccta ctgcaaatcc aaacacaggt                                       90
```

<210> SEQ ID NO 353
<211> LENGTH: 69
<212> TYPE: DNA
<213> ORGANISM: Artificial Sequence
<220> FEATURE:
<223> OTHER INFORMATION: Synthetic Oligonucleotide

<400> SEQUENCE: 353

```
cacacaaaac agaaccagga ctggacccag tggaacccaa gccattcaaa tccggaagtg      60
ctacttcag                                                              69
```

<210> SEQ ID NO 354
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 354

```
ctcataccag ccatccaatg caaggaagga caacaccaag cccagaggac agttcctgga      60
ctgatttctt caacccaa                                                    78
```

<210> SEQ ID NO 355
<211> LENGTH: 85
<212> TYPE: DNA
<213> ORGANISM: Artificial Sequence
<220> FEATURE:
<223> OTHER INFORMATION: Synthetic Oligonucleotide

<400> SEQUENCE: 355

```
aaacgagcag tttgccatca gacgcttcca gtctatgccg gtgaggctgc tgggccacag      60
ccccgtgctt cggaacatca ccaac                                            85
```

<210> SEQ ID NO 356
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 356

```
cacagcctca cttctaacct tctggaaccc acccaccact gccaagctca ctattgaatc      60
cacgccattc aa                                                          72
```

<210> SEQ ID NO 357
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 357

```
ctgaaggagc tccaagacct cgctctccaa ggcgccaagg agagggcaca tcagcagaag      60
aaacacagcg gttttg                                                      76
```

<210> SEQ ID NO 358
<211> LENGTH: 71
<212> TYPE: DNA
<213> ORGANISM: Artificial Sequence

```
<220> FEATURE:
<223> OTHER INFORMATION: Synthetic Oligonucleotide

<400> SEQUENCE: 358
gatcgctgag tggggtactg tgtctcatag acatgcgcca cctccacgtg agaacaaggg    60
tgaaggtgag g                                                         71

<210> SEQ ID NO 359
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 359
ctaactggcc gcaatgcttc tctgctgttt gctaccatgg gcaccagtgt cctgaccacc    60
gggtacct                                                             68

<210> SEQ ID NO 360
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 360
accgtatgga cagccacagc ctggctttgg gtacagcatg tgagatgaag cgctgatcct    60
gtagtca                                                              67

<210> SEQ ID NO 361
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 361
gacatttcca gtcctgcagt caatgcctct ctgccccacc ctttgttcag tgtggctggt    60
gccacgacaa atgtgtgcga tcggag                                         86

<210> SEQ ID NO 362
<211> LENGTH: 64
<212> TYPE: DNA
<213> ORGANISM: Artificial Sequence
<220> FEATURE:
<223> OTHER INFORMATION: Synthetic Oligonucleotide

<400> SEQUENCE: 362
atccaacgca cacagtgaat tcagccacca gaacctcaac ctcaacacgc tctcgctctt    60
cttt                                                                 64

<210> SEQ ID NO 363
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 363
tgctcattct tgaggagcat taaggtattt cgaaactgcc aagggtgctg gtgcggatgg    60
acactaatgc agccac                                                    76
```

<210> SEQ ID NO 364
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 364
ctctgagaca gtgcttcgat gactttgcag acttggtgcc ctttgactcc tgggagccgc    60
tcatgaggaa gttgggcctc atgg                                          84

<210> SEQ ID NO 365
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 365
agacatcagc tcctggttca acgaggccat tgacttcata gactccatca agaatgctgg    60
aggaagggtg tttgtc                                                   76

<210> SEQ ID NO 366
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 366
tggtgacgat ggaggagctg cgggagatgg actgcagtgt gctcaaaagg ctgatgaacc    60
gggacgag                                                            68

<210> SEQ ID NO 367
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 367
catgcaggga ctgggattcg aggacttcca ggcgcatagg gtagaaccaa atgatagggt    60
aggagca                                                             67

<210> SEQ ID NO 368
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 368
agcctactgc aacacgcctc cgcccccgta cgaacaggta gtgaaggcca agtagtgggg    60
tgccca                                                              66

<210> SEQ ID NO 369
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 369
ctttgccttg ctctgtcaca gtgaagtcag ccagagcagg gctgttaaac tctgtgaaat    60

```
ttgtcataag ggtgtcaggt attt                                            84

<210> SEQ ID NO 370
<211> LENGTH: 62
<212> TYPE: DNA
<213> ORGANISM: Artificial Sequence
<220> FEATURE:
<223> OTHER INFORMATION: Synthetic Oligonucleotide

<400> SEQUENCE: 370
tgtcgatgga cttccagaac cacctgggca gctgccaaaa gtgtgatcca agctgtccca    60
at                                                                    62

<210> SEQ ID NO 371
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 371
gctagtactt tgatgctccc ttgatggggt ccagagagcc tccctgcagc caccagactt    60
ggcctccagc tgttc                                                      75

<210> SEQ ID NO 372
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 372
cgcctgttca ccaagattga caccattgcg cccgatgaga tcaccgtcag cagcgacttc    60
gaggcacgcc ac                                                         72

<210> SEQ ID NO 373
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 373
cggttatgtc atgccagata cacacctcaa aggtactccc tcctcccggg aaggcaccct    60
ttcttcagtg ggtctcagtt c                                               81

<210> SEQ ID NO 374
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 374
tggctcttaa tcagtttcgt tacctgcctc tggagaattt acgcattatt cgtgggacaa    60
aactttatga ggatcgatat gccttg                                          86

<210> SEQ ID NO 375
<211> LENGTH: 91
<212> TYPE: DNA
<213> ORGANISM: Artificial Sequence
<220> FEATURE:
<223> OTHER INFORMATION: Synthetic Oligonucleotide
```

<400> SEQUENCE: 375
ataacaaagt gtagctctga catgaatggc tattgtttgc atggacagtg catctatctg    60
gtggacatga gtcaaaacta ctgcaggtgt g    91

<210> SEQ ID NO 376
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 376
gtctccagtg aagggaaaa gcccatgatc ttcaagcagg aagcccag tgagtagctg    60 cattcct    67

<210> SEQ ID NO 377
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 377
caagatctcc cgcttcccgc tcaagcgaca ggtgtccctg agtccaacg cgtccatgag    60 ctccaac    67

<210> SEQ ID NO 378
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 378
cttatgctcc ctgctctgga atccaccagc gggctatctg cgtttatggg gctggggact    60
tgaatt    66

<210> SEQ ID NO 379
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 379
cgctccagac ctatgatgac ttgttagcca aagactgcca ctgcatatga gcagtcctgg    60
tccttccact gt    72

<210> SEQ ID NO 380
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 380
tgatgcgcct ggaaacagtc agcaggcaac tccgaaggac aacgagataa gcacctttca    60
caacctcg    68

<210> SEQ ID NO 381
<211> LENGTH: 67

```
<212> TYPE: DNA
<213> ORGANISM: Artificial Sequence
<220> FEATURE:
<223> OTHER INFORMATION: Synthetic Oligonucleotide

<400> SEQUENCE: 381
gcttatgacc gaccccaagc tcatcacctg gtctccggtg tgtcgcaacg atgttgcctg      60
gaacttt                                                                67

<210> SEQ ID NO 382
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 382
gtgtgggcaa ggacaagcag gatagtggag tgagaaaggg agggtggagg gtgaggccaa      60
atcaggtc                                                               68

<210> SEQ ID NO 383
<211> LENGTH: 73
<212> TYPE: DNA
<213> ORGANISM: Artificial Sequence
<220> FEATURE:
<223> OTHER INFORMATION: Synthetic Oligonucleotide

<400> SEQUENCE: 383
cgaaaagatg ctgaacagtg acaaatccaa ctgaccagaa gggaggagga agctcactgg      60
tggctgttcc tga                                                         73

<210> SEQ ID NO 384
<211> LENGTH: 73
<212> TYPE: DNA
<213> ORGANISM: Artificial Sequence
<220> FEATURE:
<223> OTHER INFORMATION: Synthetic Oligonucleotide

<400> SEQUENCE: 384
cccactcagt agccaagtca caatgtttgg aaaacagccc gtttacttga gcaagactga      60
taccacctgc gtg                                                         73

<210> SEQ ID NO 385
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 385
gactccttcg tccccagttg ccgtctagga ttgggcctcc cataattgct tgccaaaat       60 accagagcct tcaagtgcca                                                  80

<210> SEQ ID NO 386
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 386
cggtgtgaga agtgcagcaa gccctgtgcc cgagtgtgct atggtctggg catggagcac      60
ttgcgagagg                                                             70
```

<210> SEQ ID NO 387
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 387
ccgaaatcca gatgatgatg ctcatggacc ctggtgctac acgggaaatc cactcattcc    60
ttggg    65

<210> SEQ ID NO 388
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 388
agaaccgcaa ggtgagcaag gtggagattc tccagcacgt catcgactac atcagggacc    60
ttcagttgga    70

<210> SEQ ID NO 389
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 389
aaggaaccat ctcactgtgt gtaaacatga cttccaagct ggccgtggct ctcttggcag    60
ccttcctgat    70

<210> SEQ ID NO 390
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 390
gtgcccgagc catatagcag gcacgtccgg gtcctcactg tccttccact caacagtcat    60
caaccactac cg    72

<210> SEQ ID NO 391
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 391
accgggagcc ctacatgacc gaaaatacct gcaaccgtta ctgccgtgac gagattgagt    60
cagtgaaaga gcttaagg    78

<210> SEQ ID NO 392
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 392
ggaggtaagg ccttctgcat catctactcc gtcattggca ttcccttcac cctcctgttc    60
ctgacggctg                                                            70

<210> SEQ ID NO 393
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 393
tgagagccag gcttcttgta tgtctcaaaa tgccagcctt ctgaaagtat acagcaaaga    60
ggaccaggat                                                            70

<210> SEQ ID NO 394
<211> LENGTH: 73
<212> TYPE: DNA
<213> ORGANISM: Artificial Sequence
<220> FEATURE:
<223> OTHER INFORMATION: Synthetic Oligonucleotide

<400> SEQUENCE: 394
cgaggattgg ttcttcagca agacagagga actgaaccgc gaggtggcca ccaacagtga    60
gctggtgcag agt                                                        73

<210> SEQ ID NO 395
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 395
tgagcggcag aatcaggagt accagcggct catggacatc aagtcgcggc tggagcagga    60
gattgccacc taccgca                                                    77

<210> SEQ ID NO 396
<211> LENGTH: 73
<212> TYPE: DNA
<213> ORGANISM: Artificial Sequence
<220> FEATURE:
<223> OTHER INFORMATION: Synthetic Oligonucleotide

<400> SEQUENCE: 396
cagatgaggc acatggagac ccaggccaag gacctgagga atcagttgct caactaccgt    60
tctgccattt caa                                                        73

<210> SEQ ID NO 397
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 397
actcaagcgg aaattgaagc agataggtct tatcagcaca gtctccgcct cctggattca    60
gtgtctcggc ttcagggagt                                                 80

<210> SEQ ID NO 398
<211> LENGTH: 77
<212> TYPE: DNA
<213> ORGANISM: Artificial Sequence

```
<220> FEATURE:
<223> OTHER INFORMATION: Synthetic Oligonucleotide

<400> SEQUENCE: 398
cagatggcca ctttgagaac attttagctg acaacagtgt gaacgaccag accaaaatcc    60
ttgtggttaa tgctgcc                                                   77

<210> SEQ ID NO 399
<211> LENGTH: 71
<212> TYPE: DNA
<213> ORGANISM: Artificial Sequence
<220> FEATURE:
<223> OTHER INFORMATION: Synthetic Oligonucleotide

<400> SEQUENCE: 399
cgctcagcca gatgcaatca atgccccagt cacctgctgt tataacttca ccaataggaa    60
gatctcagtg c                                                         71

<210> SEQ ID NO 400
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 400
tagttcccag ctgaccatca aaaggtgga taagaacgac gaggctgagt acatctgcat     60
tgctgagaac aaggctg                                                   77

<210> SEQ ID NO 401
<211> LENGTH: 69
<212> TYPE: DNA
<213> ORGANISM: Artificial Sequence
<220> FEATURE:
<223> OTHER INFORMATION: Synthetic Oligonucleotide

<400> SEQUENCE: 401
tgctggctac tgggtgttag tttgcagtcc tgtgtgcttc cctctcttat gactgtgtcc    60
ctggttgtc                                                            69

<210> SEQ ID NO 402
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 402
gcagagctgg cagaggttct accaactgac caagctgctg gactccatgc atgacctggt    60
gagcgacc                                                             68

<210> SEQ ID NO 403
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 403
cttaacgtgg gagtggaacc acatgagcct gctcagctct gcataagtaa ttcaagaaat    60
gggaggcttc ac                                                        72
```

```
<210> SEQ ID NO 404
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 404
gcggaaggtc cctcagacat ccccgattga aagaaccaga gaggctctga gaaacctcgg    60
gaaacttaga                                                           70

<210> SEQ ID NO 405
<211> LENGTH: 62
<212> TYPE: DNA
<213> ORGANISM: Artificial Sequence
<220> FEATURE:
<223> OTHER INFORMATION: Synthetic Oligonucleotide

<400> SEQUENCE: 405
actgaaggag acccttggag cctaggggca tcggcaggag agtgtgtggg cagggttatt    60
ta                                                                   62

<210> SEQ ID NO 406
<211> LENGTH: 74
<212> TYPE: DNA
<213> ORGANISM: Artificial Sequence
<220> FEATURE:
<223> OTHER INFORMATION: Synthetic Oligonucleotide

<400> SEQUENCE: 406
agagccagtt gctgtagaac tcaaatctct gctgggcaag gatgttctgt tcttgaagga    60
ctgtgtaggc ccag                                                      74

<210> SEQ ID NO 407
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 407
caagaccagg gctggaacgc cgagatcacg ctgcagatgg tgcagtacaa gaatcgtcag    60
gccatcc                                                              67

<210> SEQ ID NO 408
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 408
gaatgaatgc tgtctgtgtg gaacaagcgt cgcaatgagg actctctaca ggacccgata    60
tggcat                                                               66

<210> SEQ ID NO 409
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 409
cccatggatg ctcctctgaa gagactttcc tcattgactg ccgaggcccc atgaatcaat    60
```
gtctggtagc caccgg 76

<210> SEQ ID NO 410
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 410
gcgcaggttc cgaatctatt ccaaccattc tgcactggag tcgctggctc tgatcccatt 60
acaggccc 68

<210> SEQ ID NO 411
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 411
gtggcccaat taggcttggc atctgctctg aggccagatg gagaatacac tttgctggca 60
cctgtga 67

<210> SEQ ID NO 412
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 412
aatatttgtg cggggtatgg gggtgggttt ttaaatctcg tttctcttgg acaagcacag 60
ggatctcgtt 70

<210> SEQ ID NO 413
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 413
cgcttgccta actcatactt tcccgttgac acttgatcca cgcagcgtgg cactgggacg 60
taagtggcgc agtctgaatg g 81

<210> SEQ ID NO 414
<211> LENGTH: 74
<212> TYPE: DNA
<213> ORGANISM: Artificial Sequence
<220> FEATURE:
<223> OTHER INFORMATION: Synthetic Oligonucleotide

<400> SEQUENCE: 414
ggctactctg atctatgttg ataaggaaaa tggagaacca ggcacccgtg tggttgctaa 60
ggatgggctg aagc 74

<210> SEQ ID NO 415
<211> LENGTH: 71
<212> TYPE: DNA
<213> ORGANISM: Artificial Sequence
<220> FEATURE:
<223> OTHER INFORMATION: Synthetic Oligonucleotide

```
<400> SEQUENCE: 415
tgatttctcc ctcaagctgt ttgccaaaga ggtggctcca gtgcccaaaa tccactagtc    60
ctaaaccgga a                                                         71

<210> SEQ ID NO 416
<211> LENGTH: 69
<212> TYPE: DNA
<213> ORGANISM: Artificial Sequence
<220> FEATURE:
<223> OTHER INFORMATION: Synthetic Oligonucleotide

<400> SEQUENCE: 416
agtgggagac acctgacctt tctcaagctg agattgagca aagatcaag gagtacaatg     60 cccagatca                                                            69

<210> SEQ ID NO 417
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 417
gtaggcctgt acccagacca ggaagccatc cacactcttt cggctcagct ggatctcccc    60
aaacac                                                               66

<210> SEQ ID NO 418
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 418
ctggccagtg tggattttca gcatgcctct gaagatgcaa ggaagaccat aaaccagtgg    60
gtcaaag                                                              67

<210> SEQ ID NO 419
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 419
gagagagcca gtctgatcca gaaggccaag ctggcagagc aggccgaacg ctatgaggac    60
atggcagcct                                                           70

<210> SEQ ID NO 420
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 420
taggagattg cttcggcatc gcaatggttg catttgcagt ggccttttca gttgccagcg    60
tctattc                                                              67

<210> SEQ ID NO 421
<211> LENGTH: 66
```

```
<212> TYPE: DNA
<213> ORGANISM: Artificial Sequence
<220> FEATURE:
<223> OTHER INFORMATION: Synthetic Oligonucleotide

<400> SEQUENCE: 421
actgctccgg caggtagatg agaactggta cgaagggagg atcccgggga catcccgaca      60
aggcat                                                                66

<210> SEQ ID NO 422
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 422
ggcagcttcc ttgaaccatt atgctggcta tgagcaggtc accaatgaag acctcctgac      60
caactgc                                                               67

<210> SEQ ID NO 423
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 423
gatggctcca tgtgcaaagc cgagacatca caggcagaga agcgcatgat gccagagtgc      60
cacacc                                                                66

<210> SEQ ID NO 424
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 424
gccaactgct ttcatttgtg agggatctga accaatacag agcagacata aaggaaatgg      60
gcctgagt                                                              68

<210> SEQ ID NO 425
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 425
ggtgtgccac agaccttcct acttggcctg taatcacctg tgcagccttt tgtgggcctt      60
caaaactctg tcaagaactc cgt                                             83

<210> SEQ ID NO 426
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 426
aacaccaatg ggttccatct ttctgggctc ctgattgctc aagcacagtt tggcctgatg      60
aagagg                                                                66
```

<210> SEQ ID NO 427
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 427
tccctgcggt cccagatagc ctgaatcctg cccggagtgg aactgaagcc tgcacagtgt     60
ccaccctgtt cccac                                                      75

<210> SEQ ID NO 428
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 428
cgactccgtt ctcagtgtct gacatcttga gtcccctgga ggaaagctac aagaaagtgg     60
gcatggaggg                                                            70

<210> SEQ ID NO 429
<211> LENGTH: 71
<212> TYPE: DNA
<213> ORGANISM: Artificial Sequence
<220> FEATURE:
<223> OTHER INFORMATION: Synthetic Oligonucleotide

<400> SEQUENCE: 429
gagtcgaccc tgcacctggt cctgcgcctg aggggtggct gttaattctt cagtcatggc     60
attcgcagtg c                                                          71

<210> SEQ ID NO 430
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 430
gtggatgtgc cctgaaggac aagccaggcg tctacacgag agtctcacac ttcttaccct     60
ggatccgcag                                                            70

<210> SEQ ID NO 431
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 431
caggtgtagc ctgccctctc atcaatccgt ctgggtgcca gaactcaagg ttcagtggac     60
acatccc                                                               67

<210> SEQ ID NO 432
<211> LENGTH: 71
<212> TYPE: DNA
<213> ORGANISM: Artificial Sequence
<220> FEATURE:
<223> OTHER INFORMATION: Synthetic Oligonucleotide

<400> SEQUENCE: 432

```
ctgctgtctt gggtgcattg gagccttgcc ttgctgctct acctccacca tgccaagtgg    60
tcccaggctg c                                                          71

<210> SEQ ID NO 433
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 433
cctcagcaag acgttatttg aaattacagt gcctctctct caaggcccca aaccagtaac    60
aatcagtttt gccaatcaca ctt                                             83

<210> SEQ ID NO 434
<211> LENGTH: 71
<212> TYPE: DNA
<213> ORGANISM: Artificial Sequence
<220> FEATURE:
<223> OTHER INFORMATION: Synthetic Oligonucleotide

<400> SEQUENCE: 434
tctgaagcac tctcgcacac acagtgattc cctcctcccg tcactccacg cagctggcag    60
agagcacagt g                                                          71

<210> SEQ ID NO 435
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 435
cccaaggact gagggactct gaagcctctg ggaaatgaga aggcagccac cagcgaatgc    60
taggtct                                                               67

<210> SEQ ID NO 436
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 436
gcagttggaa gacacaggaa agtatcccca aattgcagat ttatcaacgg cttttatctt    60
gaaaatagtg ccacgca                                                    77
```

PREDICTORS OF PATIENT RESPONSE TO TREATMENT WITH EGF RECEPTOR INHIBITORS

CROSS-REFERENCE TO RELATED APPLICATION

This application claims priority benefit of U.S. Provisional Application Ser. No. 61/127,816 filed on May 14, 2008, the entire disclosure of which is incorporated herein by reference in its entirety.

TECHNICAL FIELD

The present disclosure provides genes and gene sets, the expression levels of which are useful for predicting response of cancer patients to an epidermal growth factor receptor (EGFR) inhibitor therapy.

INTRODUCTION

Epidermal growth factor receptor (EGFR), also known as ERBB and HER1, is a gene that encodes a receptor protein found on the surface of some cells and to which an epidermal growth factor binds, causing the cell to divide. EGFR is a member of the HER family of receptors, and the dimerization of EGFR and v-erb-b2 erythroblastic leukemia viral oncogene homolog 2 (ERBB2), also known as HER2, is an important stimulus for breast cancer growth in ERBB2-positive breast cancers. Expression levels of EGFR are amplified in a subset of breast cancers and the resulting overexpression of the receptor contributes to breast cancer etiology.

Because cancer is characterized by rapidly proliferating cells, most cancer drugs attack rapidly dividing cells indiscriminately and, as a result, often exhibited a high degree of toxicity. In most instances, little is known regarding the mechanisms of action of these cytotoxic drugs. Targeted EGFR inhibitors, e.g., have demonstrated activity against a number of cancer types. Anti-EGFR monoclonal antibodies have shown antitumor activity in advanced colorectal cancer, in squamous cell carcinomas of the head and neck, non-small-cell lung cancer (NSCLC) and renal cell carcinomas (Baselga J and Arteaga C L (2005) J Clin Oncol 2445-2459. Clinical trials are ongoing in early stage cancer and in other tumor types and are expected to show activity in cancer types where EGFR is expressed and where EGFR ligands promote tumor growth and progression.

Given the importance in selection of therapy, there has been a push to develop drugs in concert with companion diagnostic tests capable of identifying responsive patients. Such diagnostics would address the situations where some patients who might benefit from treatment do not receive the drug, and other patients who are unlikely to benefit are unnecessarily exposed to toxic side effects, incur unnecessary expense, and/or experience a delay in being treated with alternative drugs that might prove more effective.

SUMMARY

The present disclosure provides methods and compositions to facilitate determining whether an EGFR-expressing cancer in an individual is an EGFR inhibitor-responsive cancer, as well as methods for determining the likelihood that a patient having an EGFR-expressing cancer will exhibit a beneficial response to an EGFR inhibitor therapy. The methods generally involve determining a normalized expression level of a gene product that correlates with EGFR inhibitor responsiveness.

The disclosure provides methods for predicting the likelihood that a human patient with an EGFR-expressing cancer will exhibit a beneficial response to an EGFR inhibitor cancer therapy based on expression levels of one or more response indicator genes in a biological sample obtained from a tumor in the patient. Specifically, the method entails measuring an expression level of at least one response indicator gene, or its expression product. The response indicator gene is one or more selected from a group consisting of ATP5E, TITF1, CLTC, BRCA1, AREG, PTP4A3, EREG, VAV3, SATB2, CEACAM6, EGFR, CHN2, FGFR3, C13orf18, QPRT, AMACR1, CKMT2, ID1, SORBS1, SLC26A3, ErbB3, DUSP6, VDAC2, ANXA2P2, SERPINB1, NT5E, GPC3, DUSP4, PHLDA1, K-ras, DR5, VIL2, LAMC2, SFN, ANXA1, EPHA2, P14ARF, CA9, KRT17, p14ARF, Maspin, PLAUR, LAMA3, and GCNT3. The expression level is normalized, and the normalized expression level is used to determine or predict likelihood of beneficial response, wherein increased normalized expression levels of one or more of the following are measured: ATP5E, TITF1, CLTC, BRCA1, AREG, PTP4A3, EREG, VAV3, SATB2, CEACAM6, EGFR, CHN2, FGFR3, C13orf18, QPRT, AMACR1, CKMT2, ID1, SORBS1, SLC26A3, and ErbB3 are positively correlated with the likelihood that the patient will exhibit a beneficial response to the EGFR inhibitor cancer therapy; and increased normalized expression levels of DUSP6, VDAC2, ANXA2P2, SERPINB1, NT5E, GPC3, DUSP4, PHLDA1, K-ras, DR5, VIL2, LAMC2, SFN, ANXA1, EPHA2, P14ARF, CA9, KRT17, p14ARF, Maspin, PLAUR, LAMA3, and GCNT3 are negatively correlated with the likelihood that the patient will exhibit a beneficial response to the EGFR inhibitor cancer therapy. A report is generated based on the determined likelihood of response.

The disclosure provides methods for predicting a likelihood that a human patient with a KRAS-negative, EGFR-expressing cancer will exhibit a beneficial response to an EGFR inhibitor cancer therapy based on expression levels of one or more response indicator genes in a biological sample obtained from a tumor in the patient. Specifically, the method entails measuring an expression level of at least one response indicator gene, or its expression product, selected from a group consisting of EGF, ADAM17, PTP4A3, ADAM15, QPRT, SATB2, RASSF1, VAV3, CEACAM6, EREG, AREG, TITF1, SORBS1, C13orf18, CKMT2, BTC, ATP5E, B.Catenin, CCNE1, EGFR, Bclx, BRCA1, CDC25B, CHN2, ID1, SLC26A3, VDAC2, SERPINB1, PHLDA1, ANXA2P2, KRT17, EPHA2, DUSP4, CGA, CA9, Maspin, NEDD8, DUSP6, GPC3, NT5E, VIL2, and P14ARF. The expression level is normalized, and the normalized expression level is used to determine or predict likelihood of beneficial response, wherein increased normalized expression levels of one or more of the following are measured: EGF, ADAM17, PTP4A3, ADAM15, QPRT, SATB2, RASSF1, VAV3, CEACAM6, EREG, AREG, TITF1, SORBS1, C13orf18, CKMT2, BTC, ATP5E, B.Catenin, CCNE1, EGFR, Bclx, BRCA1, CDC25B, CHN2, ID1, and SLC26A3 are positively correlated with the likelihood that the patient will exhibit a beneficial response to the EGFR inhibitor cancer therapy; and increased normalized expression levels of VDAC2, SERPINB1, PHLDA1, ANXA2P2, KRT17, EPHA2, DUSP4, CGA, CA9, Maspin, NEDD8, DUSP6, GPC3, NT5E, VIL2, and P14ARF are negatively correlated with the likelihood that the patient will exhibit a beneficial response to the EGFR inhibitor cancer therapy.

The methods of the present disclosure contemplate using a normalized expression level to determine or predict likelihood of beneficial response, based on normalized expression level(s) for single response indicator genes and/or multi-gene sets. Exemplary multi-gene sets are disclosed. The expression values are normalized relative to an expression level of one or more reference genes. The disclosure provides for measurement of normalized expression level(s) of at least one response indicator gene product. For all aspects of the present disclosure, the methods may further include determining the expression levels of at least two of said genes, or their expression products. It is further contemplated that the methods of the present disclosure may further include determining the expression levels of at least three of said genes, or their expression products. It is contemplated that the methods of the present disclosure may further include determining the expression levels of at least four of said genes, or their expression products. It is contemplated that the methods of the present disclosure may further include determining the expression levels of at least five of said genes, or their expression products. It is contemplated that the methods of the present disclosure may further include determining the expression levels of at least six of said genes, or their expression products. It is contemplated that the methods of the present disclosure may further include determining the expression levels of at least seven of said genes, or their expression products. It is contemplated that the methods of the present disclosure may further include determining the expression levels of at least eight of said genes, or their expression products. It is contemplated that the methods of the present disclosure may further include determining the expression levels of at least nine of said genes, or their expression products. The methods may involve determination of the expression levels of at least ten (10) or at least fifteen (15) of the genes listed above or their products.

A normalized expression level(s), generated as discussed above, is used to determine or predict likelihood of beneficial response, The normalized expression level(s) is indicative of the likelihood that the patient will exhibit a beneficial response to an EGFR inhibitor therapy, such as an EGFR-specific antibody or small molecule. A likelihood score (e.g., a score predicting likelihood of beneficial response to EGFR inhibitor treatment) can be calculated based on the normalized expression level(s). A score may be calculated using weighted values based on a normalized expression level of a response indicator gene and its contribution to response to EGFR inhibitor cancer therapy.

In addition, the disclosure provides arrays for carrying out the methods disclose herein, or for analyzing whether a mathematical combination of the normalized expression levels of any combination of the response indicator genes is more indicative of a likelihood that a patient will respond to treatment with an EGFR inhibitor. The arrays may include, for example, probes that hybridize to a nucleic acid sequence in a response indicator genes or an activating KRAS mutation.

Determining the expression level of one or more genes may be accomplished by, for example, a method of gene expression profiling. The method of gene expression profiling may be, for example, a PCR-based method. The expression level of said genes can be determined, for example, by RT-PCR (reverse transcriptase PCR), quantitative RT-PCR (qRT-PCR), or other PCR-based methods, immunohistochemistry, proteomics techniques, an array-based method, or any other methods known in the art or their combination. In one aspect the RNA transcripts are fragmented.

Detection of an RNA transcript of a response indicator gene may be accomplished by assaying for an exon-based sequence or an intron-based sequence, the expression of which correlates with the expression of a corresponding exon sequence.

In an exemplary embodiment, the assay for the measurement of response indicator genes, or their gene products, and/or activating KRAS mutations is provided in the form of a kit or kits.

The expression levels of the genes may be normalized relative to the expression levels of one or more reference genes, or their expression products.

The tumor sample may be, for example, a tissue sample containing cancer cells, or portion(s) of cancer cells, where the tissue can be fixed, paraffin-embedded or fresh or frozen tissue. For example, the tissue may be from a biopsy (fine needle, core or other types of biopsy) or obtained by fine needle aspiration, or by obtaining body fluid containing a cancer cell, e.g. urine, blood, etc.

For all aspects of the methods of the present disclosure, it is contemplated that for every increment of an increase in the level of one or more genes or their expression products, the patient is identified to show an incremental increase in clinical outcome.

The determination of expression levels may occur more than one time in the practice of the methods disclosed herein.

The methods may further include the step of creating a report based on the determined or predicted likelihood of beneficial response. In another aspect the present disclosure provides reports for a patient containing a summary of the expression levels of the one or more response indicator genes, or their expression products, in a tumor sample obtained from said patient. In one aspect the report is in electronic form.

In one embodiment, the EGFR inhibitor is an antibody specific for EGFR. In another, the EGFR inhibitor is a small molecule, for example an EGFR-selective tyrosine kinase inhibitor.

BRIEF DESCRIPTION OF THE DRAWINGS

FIG. 1 shows the sequences of probes and primers used to assay each gene identified in the studies.

FIG. 2 shows the sequences of amplicons expected from the use of the probes and primers shown in FIG. 1.

FIGS. 3A-10D provide sets of graphs showing probability curves. Each graph contains three lines—a center dark line and two lighter lines above and below the dark centerline. Each graph has a center dark line representing the model-predicted relationship between normalized gene expression on the x-axis and likelihood of beneficial response to an EGFR inhibitor on the y-axis (predicted probability curve). The lighter grey lines above and below the black line represent the 95% Confidence Interval for the predicted probability, i.e. at a particular expression value for the gene, there is a 95% probability that the upper and lower grey lines include the that the actual probability of response. Confidence Intervals for the probability curves were calculated using the normal approximation method. The name of the gene analyzed is indicated below each graph by the text preceding the period; for example, "AREG.2" refers to AREG. Each of FIGS. 3A-10D are described in more detail below.

FIGS. 3A-3D show probability curves that correspond to the data reported in Table 1A for analysis of ORR in all patients (K-ras negative and K-ras positive); Odds Ratio>1.

FIGS. 6A-6F shows probability curves that correspond to the data reported in Table 2B for analysis of DC in all patients (K-ras negative and K-ras positive); Odds Ratio<1.

FIGS. 7A-7C show probability curves that correspond to the data reported in Table 6A for analysis of ORR in K-ras negative patients; Odds Ratio>1.

FIGS. 10A-10D show probability curves that correspond to the data reported in Table 7B for analysis of DC in K-ras negative patients; Odds Ratio<1.

Figure 3A:
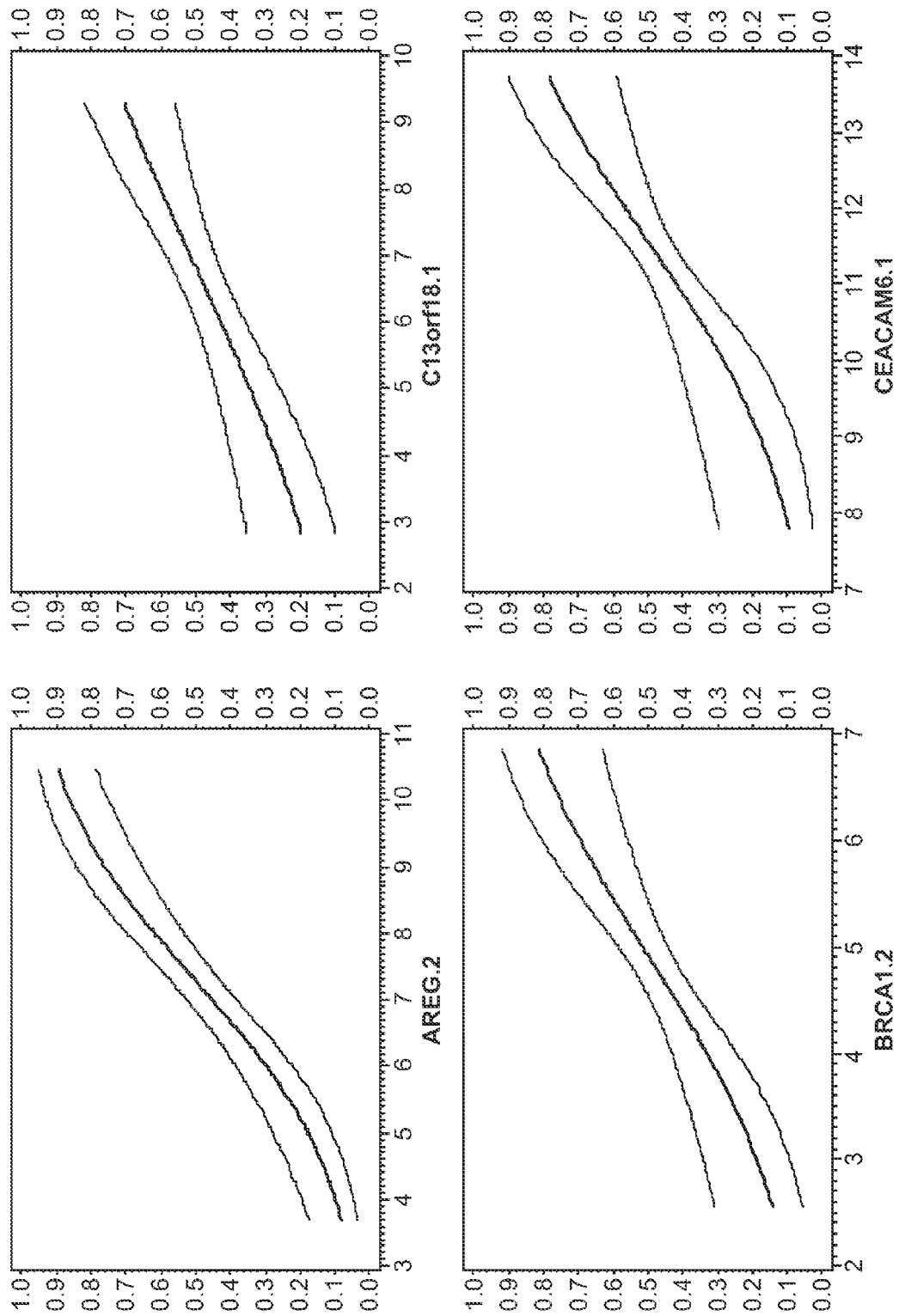
Figure 3B:
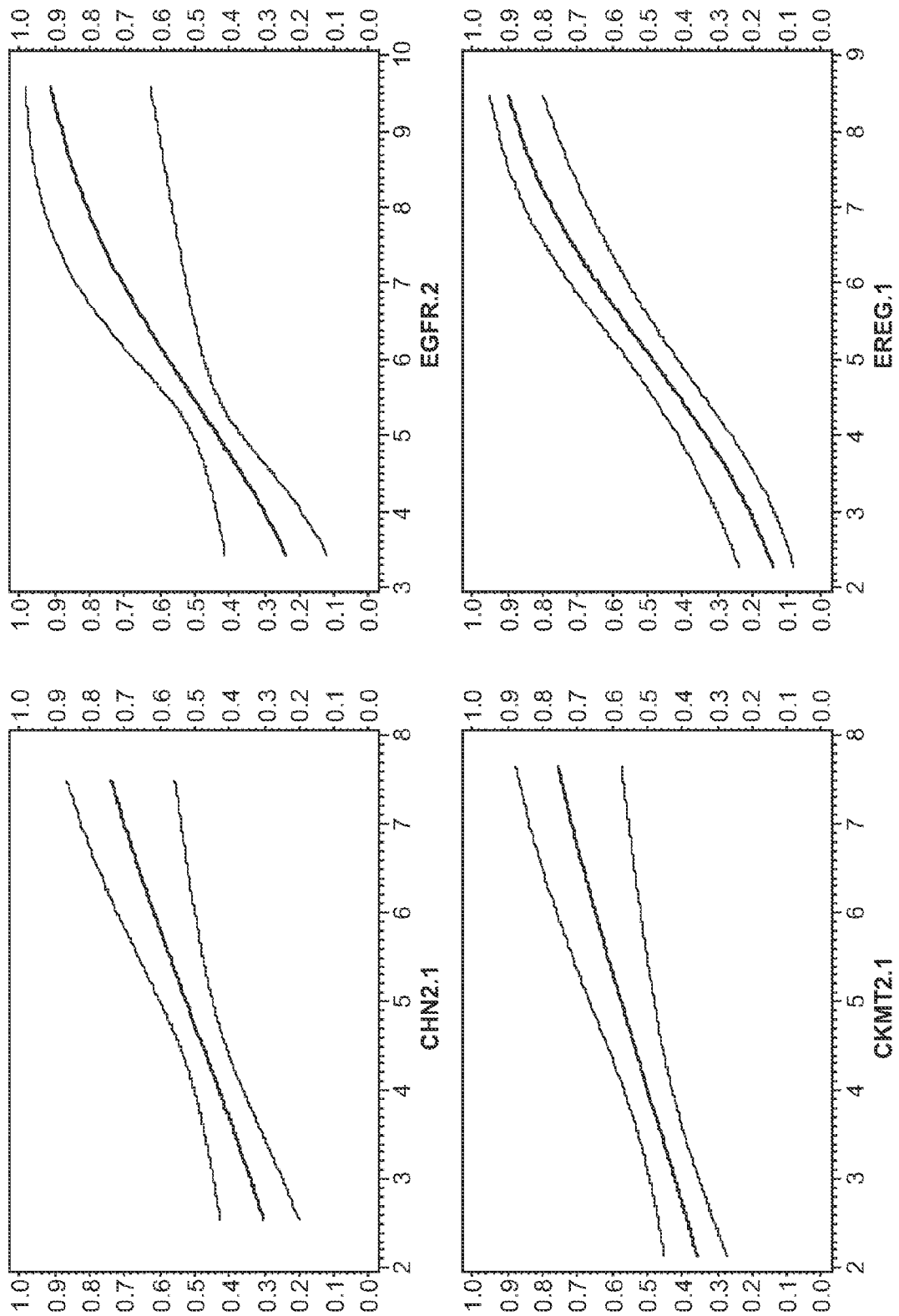
Figure 3C:
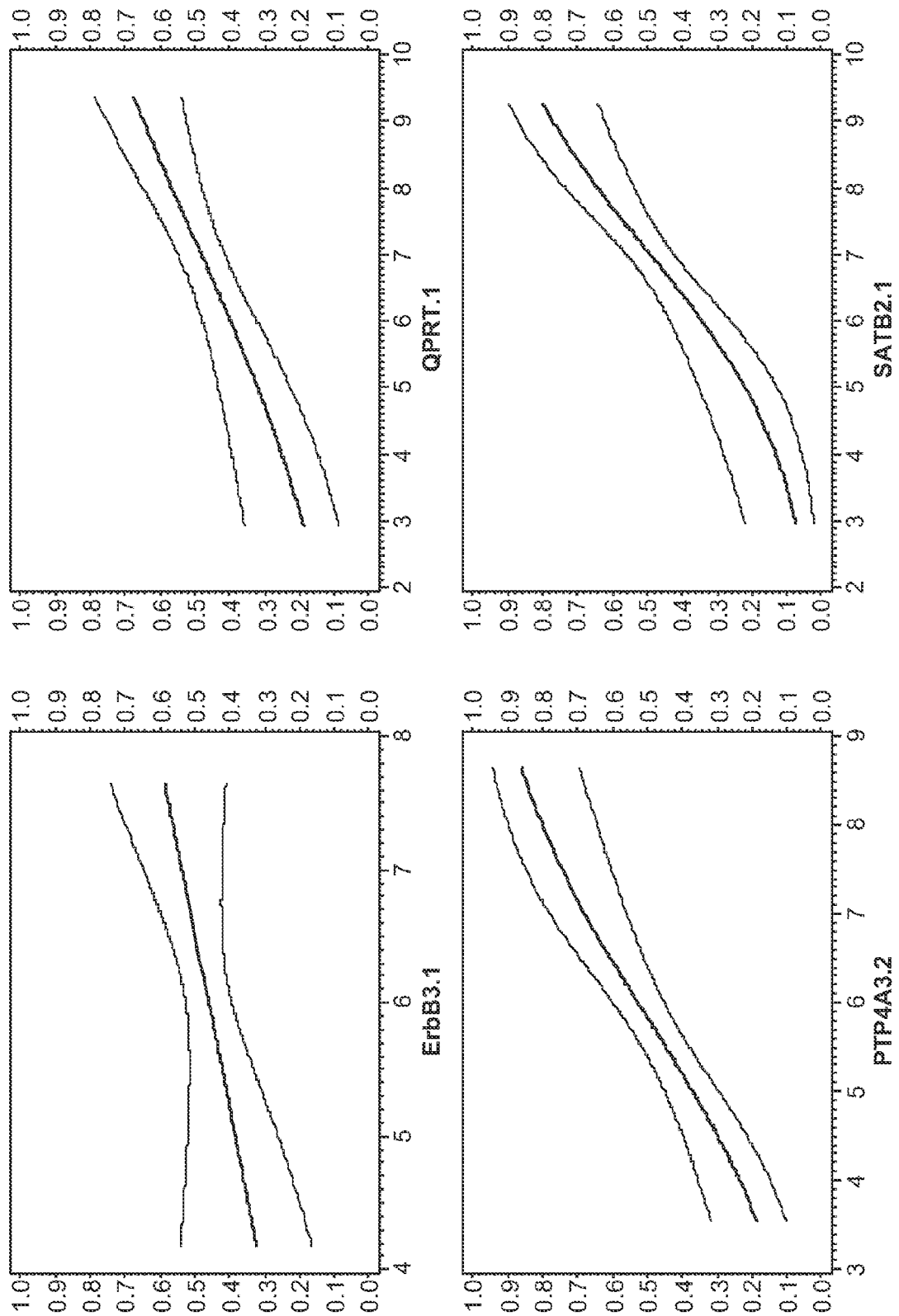
Figure 4A:
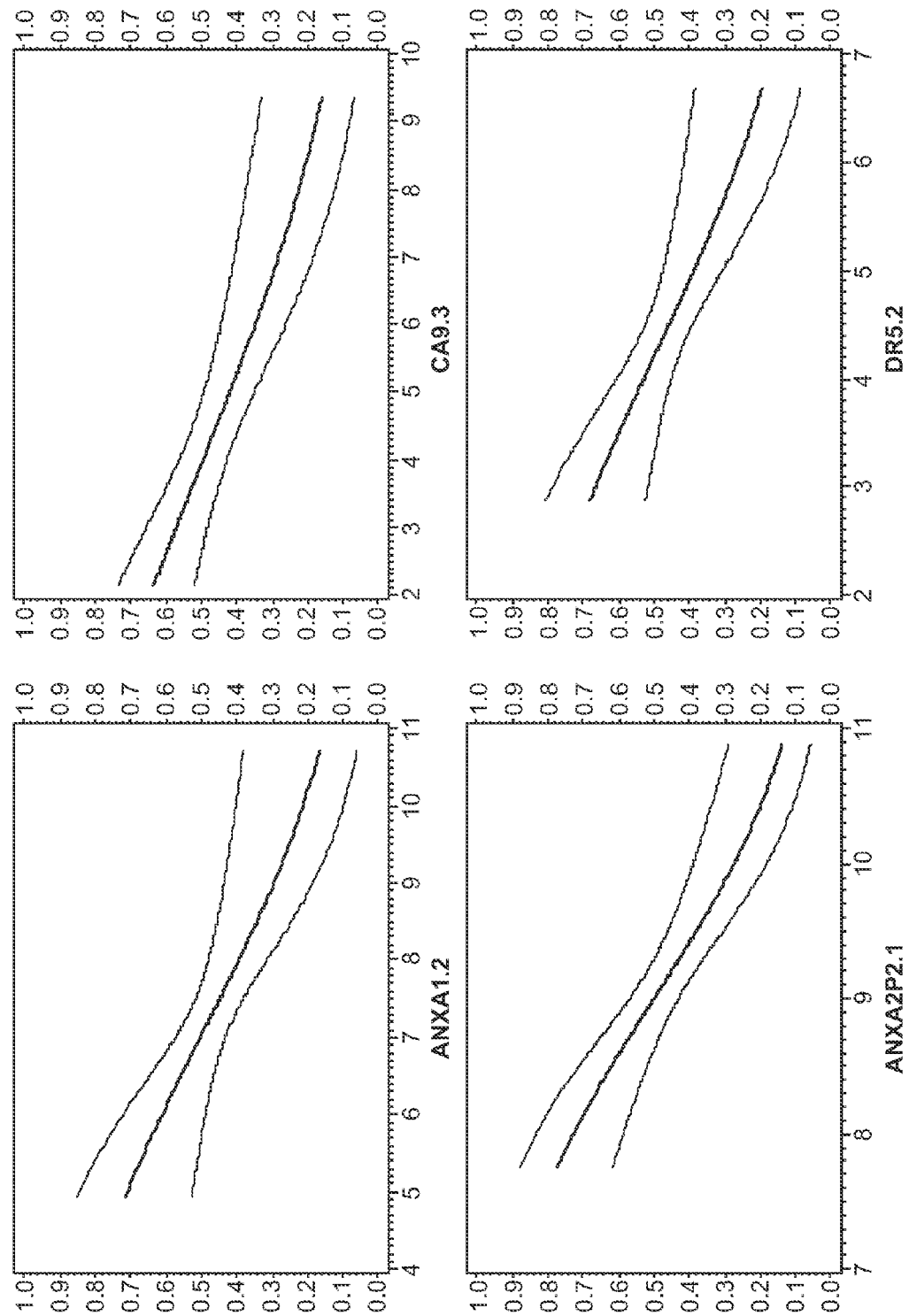
FIGS. 4A-4F show probability curves that correspond to the data reported in Table 1B for analysis of ORR in all patients (K-ras negative and K-ras positive); Odds Ratio<1.
Figure 4B:
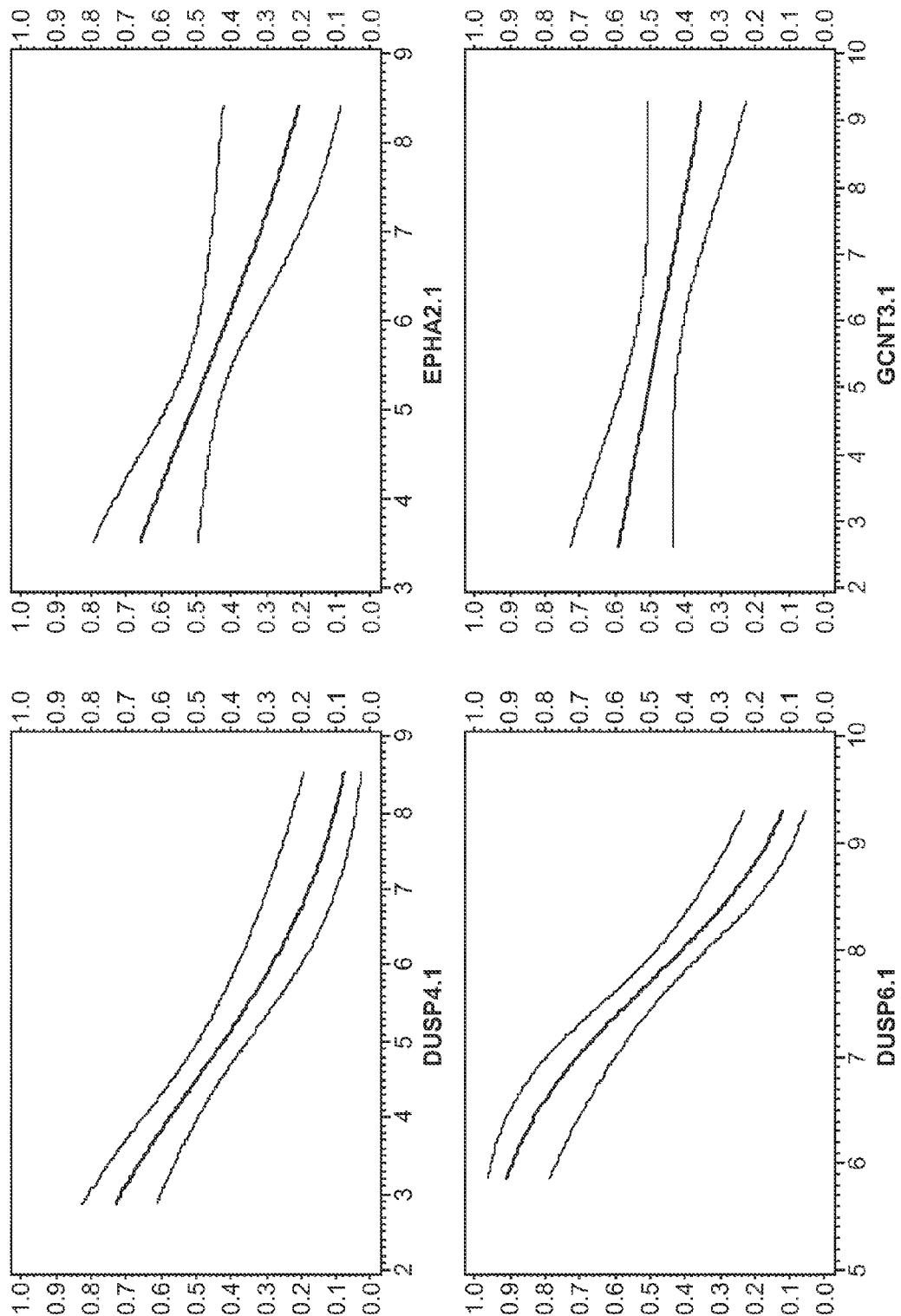
Figure 4C:
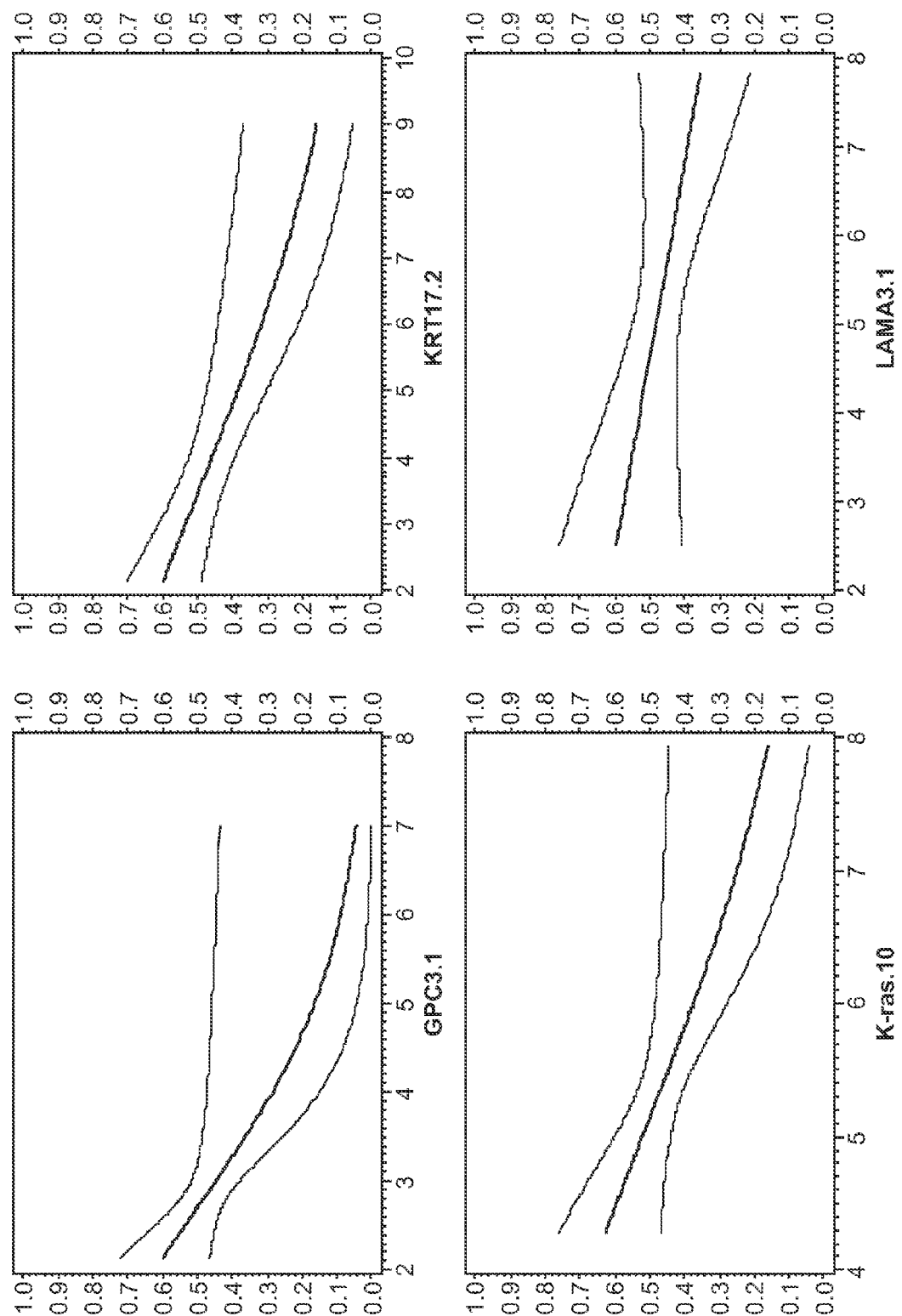
Figure 4D:
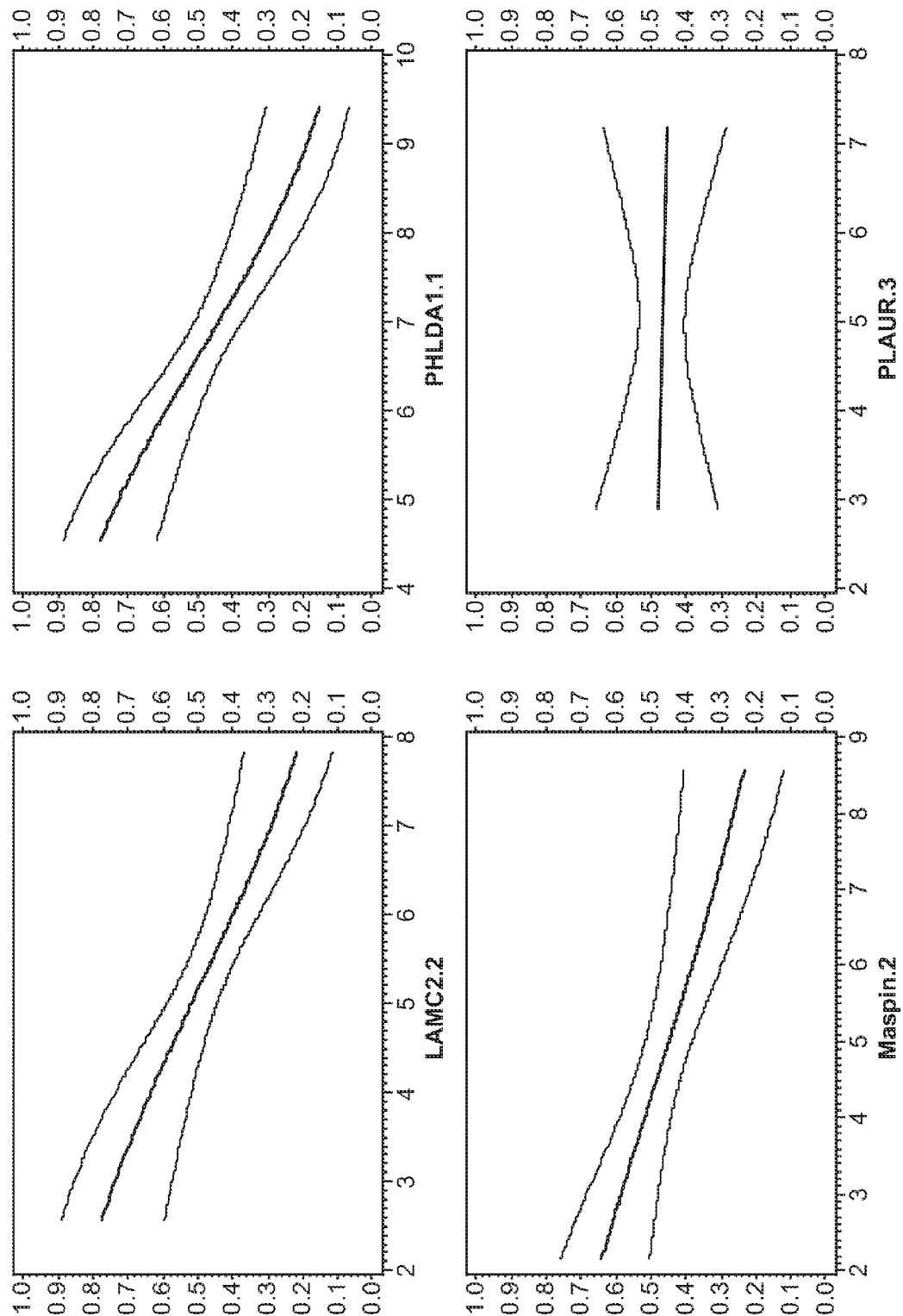
Figure 4E:
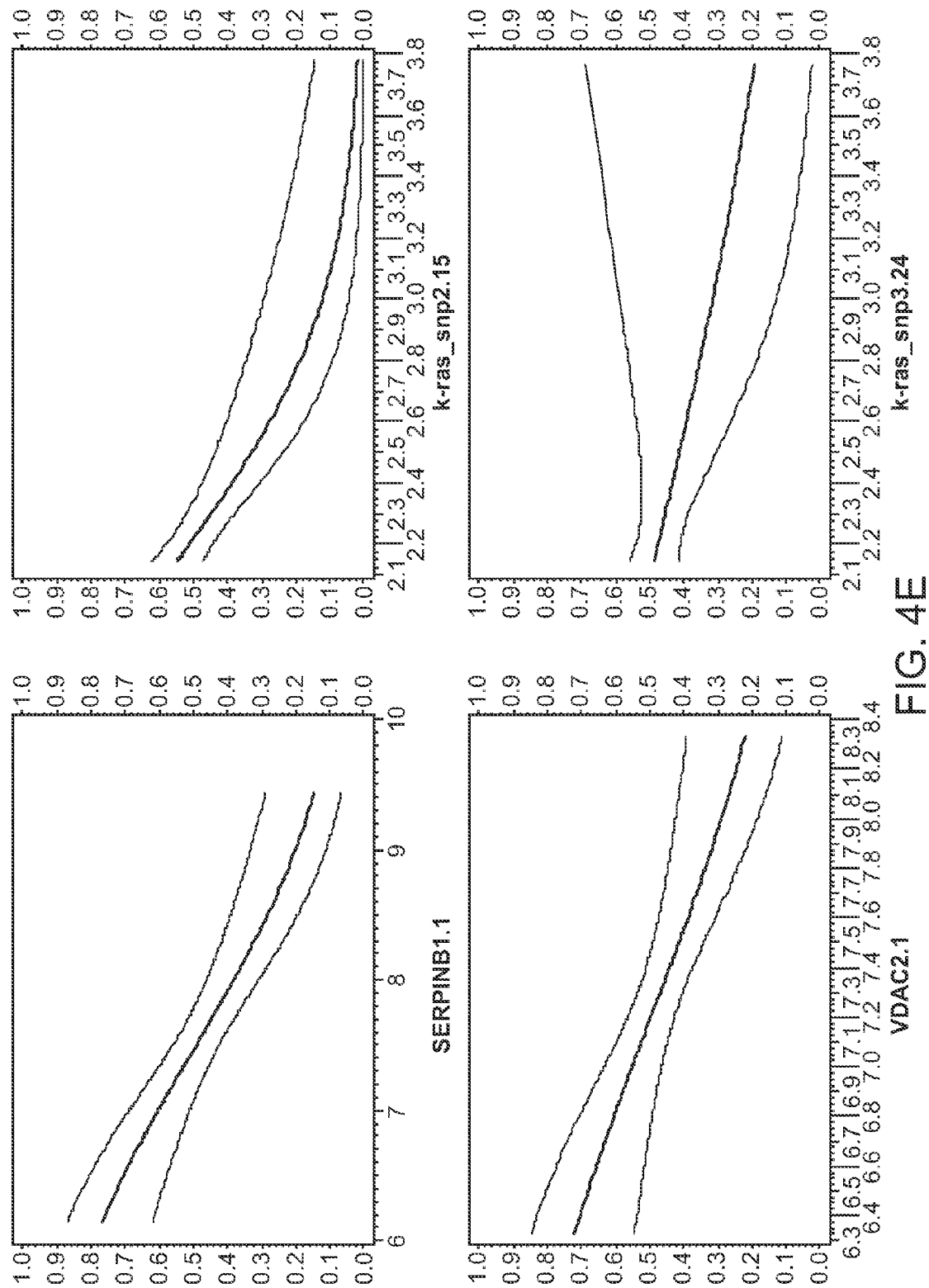
Figure 4F:
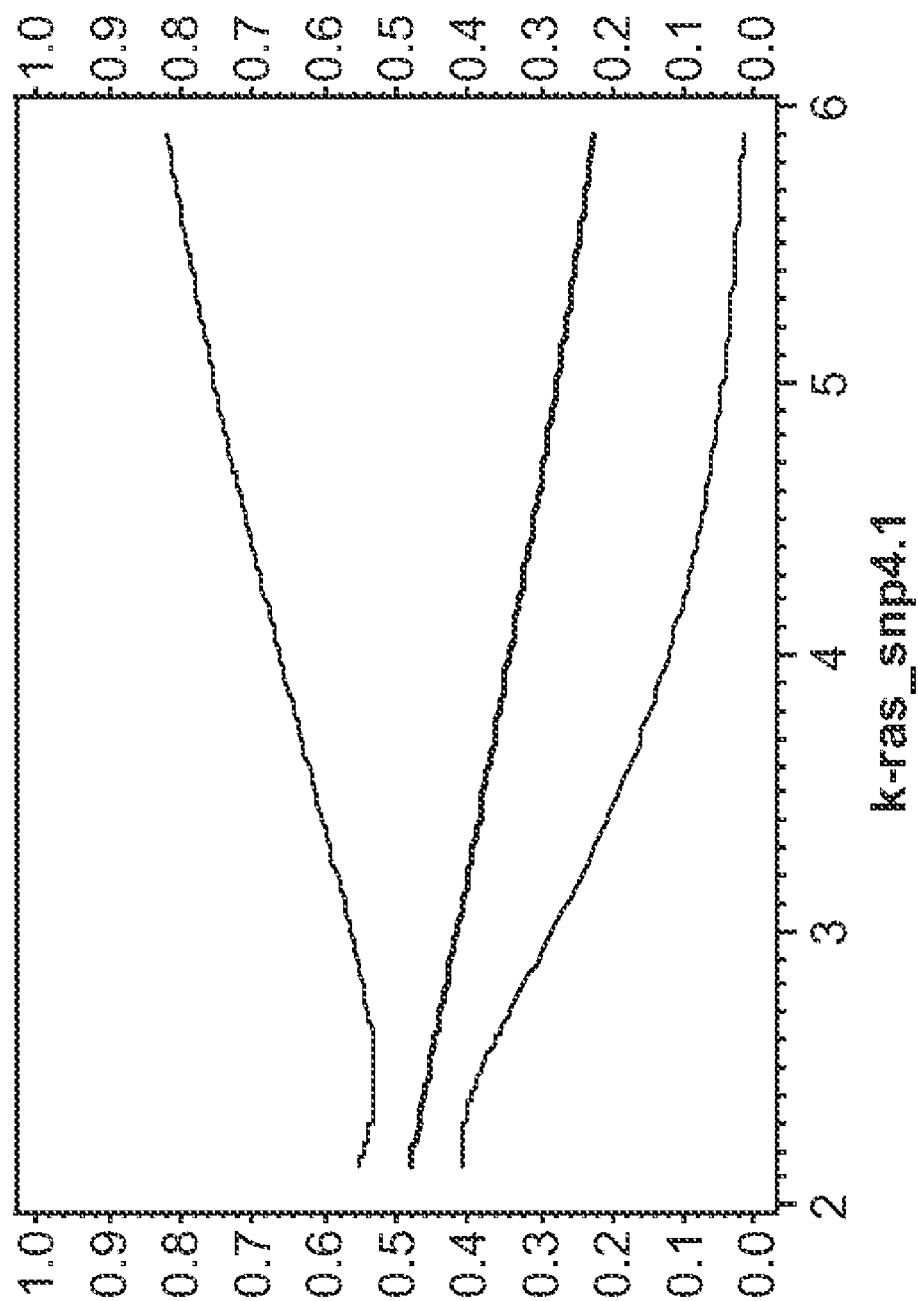
Figure 5A:
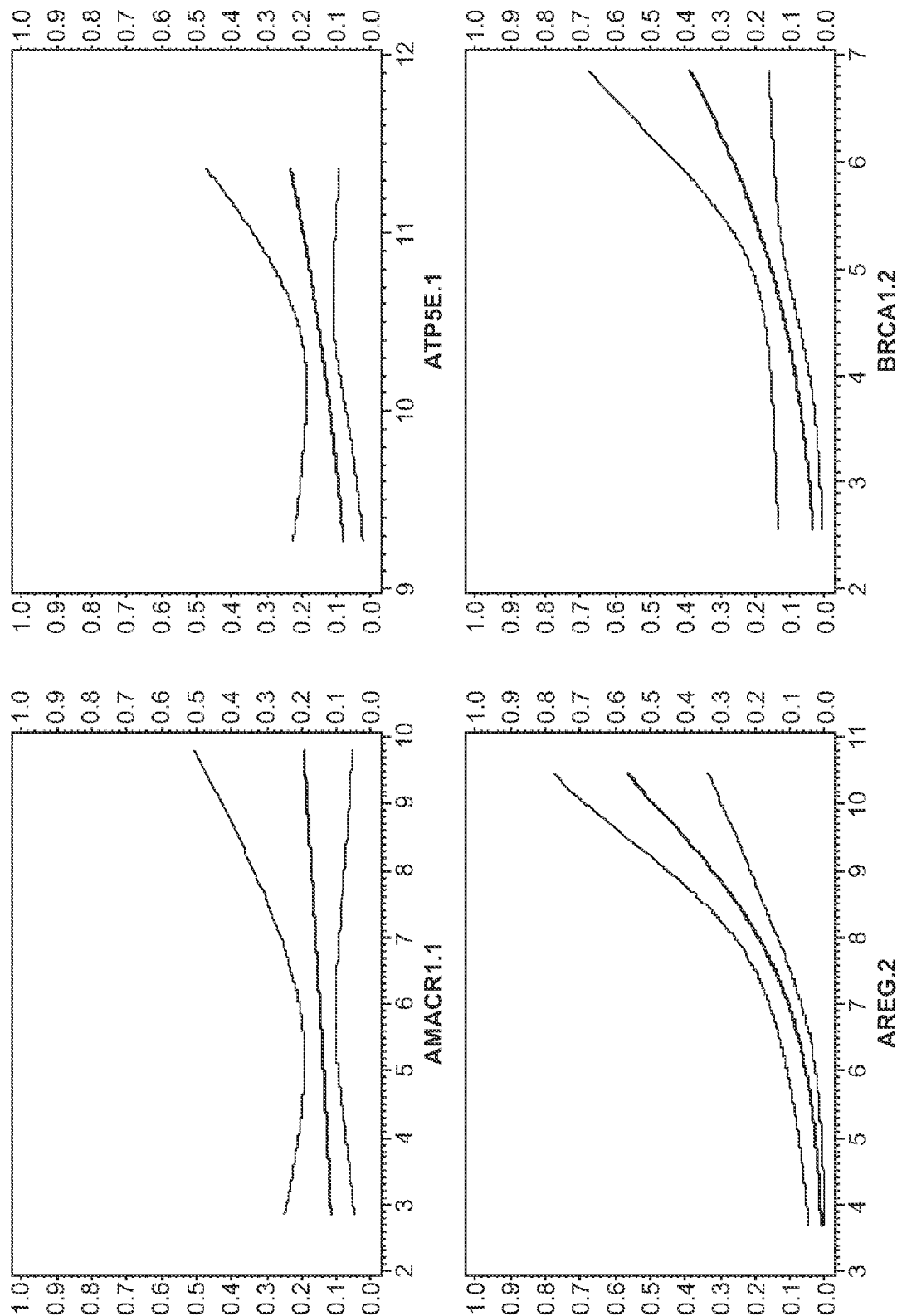
FIGS. 5A-5E show probability curves that correspond to the data reported in Table 2A for analysis of DC in all patients (K-ras negative and K-ras positive); Odds Ratio>1.
Figure 5B:
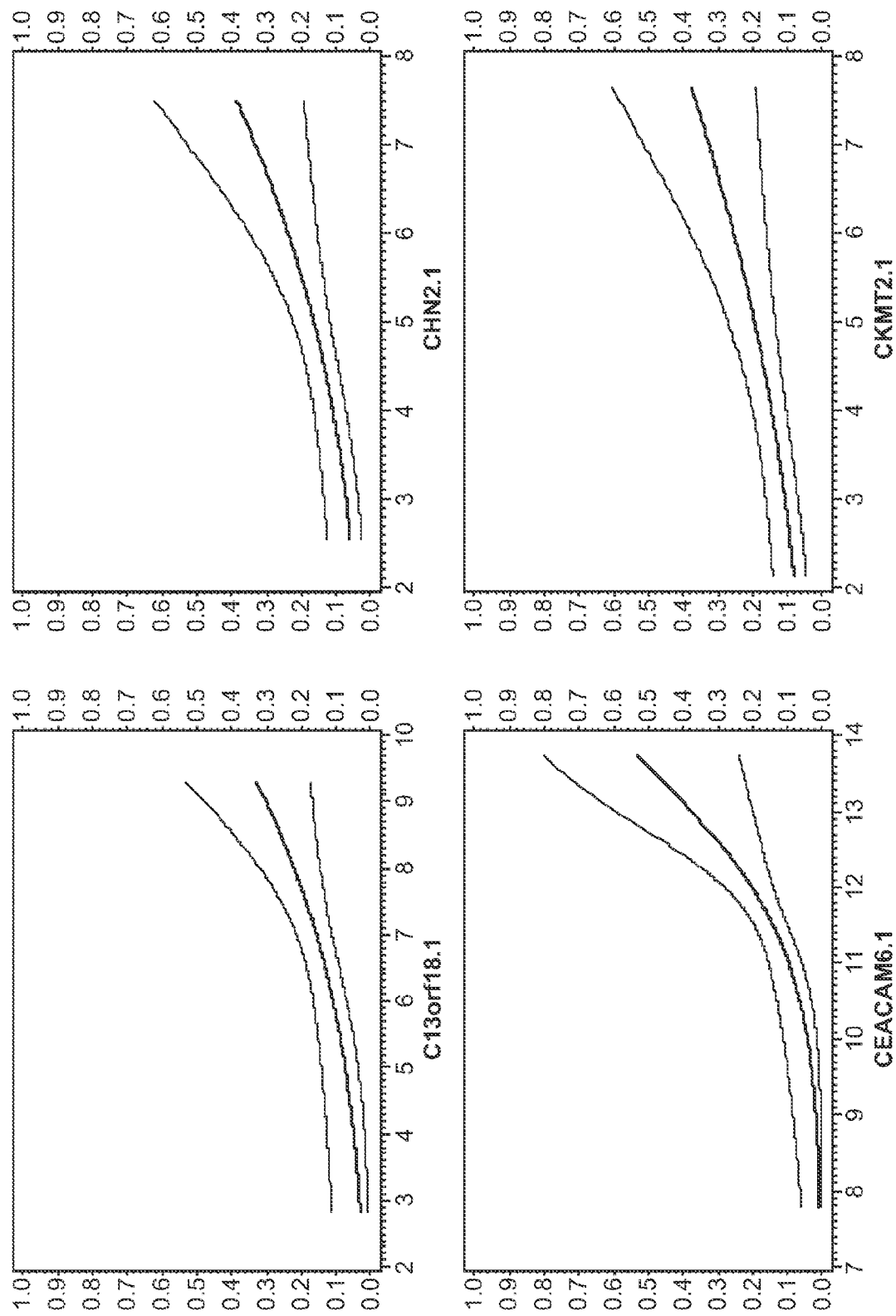
Figure 5C:
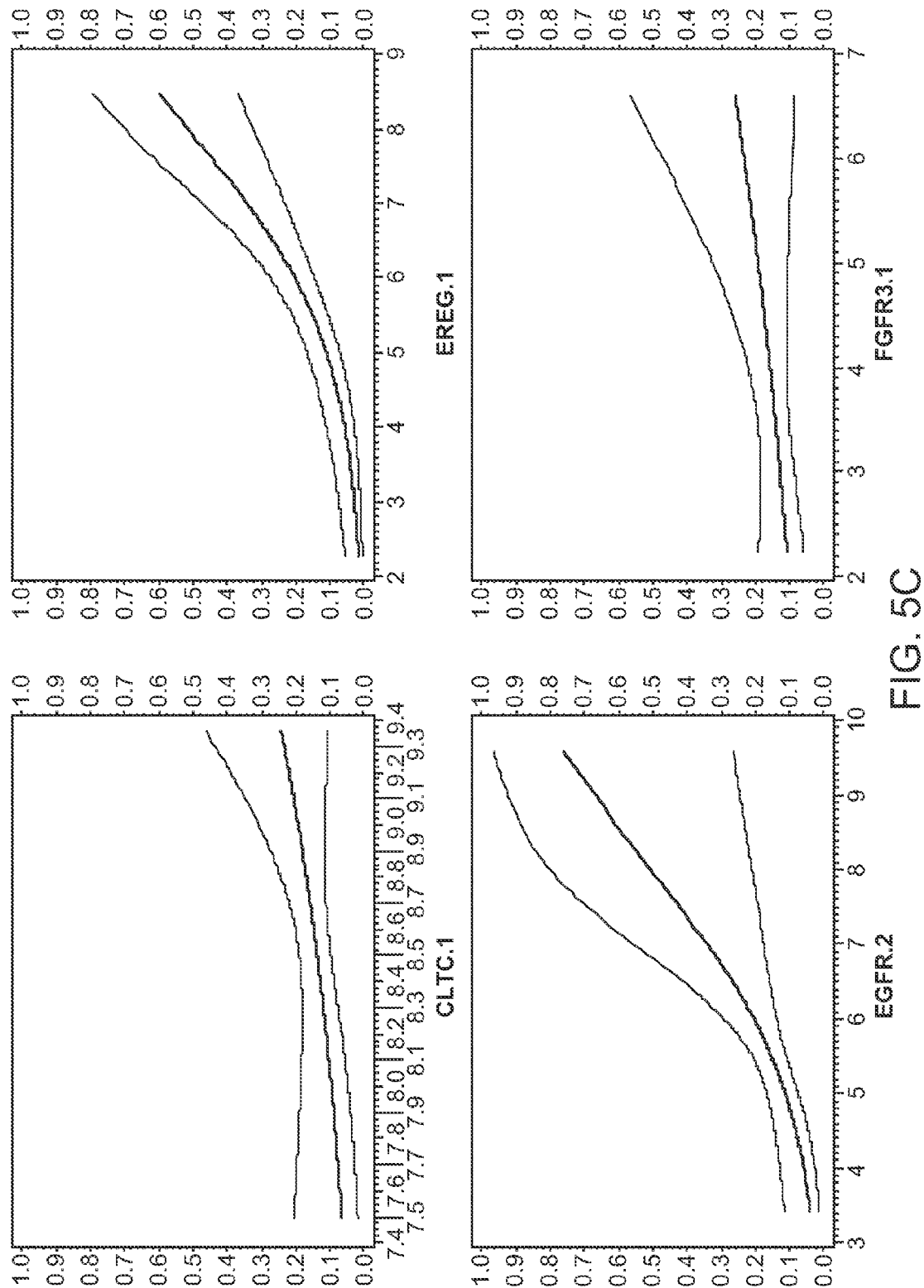
Figure 5D:
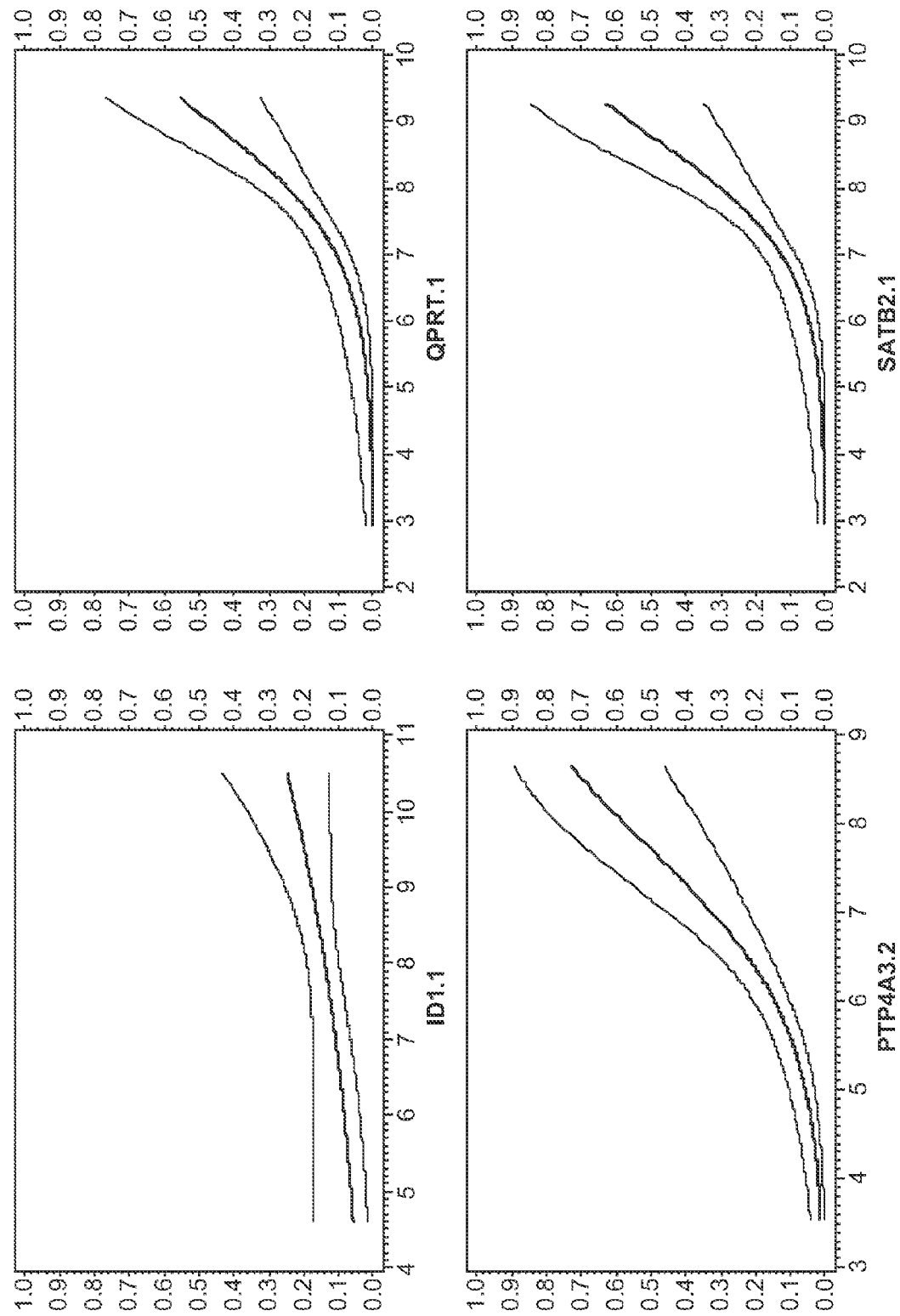
Figure 5E:
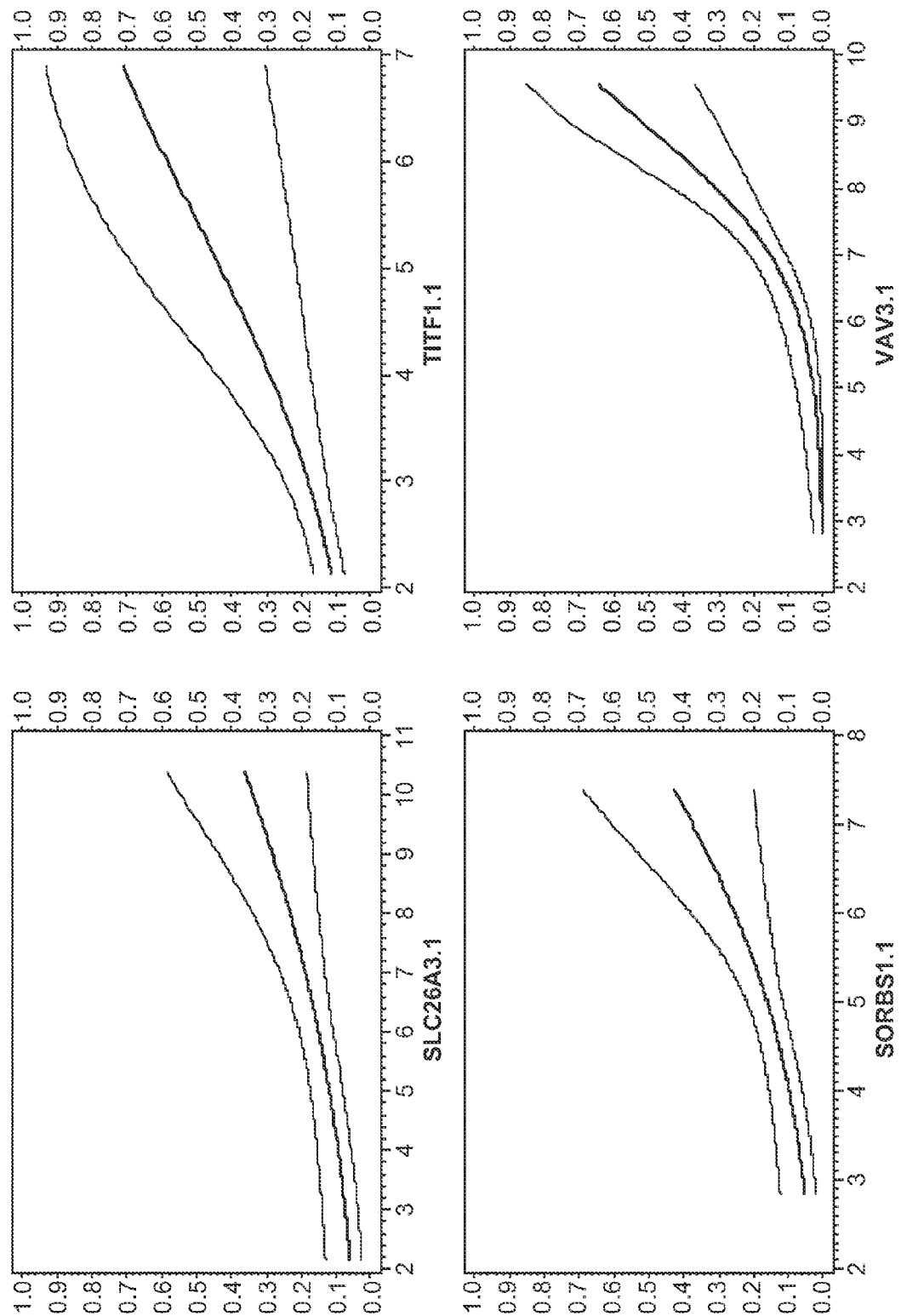
Figure 6A:
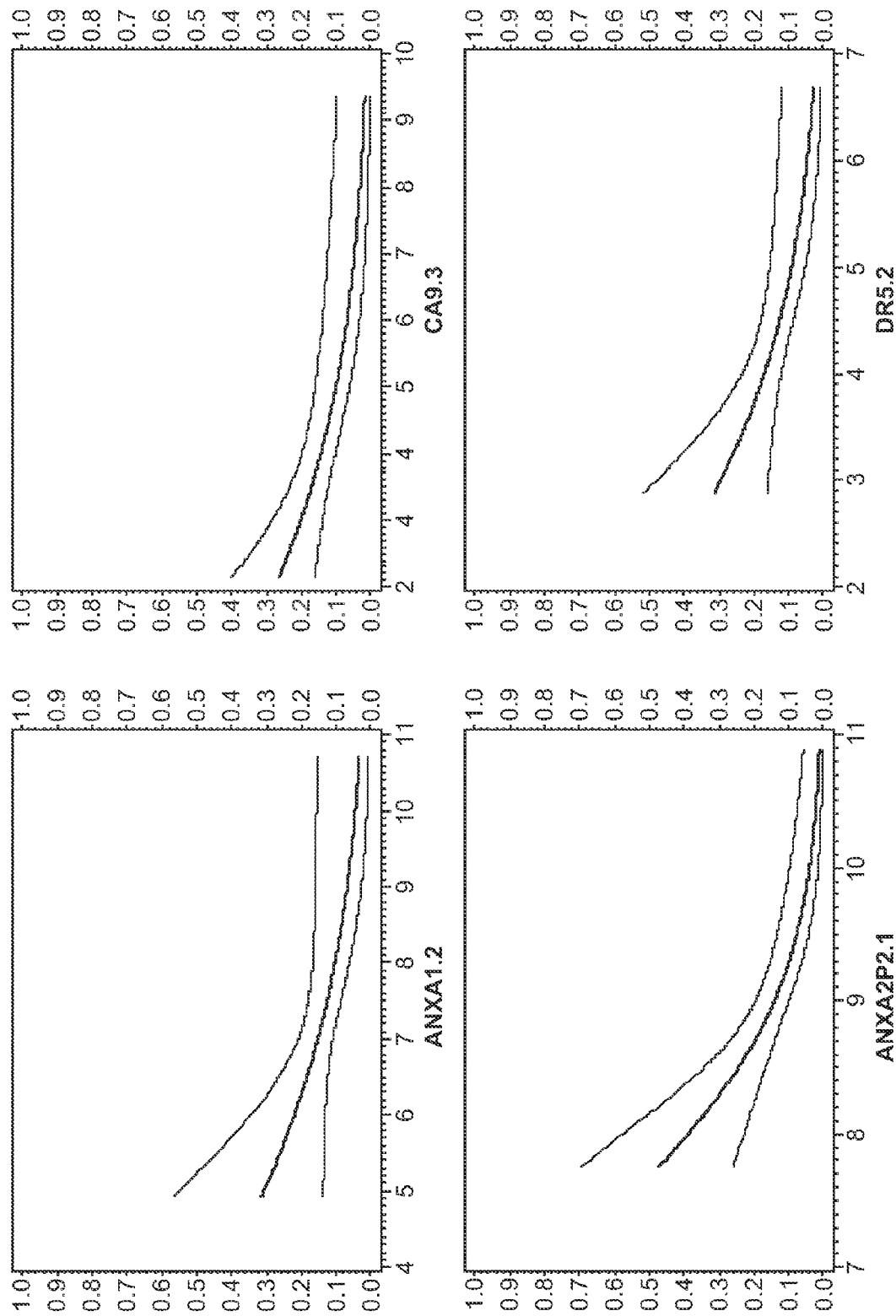
Figure 6B:
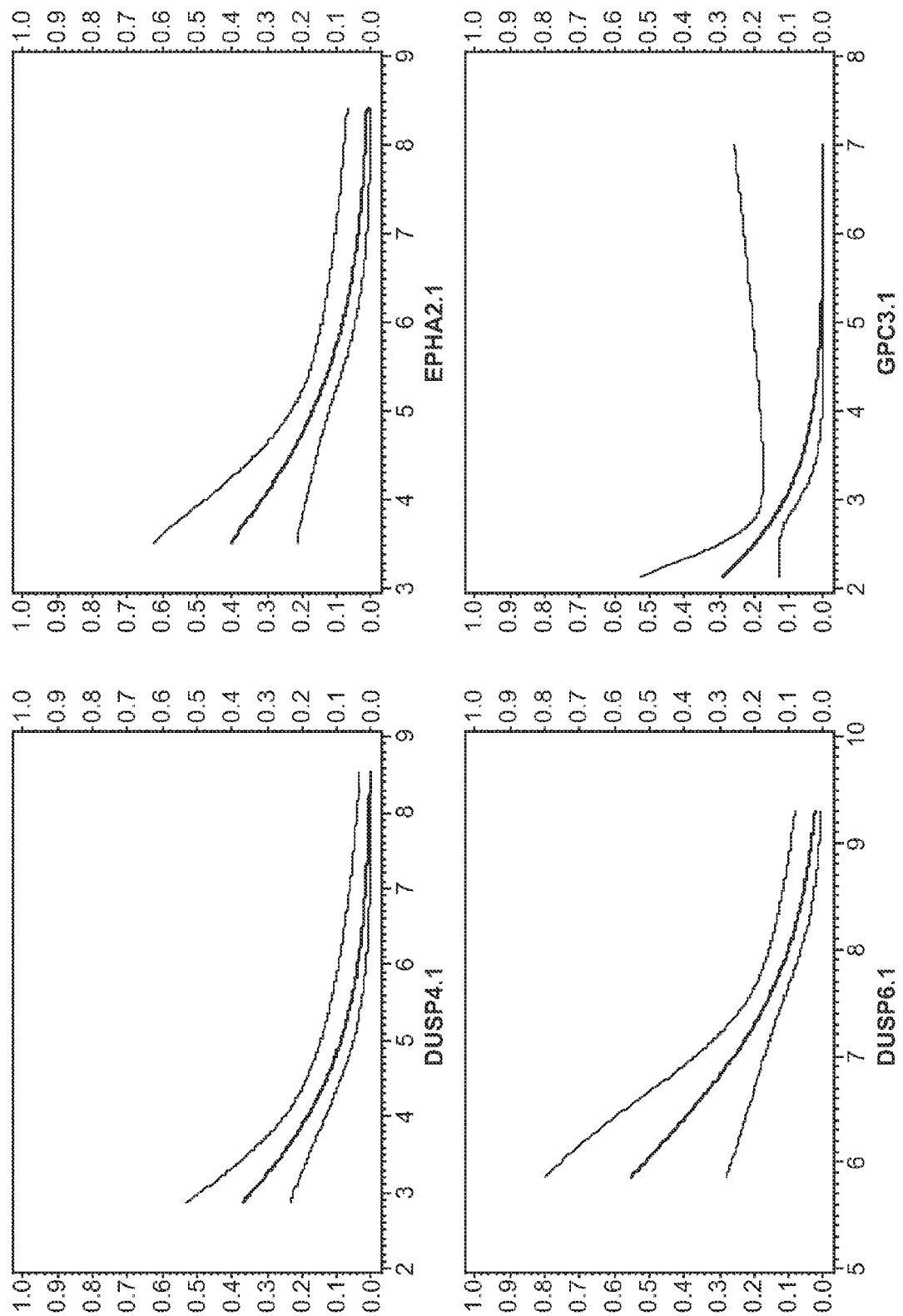
Figure 6C:
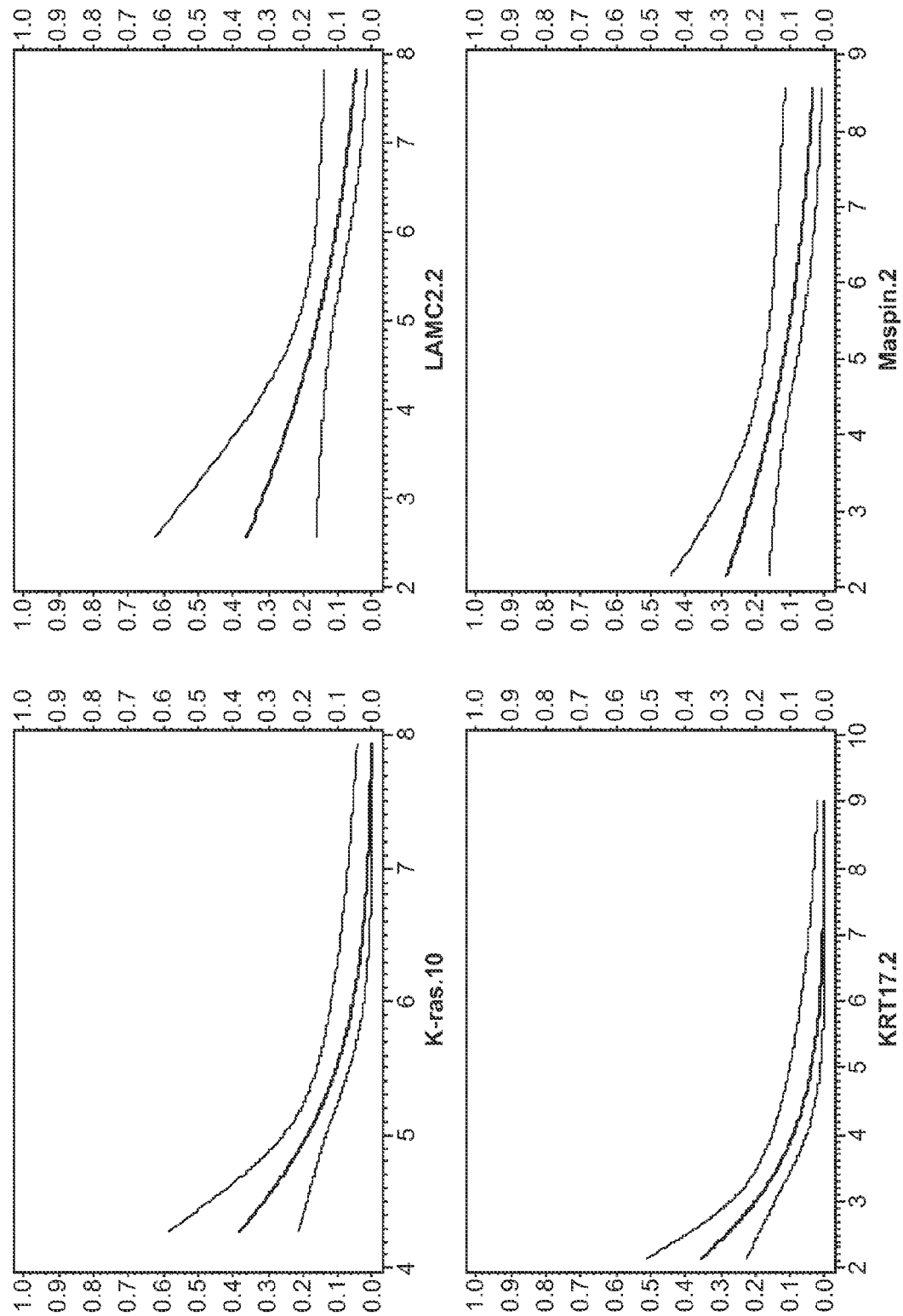
Figure 6D:
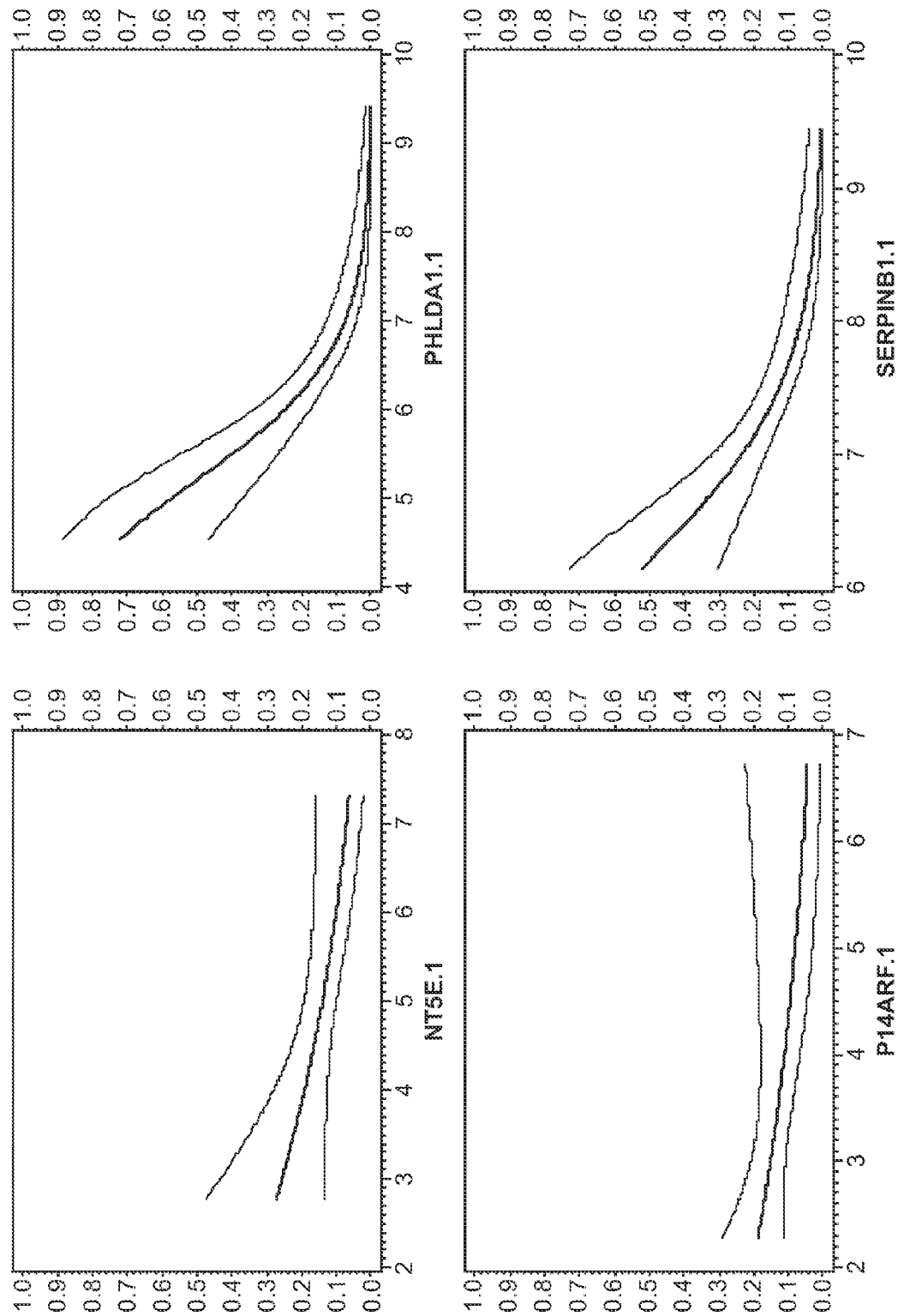
Figure 6E:
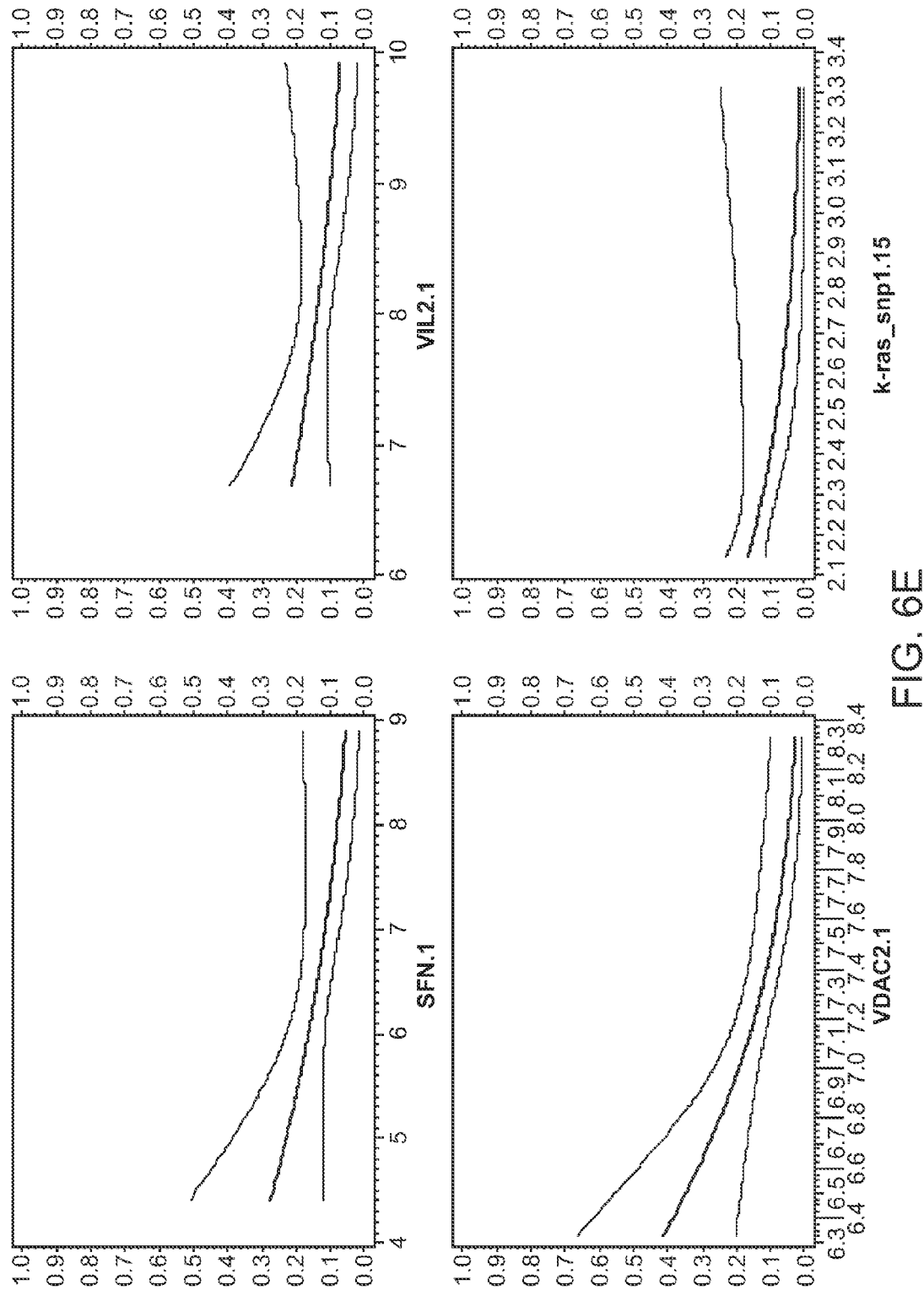

Each of Tables 1A, 1B, 2A, 2B, 6A, 6B, 7A and 7B provides an Odds Ratio for each response indicator and gene listed in the table. The Odds Ratio reported for a gene is related to the overall slope of the probability curve shown in the corresponding Figure and is a measure of the change in the model-predicted probability of response for every unit change in normalized gene expression. As shown, genes with stronger odds ratios (further from 1) in the tables are depicted with steeper slopes in the figures.

DETAILED DESCRIPTION

Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The terms "k-ras" and "KRAS" as used herein (including in tables and figures) are used interchangeably and refer to the KRAS gene identified as of the date of this filing in the NCBI Entrez Gene database as Accession No. NM_004985.3 (Entrez Gene database, NCBI), and/or its expression products.

As used herein, the term "KRAS status", refers to whether a patient's cancer is negative for an activating KRAS mutation (KRAS-negative) or positive for an activating KRAS mutation (KRAS-positive).

As used herein, the term "activating KRAS mutation" refers to a mutation in a k-ras gene that results in constitutive activation of a protein encoded by k-ras, i.e. the k-ras protein activates molecules downstream in its signaling pathway in the absence of receptor bound ligand. As an example, the k-ras protein might activate downstream signaling in the absence of EGF, amphiregulin, or epiregulin binding to EGFR.

As used herein, the term "EGFR-expressing cancer" refers to a cancer tumor with cells that express a cell surface epidermal growth factor receptor (EGFR) polypeptide.

As used herein, the term "epidermal growth factor receptor" ("EGFR") refers to a gene that encodes a membrane polypeptide that binds, and is thereby activated by, epidermal growth factor (EGF). EGFR is also known in the literature as ERBB, ERBB1 and HER1. An exemplary EGFR is the human epidermal growth factor receptor (see Ullrich et al. (1984) Nature 309:418-425; Genbank accession number NP_005219.2). Binding of an EGF ligand activates the EGFR (e.g. resulting in activation of intracellular mitogenic signaling, autophosphorylation of EGFR). One of skill in the art will appreciate that other ligands, in addition to EGF, can bind to and activate the EGFR. Examples of such ligands include, but are not limited to, amphiregulin, epiregulin, TGF-α, betacellulin, and heparin-binding EGF (HB-EGF) (Strawn and Shawver (1998) Exp. Opin. Invest. Drugs 7(4) 553-573, and "The Protein Kinase Facts Book: Protein Tyrosine Kinases" (1995) Hardie, et al. (eds.), Academic Press, NY, N.Y.). See also, Oda et al. ((2005) Molec. Systems Biol. 1:2005.0010; and Moulder et al. ((2001) Cancer Res. 61:8887.

As used herein, an "EGFR gene" refers to a nucleic acid that encodes an EGFR gene product, e.g., an EGFR mRNA, an EGFR polypeptide, and the like.

As used herein, "EGFR inhibitor" refers to any agent capable of directly or indirectly inhibiting activation of an EGFR. EGFR inhibitors include agents that bind to an EGFR and inhibit its activation. EGFR inhibitors include antibodies that bind to an EGFR and inhibit activation of the EGFR; as well as small molecule tyrosine kinase inhibitors that inhibit activation of an EGFR. Antibodies to EGFR include IgG; IgM; IgA; antibody fragments that retain EGFR binding capability, e.g., Fv, Fab, F(ab)$_2$, single-chain antibodies, and the like; chimeric antibodies; etc. Small molecule tyrosine kinase inhibitors of EGFR include EGFR-selective tyrosine kinase inhibitors. Small molecule tyrosine kinase inhibitors of EGFR can have a molecular weight in a range of from about 50 Da to about 10,000 Da.

The term "tumor," as used herein, refers to any neoplastic cell growth and proliferation, whether malignant or benign, and all pre-cancerous and cancerous cells and tissues.

The terms "cancer" and "cancerous" refer to or describe the physiological condition in mammals that is typically characterized in part by unregulated cell growth. Examples of cancer include, but are not limited to, colorectal cancer, breast cancer, ovarian cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, brain cancer, non-small cell lung cancer, squamous cell cancer of the head and neck, endometrial cancer, multiple myeloma, rectal cancer, and esophageal cancer. In an exemplary embodiment, the cancer is colorectal cancer.

As used herein, the term "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The terms "subject," "individual," and "patient" are used interchangeably herein to refer to a mammal being assessed for treatment and/or being treated. In an embodiment, the mammal is a human. The terms "subject," "individual," and "patient" thus encompass individuals having cancer (e.g., colorectal cancer or other cancer referenced herein), including those who have undergone or are candidates for resection (surgery) to remove cancerous tissue (e.g., cancerous colorectal tissue or other cancer referenced herein).

As used herein, the terms "treatment," "treating," and the like, refer to administering an agent, or carrying out a procedure (e.g., radiation, a surgical procedure, etc.), for the purposes of obtaining a effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

As used herein in the context of patient response to an EGFR inhibitor treatment, the terms "beneficial response," "beneficial patient response," and "clinically beneficial response," "clinical benefit," and the like, are used interchangeably and refer to favorable patient response to a drug as opposed to unfavorable responses, i.e. adverse events. In individual patients, beneficial response can be expressed in terms of a number of clinical parameters, including loss of detectable tumor (complete response, CR), decrease in tumor size and/or cancer cell number (partial response, PR), tumor growth arrest (stable disease, SD), enhancement of anti-tumor immune response, possibly resulting in regression or rejection of the tumor; relief, to some extent, of one or more symptoms associated with the tumor; increase in the length of survival following treatment; and/or decreased mortality at a given point of time following treatment. Continued increase in tumor size and/or cancer cell number and/or tumor metastasis is indicative of lack of beneficial response to treatment.

In a population the clinical benefit of a drug, i.e. its efficacy can be evaluated on the basis of one or more endpoints. For example, analysis of overall response rate (ORR) classifies as responders those patients who experience CR or PR after treatment with drug. Analysis of disease control (DC) classifies as responders those patients who experience CR, PR or SD after treatment with drug.

As is used herein, the term "progression free survival" refers to the time interval from treatment of the patient until the progression of cancer or death of the patient, whichever occurs first.

As used herein, the term "responder" refers to a patient who has an EGFR-expressing cancer, and who exhibits a beneficial clinical response following treatment with an EGFR inhibitor.

As used herein, the term "non-responder" refers to a patient who has an EGFR-expressing cancer, and who has not shown a beneficial response following treatment with an EGFR inhibitor.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases. The correlation need not necessarily be a linear correlation and need not apply across the entire range of the variables.

The term "tumor sample" as used herein means a sample comprising tumor material obtained from a cancerous patient. The term encompasses clinical samples, for example tissue obtained by surgical resection and tissue obtained by biopsy, such as for example a core biopsy or a fine needle biopsy. The term also encompasses samples comprising tumor cells obtained from sites other than the primary tumor, e.g., circulating tumor cells. The term encompasses cells that are the progeny of the patient's tumor cells, e.g. cell culture samples derived from primary tumor cells or circulating tumor cells. The term encompasses samples that may comprise protein or nucleic acid material shed from tumor cells in vivo, e.g. bone marrow, blood, plasma, serum, and the like. The term also encompasses samples that have been enriched for tumor cells or otherwise manipulated after their procurement and samples comprising polynucleotides and/or polypeptides that are obtained from a patient's tumor material.

The terms "gene product" and "expression product" are used interchangeably herein in reference to a molecule produced using a gene's information. For example, a gene product or expression product would include RNA transcription products (transcripts) of the gene, including mRNA and the polypeptide translation products of such RNA transcripts, whether such product is modified post-translationally or not (e.g., unspliced RNA, a splice variant mRNA, RNA fragment, etc.). In addition, a gene product or expression product includes the polypeptide translation products of such RNA, whether such product is modified post-translationally or not (e.g., a splice variant polypeptide, etc.)

As used herein, the term "normalized expression level" refers to an expression level of a response indicator gene relative to the level of an expression product of a reference gene(s).

As used herein, the term "response indicator gene" refers to a gene, the expression of which correlates positively or negatively with beneficial patient response to EGFR inhibitor treatment. The expression of a response indicator gene may be measured by determining the expression level of an expression product of the response indicator gene.

The term "increased expression" or "increased normalized expression" with regard to a gene or an RNA transcript (or other expression product, e.g., protein) is used to refer to the level of the transcript (or fragmented RNA) determined by normalization to the level of one or more reference mRNA(s), which might be all measured transcripts in the specimen, a single reference mRNA, or a particular reference set of mRNAs. A gene exhibits "increased expression" in a subpopulation of subjects when the normalized expression level of an RNA transcript (or its gene product) is higher in one clinically relevant subpopulation of patients (e.g., patients who are responsive to an EGFR inhibitor) than in a related subpopulation (e.g., patients who are not responsive to said EGF inhibitor). In the context of an analysis of a normalized expression level of a gene in tissue obtained from an individual subject, a gene is exhibits "increased expression" when the normalized expression level of the gene trends toward or more closely approximates the normalized expression level characteristic of such a clinically relevant subpopulation of patients. Thus, for example, when the gene analyzed is a gene that shows increased expression in responsive subjects as compared to non-responsive subjects, then if the expression level of the gene in the patient sample trends toward a level of expression characteristic of a responsive subject, then the gene expression level supports a determination that the individual patient is likely to be a responder. Similarly, where the gene analyzed is a gene that is increased in expression in non-responsive patients as compared to responsive patients, then if the expression level of the gene in the patient sample trends toward a level of expression characteristic of a non-responsive subject, then the gene expression level supports a determination that the individual patient will be non-responsive. Thus normalized expression of a given gene as disclosed herein can be described as being positively correlated with an increased likelihood of positive clinical response to chemotherapy or as being positively correlated with a decreased likelihood of a positive clinical response to chemotherapy.

As used herein, the terms "label" and "detectable label" refer to a molecule capable of being detected, where such molecules include, but are not limited to, radioactive isotopes, fluorescers (fluorophores), chemiluminescers, chromophores, enzymes, enzyme substrates, enzyme cofactors, enzyme inhibitors, chromophores, dyes, metal ions, metal sols, ligands (e.g., biotin, avidin, strepavidin or haptens), intercalating dyes and the like. The term "fluorescer" or "fluorophore" refers to a substance or a portion thereof which is capable of exhibiting fluorescence in a detectable range.

As used herein, the term "target nucleic acid region" or "target nucleic acid" refers to a nucleic acid with a "target sequence" to be detected (e.g., in a method involving nucleic acid hybridization and/or amplification). The target nucleic acid may be either single-stranded or double-stranded and may or may not include other sequences besides the target sequence (e.g., the target nucleic acid may or may not include nucleic acid sequences upstream or 5' flanking sequence, and may or may not include downstream or 3' flanking sequence. Where detection is by amplification, these other sequences in addition to the target sequence may or may not be amplified with the target sequence.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal ion concentration, and salt concentration. Primers are generally of a length compatible with their use in synthesis of primer extension products, and can be in the range of between about 8 nucleotides and about 100 nucleotides (nt) in length, such as about 10 nt to about 75 nt, about 15 nt to about 60 nt, about 15 nt to about 40 nt, about 18 nt to about 30 nt, about 20 nt to about 40 nt, about 21 nt to about 50 nt, about 22 nt to about 45 nt, about 25 nt to about 40 nt, and so on, e.g., in the range of between about 18 nt and about 40 nt, between about 20 nt and about 35 nt, between about 21 and about 30 nt in length, inclusive, and any length between the stated ranges. Primers can be in the range of between about 10-50 nucleotides long, such as about 15-45, about 18-40, about 20-30, about 21-25 nt and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length. In this context, the term "about" may be construed to mean 1, 2, 3, 4, 5, 6, 7, 8, 9, 10, 11, 12, 13, 14, 15, 16, 17, 18, 19 or 20 more nucleotides either 5' or 3' from either termini or from both termini.

Primers are in many embodiments single-stranded for maximum efficiency in amplification, but may alternatively be double-stranded. If double-stranded, the primer is in many embodiments first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the covalent addition of bases at its 3' end.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, which contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with their use in specific detection of all or a portion of a target sequence of a target nucleic acid, and are in many embodiments in the range of between about 8 nt and about 100 nt in length, such as about 8 to about 75 nt, about 10 to about 74 nt, about 12 to about 72 nt, about 15 to about 60 nt, about 15 to about 40 nt, about 18 to about 30 nt, about 20 to about 40 nt, about 21 to about 50 nt, about 22 to about 45 nt, about 25 to about 40 nt in length, and so on, e.g., in the range of between about 18-40 nt, about 20-35 nt, or about 21-30 nt in length, and any length between the stated ranges. In some embodiments, a probe is in the range of between about 10-50 nucleotides long, such as about 15-45, about 18-40, about 20-30, about 21-28, about 22-25 and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length. In this context, the term "about" may be construed to mean 1, 2, 3, 4, 5, 6, 7, 8, 9, 10, 11, 12, 13, 14, 15, 16, 17, 18, 19 or 20 more nucleotides either 5' or 3' from either termini or from both termini.

Where a nucleic acid is said to hybridize to a recited nucleic acid sequence, hybridization is under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, e.g., at least about 90% as stringent as the above specific stringent conditions.

The term "computer-based system", as used herein refers to the hardware, software, and data storage system used to analyze information. The minimum hardware of a patient computer-based system comprises a central processing unit (CPU), input device, output device, and data storage device. A skilled artisan can readily appreciate that many of the currently available computer-based system are suitable for use in the present invention and may be programmed to perform the specific measurement and/or calculation functions of the methods as disclosed herein.

To "record" data, programming or other information on a computer readable medium refers to a process for storing information, using any such methods as known in the art. Any convenient data storage structure may be chosen, based on the method and/or device used to access the stored information. A variety of data processor programs and formats can be used for storage, e.g. word processing text file, database format, etc.

A "processor" or "computing system" or "computing device" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

As used herein and in the appended claims, the singular forms "a," "an," and "the" include plural referents unless the context clearly dictates otherwise. Thus, for example, reference to "a reference gene" includes a plurality of such genes and reference to "the EGFR inhibitor" includes reference to one or more EGFR inhibitors, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

GENERAL DESCRIPTION

The practice of the methods and compositions of the present disclosure will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Based on evidence of differential expression of a gene (e.g., as detected by assaying for an RNA transcript) in cancer cells that positively respond to an EGFR-inhibitor and non-responsive cancer cells, the present disclosure provides response indicator genes and gene modules. These response indicator genes and/or gene modules and associated information provided by the present disclosure allow physicians to make more intelligent treatment decisions, and to customize the treatment of EGFR-expressing cancer to the needs of individual patients, thereby maximizing the benefit of treatment and minimizing the exposure of patients to unnecessary treatments, which do not provide any significant benefits and often carry serious risks due to toxic side-effects.

The response indicator genes and/or gene modules and associated information provided by the present disclosure have utility in the development of therapies to treat EGFR-expressing cancer and screening patients for inclusion in clinical trials that test the efficacy of EGFR inhibitors. Said genes and/or gene modules and association information may also be used to design or produce a reagent that modulates the level or activity of the gene's transcript (i.e., RNA transcript) or its expression product. Said reagents may include but are not limited to an antisense RNA, a small inhibitory RNA, a ribozyme, a monoclonal or polyclonal antibody.

In various embodiments of the methods of the present disclosure, various technological approaches are available for determination of expression levels of the disclosed genes, including, without limitation, RT-PCR, microarrays, serial analysis of gene expression (SAGE) and nucleic acid sequencing, which will be discussed in detail below. In particular embodiments, the expression level of each gene may be determined in relation to various features of the expression products of the gene including exons, introns, protein epitopes and protein activity EGFR Inhibitor Treatment The present disclosure provides methods to predict the likelihood that a patient having an EGFR-expressing cancer will exhibit a beneficial response to an EGFR inhibitor therapy. Patients subject to such an assessment include: 1) patients who have an EGFR-expressing cancer and who have not yet undergone any treatment for the cancer; 2) patients who have an EGFR-expressing cancer and who have undergone complete or partial resection of the cancer, e.g., who have undergone surgical removal of cancerous tissues to the extent clinically possible; and 3) patients who have an EGFR-expressing cancer and who have been treated with a treatment regimen other than an EGFR inhibitor treatment regimen. Patients who are subject to a likelihood assessment as disclosed herein also include those whose cancer is KRAS-negative (e.g., patients who have a (KRAS⁻) tumor).

It will be appreciated that the same patient sample, and even the same assay, may be used for both determining whether a cancer is an EGFR-expressing cancer and assessing the likelihood that the patient having an EGFR-expressing cancer will exhibit a beneficial response to an EGFR inhibitor cancer therapy. For example, the assay(s) used to determine whether the cancer is an EGFR-expressing cancer may be carried out at the same time as the assay(s) used to assess the likelihood that the patient having an EGFR-expressing cancer will exhibit a beneficial response to an EGFR inhibitor. Alternatively, the result of the assay(s) used to determine whether the cancer is an EGFR-expressing cancer may guide the decision as to whether and how to apply an additional assay(s) used to assess the likelihood that the patient having an EGFR-expressing cancer will exhibit a beneficial response to an EGFR inhibitor.

EGFR-expressing cancers include cancers comprising cells that express an EGFR on their cell surface. Such cancers include, but are not limited to, breast cancer, lung cancer, colorectal cancer, renal cancer prostate cancer, brain cancer, liver cancer, pancreatic cancer, and head and neck cancer.

A patient who is being assessed using the method disclosed in the present disclosure is one who may be considered for treatment with an EGFR inhibitor. EGFR inhibitors include, e.g., antibodies that bind to and inhibit EGFR, EGFR-selective tyrosine kinase inhibitors, and the like. EGFR inhibitors include, but are not limited to, cetuximab (Erbitux®) and panitumumab (Vectibix®), both monoclonal antibodies that block EGFR and EGFR-dependent cell growth; gefitinib (Iressa®; N-(3-chloro-4-fluoro-phenyl)-7-methoxy-6-(3-morpholin-4-ylpropoxy)quinazolin-4-amine); OSI774 (erlotinib, Tarceva®; N-(3-ethynylphenyl)-6,7-bis(2-methoxyethoxy) quinazolin-4-amine); and alpha-cyano-beta-methyl-N-[(trifluoromethoxy)phenyl]-propenamide (LFM-A12), all small molecule tyrosine kinase inhibitors; and the like. Erbitux is a registered trademark of Bristol-Myers Squibb Co. Vectibix is a registered trademark of Amgen, Inc. kressa is a registered trademark of AstraZeneca. Tarceva is a registered trademark of Genentech, Inc.

EGFR inhibitors also include EGFR tyrosine kinase inhibitors such as quinazolines, such as PD 153035 (Fry et al. (1994) *Science* 265:1093; and Traxler et al. (1997) *J. Pharm. Belg.* 52:1997), 4-(3-chloroanilino) quinazoline, or CP-358, 774; pyrrolopyrimidines, such as CGP 59326, CGP 60261 and CGP 62706 (Traxler et al. (1997) *J. Pharm. Belg.* 52:1997); pyrazolopyrimidines (Strawn and Shawver (April 1998) *Exp. Opin. Invest. Drugs* 7:553-573); 4-(phenylamino)-7H-pyrrolo[2,3-d]pyrimidines (Traxler et al., (1996) *J. Med. Chem.* 39:2285-2292); curcumin (diferuloyl methane) (Laxminarayana, et al., (1995), *Carcinogen* 16:1741-1745); 4,5-bis(4-fluoroanilino)phthalimide (Buchdunger et al. (1995) *Clin. Cancer Res.* 1:813-821; Dinney et al. (1997) *Clin. Cancer Res.* 3:161-168); tyrphostins containing nitrothiophene moieties (Brunton et al. (1996) *Anti Cancer Drug Design* 11:265-295); the protein kinase inhibitor ZD-1839 (AstraZeneca) (U.S. Pat. No. 5,770,599; Strawn and Shawver (April 1998) *Exp. Opin. Invest. Drugs* 7:553-573; and Woodburn et al. (1997) Abstract #4251, *Proc. Am. Assoc. Cancer Res.* 38:633); CP-358774 (Pfizer, Inc.) (Moyer et al. (1997) *Cancer Res.* 57:4838); PD-0183805 (Warner-Lambert); inhibitors as described in International patent application WO99/09016 (American Cyanamid); WO98/43960 (American Cyanamid); WO97/38983 (Warner Lambert); WO99/06378 (Warner Lambert); WO99/06396 (Warner Lambert); WO96/30347 (Pfizer, Inc.); WO96/33978 (AstraZeneca); WO96/33977 (AstraZeneca); and WO96/33980 (AstraZeneca).

Methods to Predict Likelihood of Response to EGFR Inhibitor Treatment

The present disclosure provides methods to predict the likelihood that a patient having an EGFR-expressing cancer will exhibit a beneficial response to an EGFR inhibitor therapy. The methods generally involve determining a normalized expression level of a gene or gene product that correlates with EGFR inhibitor responsiveness. Genes that correlate with EGFR inhibitor responsiveness are referred to herein as "response indicator genes."

As discussed in more detail below, a normalized level of one or more response indicator genes can be determined.

Particular mutations in a k-ras gene result in constitutive activation of protein encoded by k-ras. The presence of such activating mutations correlates with patient response to EGFR inhibitor treatment. Khambata-Ford et al. (2007) *Clin. Oncol.* 25:3230; Lievre et al. (2008) *J. Clin. Oncol.* 26:374; WO 2006/086777; and WO 2007/001868. Mutations in a k-ras gene that result in constitutive activation of the k-ras-encoded protein are referred to herein as "KRAS mutations" or "activating KRAS mutations." Detection of activating KRAS mutations can be carried out in conjunction with determination of normalized levels of one or more response indicator genes. Thus, the present disclosure provides methods to predict the likelihood that a patient will exhibit a beneficial response to treatment with an EGFR inhibitor, where the method involves: a) detecting a KRAS mutation in a tumor sample obtained from the patient; and b) determining a normalized level of a response indicator gene(s).

In carrying out a subject method, a level of a response indicator gene, or its gene product, in a tumor sample from a patient is assayed. The level of the response indicator gene, or its gene product, is then "normalized," generating a normalized expression level. A number of response indicator genes were identified. The normalized expression levels of these response indicator genes correlate, positively or negatively, with beneficial patient response to EGFR inhibitor treatment. Thus, normalized expression levels of one or more of these response indicator genes can be determined to assess the likelihood that a patient having an EGFR-expressing cancer will exhibit a beneficial response to an EGFR inhibitor therapy. Response indicator genes are identified as described in detail below and in the Examples.

Response indicator genes of the present disclosure include: ATP5E, TITF1, CLTC, BRCA1, AREG, PTP4A3, EREG, VAV3, SATB2, CEACAM6, EGFR, CHN2, FGFR3, C13orf18, QPRT, AMACR1, CKMT2, ID1, SORBS1, SLC26A3, and ErbB3, and one or more of these may be measured in order to assess the likelihood of beneficial response. Normalized expression levels of each of these genes are positively correlated with beneficial response to EGFR inhibitor treatment. In other words, normalized expression levels of these genes positively correlate with likelihood that a patient will exhibit a beneficial response to EGFR inhibitor treatment.

Response indicator genes of the present disclosure include: DUSP6, VDAC2, ANXA2P2, SERPINB1, NT5E, GPC3, DUSP4, PHLDA1, K-ras, DR5, VIL2, LAMC2, SFN, ANXA1, EPHA2, P14ARF, CA9, KRT17, p14ARF, Maspin, PLAUR, LAMA3, and GCNT3, and one or more of these may be measured in order to assess the likelihood of beneficial response. Normalized expression levels of each of these genes are negatively correlated with beneficial response to EGFR inhibitor treatment. In other words, normalized expression levels of these genes indicate a decreased likelihood that a patient will exhibit a beneficial response to EGFR inhibitor treatment.

Response indicator genes of the present disclosure include: EGF, ADAM17, PTP4A3, ADAM15, QPRT, SATB2, RASSF1, VAV3, CEACAM6, EREG, AREG, TITF1, SORBS1, C13orf18, CKMT2, BTC, ATP5E, B.Catenin, CCNE1, EGFR, Bclx, BRCA1, CDC25B, CHN2, ID1, and SLC26A3, and one or more of these may be measured in order to assess the likelihood of beneficial response. Normalized expression levels of each of these genes are positively correlated with beneficial response to EGFR inhibitor treatment. In other words, normalized expression levels of these genes positively correlate with likelihood that a patient will exhibit a beneficial response to EGFR inhibitor treatment. These response indicator genes can be of particular interest in assessment of patients with KRAS-negative tumors.

Response indicator genes of the present disclosure include: VDAC2, SERPINB1, PHLDA1, ANXA2P2, KRT17, EPHA2, DUSP4, CGA, CA9, Maspin, NEDD8, DUSP6, GPC3, NT5E, VIL2, and P14ARF, and one or more of these may be measured in order to assess the likelihood of beneficial response. Normalized expression levels of each of these genes are negatively correlated with beneficial response to EGFR inhibitor treatment. In other words, normalized expression levels of these genes indicate a decreased likelihood that a patient will exhibit a beneficial response to EGFR inhibitor treatment. These response indicator genes can be of particular interest in assessment of patients with KRAS-negative tumors.

Assessing Likelihood of an Individual Patient's Beneficial Response to EGFR Inhibitor Treatment As described above, a number of response indicator genes were identified in multi-patient studies. Normalized levels of these indicator gene products can then be determined in an individual patient who has cancer and for whom treatment with an EGFR inhibitor is being contemplated. Depending on the outcome of the assessment, treatment with an EGFR inhibitor may be indicated, or an alternative treatment regimen may be indicated.

In carrying out a subject assessment, a tumor sample comprising a response indicator gene is assayed for a level of a response indicator gene or gene product(s). The tumor sample can be obtained from a solid tumor, e.g., via biopsy, or from a surgical procedure carried out to remove a tumor; or from a tissue or bodily fluid that contains cancer cells.

An expression level of a response indicator gene is normalized relative to the level of an expression product of a reference gene(s). Assessing the response likelihood is conducted by comparing the normalized expression level to a range of values of normalized expression levels of one or more reference genes in an EGFR-expressing cancer cell.

Response Indicator Gene Analysis

Normalized expression level of one or more response indicator genes can be carried out to assess the likelihood that a patient will respond to EGFR inhibitor treatment. Thus, this disclosure provides that the normalized expression level of a single or multiple response indicator genes can be used to assess the likelihood that a patient will respond to EGFR inhibitor treatment. The analysis can be more stringent, e.g., the likelihood that a patient will exhibit a beneficial response to an EGFR inhibitor treatment by exhibiting a partial response or a complete response can be assessed. The analysis can be less stringent, e.g., the likelihood that a patient will exhibit a beneficial response to an EGFR inhibitor treatment by exhibiting disease control (DC) can be assessed.

Multi-gene Analysis

It will be appreciated that assessment of likelihood of beneficial response to EGFR inhibitor therapy can be conducted by determining normalized expression levels of a set of response indicator genes, i.e. two or more response indicator genes (e.g., 2, 3, 4, 5, 6, 7, 8, 9, 10, or more response indicator genes), or any combination of one or more sets of response indicator genes. The assessment can involve analyzing expression levels of a combination of response indicator genes, and determining normalized expression levels of the combination of response indicator genes, where the response indicator gene products can include gene products that are positively correlated with clinical benefit and gene products that are negatively correlated with clinical benefit. For example, a normalized level of a first gene that positively correlates with beneficial response to EGFR inhibitor treatment, and a normalized level of a second gene that negatively correlates with beneficial response to EGFR inhibitor treatment, can be determined. The following are non-limiting examples of response indicator genes whose normalized levels can be used in combination, either alone or in combination with other multi-gene response indicator sets, to assess the likelihood of response to EGFR inhibitor treatment:

Exemplary multi-gene sets including two genes: set 1: PHLDA1; PTP4A3; set 2: PHLDA1; AREG; set 3: PHLDA1; EREG set 4: CHN2; PTP4A3; set 5: PTP4A3; SATB2; set 6: EPHA2; AREG; set 7: EPHA2; EREG; set 8: EREG; PTP4A3 set 9: PTP4A3; SLC26A3; set 10: EREG; AREG; set 11: DUSP6; AREG; set 12: DUSP6; EREG; set 13: EGFR; EREG; set 14: SLC26A3; EREG; and set 15: SFN; EREG.

Exemplary multi-gene sets including three genes: set 16: PHLDA1; PTP4A3; AREG; set 17: EGFR; PHLDA1; PTP4A3; set 18: PHLDA1; PTP4A3; SATB2; set 19: AREG; PHLDA1; PTP4A3; set 20: EGFR; PHLDA1; AREG; set 21: EREG; KRT17; PHLDA1; set 22: EREG; PHLDA1; PTP4A3; set 23: EREG; PHLDA1; SATB2; set 24: EREG; PHLDA1; SORBS1; set 25: KRT17; PHLDA1; AREG; set 26: PHLDA1; SATB2; AREG; set 27: AREG; CEACAM6; PHLDA1; set 28: AREG; EGFR; PHLDA1; set 29: DUSP6; PTP4A3; SORBS1; set 30: EGFR; EPHA2; PTP4A3; set 31: EGFR; EREG; PHLDA1; set 32: EREG; KRT17; PTP4A3; set 33: PHLDA1; PTP4A3; SORBS1; set 34: DUSP6; SORBS1; AREG; and set 35: AMACR1; EREG; AREG.

Exemplary multi-gene sets including four genes: set 36: EREG; KRT17; PHLDA1; SORBS1; set 37: AREG; KRT17; PHLDA1; PTP4A3; set 38: EREG; KRT17; PHLDA1; PTP4A3; set 39: AREG; PHLDA1; PTP4A3; SATB2; set 40: EREG; PHLDA1; PTP4A3; SATB2; set 41: AREG; PHLDA1; PTP4A3; SORBS1; set 42: EREG; PHLDA1; PTP4A3; SORBS1; set 43: AREG; EGFR; PHLDA1; PTP4A3; set 44: KRT17; PHLDA1; SORBS1; AREG; set 45: KRT17; PHLDA1; SORBS1; EREG; set 46: CEACAM6; PHLDA1; PTP4A3; AREG; set 47: CEACAM6; PHLDA1; PTP4A3; EREG; set 48: EGFR; PHA2; PHLDA1; AREG; set 49: EGFR; PHA2; PHLDA1; EREG; set 50: EGFR; EREG; KRT17; PHLDA1; set 51: EGFR; EREG; PHLDA1; PTP4A3; set 52: EREG; KRT17; PHLDA1; PTP4A3; set 53: EPHA12; PHLDA1; PTP4A3; AREG; set 54: EPHA12; PHLDA1; PTP4A3; EREG; set 55: EREG; PHLDA1; PLAUR; STAB2; set 56: KRT17; PHLDA1; PTP4A3; SATB2; set 57: DUSP6; EREG; ID1; AREG; set 58: DUSP6; EPHA2; NT5E; AREG; set 59: DUSP6; EPHA2; NT5E;

EREG; set 60: DUSP6; EREG; VIL2; AREG; set 61: DUSP6; EREG; VIL2; EREG; set 62: EPHA2; EREG; GPC3; AREG; set 63: EPHA2; EREG; ID1; AREG; and set 64: DUSP6; EREG; Maspin; AREG.

Additional exemplary multi-gene sets are shown in the Tables 3 and 4. Those skilled in the art will appreciate that normalized levels of any combination of two or more response indicator genes (e.g., two or more response indicator genes as listed in Tables 1A, 1B, 2A, 2B, 6A, 6B, 7A, and 7B) can be determined. It should be noted that, for any of the above-listed exemplary multi-gene sets that include AREG or EREG, AREG or EREG can be substituted with the average of the normalized AREG value and the normalized EREG value.

Further exemplary multi-gene sets include the following sets (e.g., multi-gene sets 65-167) that include two or more genes. These exemplary multi-gene sets find particular use when KRAS mutation status of the subject is taken into account.

Exemplary multi-gene sets including two genes: set 65: PHLDA1; PTP4A3; set 66: KRT17; PTP4A3; set 67: EREG; PHLDA1; set 68: AREG; PHLDA1; set 69: EREG; KRT17; set 70: AREG; KRT17; set 71: KRT17; SERPINB1; set 72: CEACAM6; PTP4A3; set 73: EREG; PTP4A3; set 74: KRT17; SORBS1; set 75: PHLDA1; SORBS1; set 76: SATB2; SERPINB1; set 77: aregereg; PHLDA1; set 78: SLC26A3; AREG; set 79: SLC26A3; EREG; set 80: DUSP6; AREG; set 81: DUSP6; EREG; set 81: VIL2; AREG; set 82: VIL2; EREG; set 83: DR5; AREG; set 84: DR5; EREG; set 85: EPHA2; AREG; set 86: EPHA2; EREG; set 87: EREG; NT5E; set 88: SATB2; AREG; and set 89: SATB2; EREG.

Further exemplary multi-gene sets include the following sets that include three genes: set 90: DUSP6; EREG; SLC26A3; set 91: DUSP6; SLC26A3; EREG; set 92: DUSP6; SLC26A3; AREG; set 93: CA9; EREG; NT5E; set 94: CLTC; DUSP6; AREG; set 95: CLTC; DUSP6; EREG; set 96: DR5; SLC26A3; AREG; set 97: DR5; SCL26A3; EREG; set 98: DUSP6; VIL2; AREG; set 99: DUSP6; VIL2; EREG; set 100: EPHA2; EREG; SLC26A3; set 101: EREG; SLC26A3; VIL2; set 102: KIRT17; SLC26A3; EREG; set 103: KIRT17; SLC26A3; AREG; set 104: SLC26A3; VIL2; AREG; set 105: SLC26A3; VIL2; EREG; set 106: AREG; PHLDA1; PTP4A3; set 107: AREG; KRT17; PHLDA1; set 108: EREG; PHLDA1; SORBS1; set 109: EGFR; PHLDA1; PTP4A3; set 110: KRT17; PTP4A3; SORBS1; set 111: EREG; KRT17; PHLDA1; set 112: PHLDA1; PTP4A3; SORBS1; set 113: ERGF; EREG; PHLDA1; set 114: EREG; PHLDA1; SATB2; set 115: AREG; KRT17; PHLDA1; set 116: CEACAM6; PHLDA1; PTP4A3; set 117: EGFR; EHHA1; EREG; set 118: EREG; KRT17; SLC26A3; set 119: EREG; PHLDA1; PTP4A3; set 120: EREG; PHLDA1; QPRT; and set 121: PHLDA1; PTP4A3; SATB2.

Further exemplary multi-gene sets include the following sets that include four genes: set 122: EREG; KRT17; PHDLA1; SORBS1; set 123: AREG; KRT17; PHLDA1; PTP4A3; set 124: DUSP6; EREG; KRT17; SORBS1; set 125: AREG; KRT17; PHLDA1; PTP4A3; set 126: AREG; KRT17; PHLDA1; PTP4A3; set 127: AREG; PHLDA1; PTP4A3; SORBS1; set 128: AREG; EGFR; EPHA2; PHLDA1; set 129: AREG; CEACAM6; KRT17; SORBS1; set 130: AREG; CEACAM6; KRT17; SORBS1; set 131: AREG; EGFR; KRT17; PHLDA1; set 132: AREG; KRT17; PHLDA1; SORBS1; set 133: AREG; KRT17; PTP4A3; SORBS1; set 134: CEACAM6; EREG; PHDLA1; SORBS1; set 135: CEACAM6; KRT17; PHLDA1; PTP4A3; set 136: CEACAM6; KRT17; PTP4A3; SORBS1; set 137: EGFR; EPHA2; PHLDA2; PTP4A3; set 138: EGFR; EREG; KRT17; PHLDA1; set 139: EGFR; KRT17; PHLDA1; PTP4A3; set 140: EREG; KRT17; PTP4A3; SORBS1; set 141: EREG; LAMA3; PHLDA2; QPRT; set 142 EREG; PHLDA1; PTP4A3; QPRT; set 143: KRT17; PHLDA1; PTP4A3; SORBS1; set 144: KRT17; PTP4A3; SORBS1; VDAC2; set 145: AREG; DR5; DUSP6; SLC26A3; set 146: EREG; DR5; DUSP6; SLC26A3; set 147: AMACR1; AREG; DUSP6; SATB2; set 148: AREG, EREG, SLC26A3, DUSP6; set 149: AREG; CLTC; DUSP6; SLC26A3; set 150: EREG; CLTC; DUSP6; SLC26A3; set 151: AREG; DUSP6; KRT17; SLC26A3; set 152: EREG; DUSP6; KRT17; SLC26A3; and set 153: EGFR; EREG; SLC26A3; VIL2.

Further exemplary multi-gene sets include the following sets that include five genes: set 154: AREG; EGFR; KRT17; PHLDA1; PTP4A3; set 155: AREG; KRT17; PHLDA1; PTP4A3; SORBS1; set 156: AREG; CEACAM6; KRT17; PHLDA1; SORBS1; set 157: EREG; CEACAM6; KRT17; PHLDA1; SORBS1; set 158: AREG; EGFR; KRT17; PHLDA1; PTP4A3; set 159: EREG; EGFR; KRT17; PHLDA1; PTP4A3; set 160: CEACAM6; KRT17; PHLDA1; PTP4A3; SORBS1 set 161: EREG; KRT17; HLDA1; PLAUR; SORBS1. set 162: DUSP6; EREG; QPRT; SLC26A3; VIL2.

Exemplary multi-gene sets including six genes: set 163: AREG; EPHA2; KRT17; LAMC2; PHLDA1; PTP4A3.

Exemplary multi-gene sets including seven genes: set 164: ANXA1; BRCA1; CHN2; PHLDA1; PTP4A3; SORBS1; AREG; set 165: ANXA1; BRCA1; CHN2; PHLDA1; PTP4A3; SORBS1; EREG; set 166: CEACAM6; KRT17; LAMA3; PHLDA1; PTP4A3; SORBS1; AREG; and set 167: CEACAM6; KRT17; LAMA3; PHLDA1; PTP4A3; SORBS1; EREG.

The above-listed multi-gene sets (e.g., multi-gene sets 65-167) are particularly useful in combination with KRAS status, e.g., where the individual is negative for an activating KRAS mutation. The above-listed multi-gene sets are meant to be exemplary only. Those skilled in the art will appreciate that normalized levels of any combination of two or more response indicator genes (e.g., two or more response indicator genes as listed in Tables 1A, 1B, 2A, 2B, 6A, 6B, 7A, and 7B) can be determined. Exemplary multi-gene sets are shown in the Tables 8 and 9. It should be noted that, for any of the above-listed exemplary multi-gene sets that include AREG or EREG, AREG or EREG can be substituted with the average of the normalized AREG value and the normalized EREG value.

K-Ras Mutation Status

As noted above, the presence of an activating mutation in a k-ras gene (a "KRAS mutation") indicates reduced likelihood of a clinically beneficial response to an EGFR inhibitor. The presence or absence of an activating KRAS mutation can be assayed in conjunction with assaying an expression level of a response indicator gene, or its gene product, and determining a normalized expression level of a response indicator gene. Thus, the present disclosure provides methods for assessing the likelihood that a patient will exhibit a beneficial response to EGFR inhibitor treatment, where the method generally involves: a) determining a normalized level of a response indicator gene, or its gene product, in a sample obtained from a tumor sample from the patient; and b) detecting the presence or absence of an activating KRAS mutation. The method will in some cases include a step of assigning a probability of response based on the determined normalized expression level(s) of the one or more response indicator genes. For example, a subject method can involve: a) determining a normalized expression level of one or more response indicator genes in a sample obtained from cancer cells of a patient;

b) determining a KRAS mutation status in a cancer cell from the patient; and, optionally, c) assigning a probability of response based on the determined normalized expression level(s) of the one or more response indicator genes.

Detection of an activating KRAS mutation can be carried out in conjunction with determining a normalized level of a response indicator gene, or its gene product, where "in conjunction with" includes in the same or different sample, and at the same time or at a different time and/or location. For example, the presence or absence of an activating KRAS mutation can be detected in a sample (e.g., a sample comprising a polynucleotide obtained from a patient's cancer cell; or a sample comprising a patient's cancer cell); and a level of a response indicator gene, or its gene product, can be detected in the same sample at substantially the same time and in the same location (e.g., in the same laboratory). Alternatively, the presence or absence of an activating KRAS mutation can be detected in a sample (e.g., a sample comprising a polynucleotide obtained from a patient's cancer cell; or a sample comprising a patient's cancer cell); and a level of a response indicator gene, or its gene product, can be detected in the same sample at substantially the same time and in different locations (e.g., in different laboratories). As another example, the presence or absence of an activating KRAS mutation can be detected in a first sample (e.g., a sample comprising a polynucleotide obtained from a patient's cancer cell) at a first time; and a level of a response indicator gene, or its gene product, can be detected in a second sample (e.g., a sample comprising a polynucleotide obtained from a patient's cancer cell; or a sample comprising a patient's cancer cell) at a second time, where the first and second samples are assayed in the same location. As another example, Alternatively, the presence or absence of an activating KRAS mutation can be detected in a first sample (e.g., a sample comprising a polynucleotide obtained from a patient's cancer cell) at a first time; and a level of a response indicator gene, or its gene product, can be detected in a second sample (e.g., a sample comprising a polynucleotide obtained from a patient's cancer cell; or a sample comprising a patient's cancer cell) at a second time, where the first and second samples are assayed in different locations.

For example, a "KRAS-positive" cancer cell is one that comprises an activating mutation in a k-ras gene; and a "KRAS-positive" patient is one who has a KRAS-positive cancer cell. Conversely, a "KRAS-negative" cancer cell is one that does not comprise an activation mutation in a k-ras gene. For example, a "KRAS-negative" tumor is one in which no activating KRAS mutations are detectable. A "KRAS-negative" patient is one who has a KRAS-negative tumor.

Detection of a KRAS mutation in a tumor sample from the patient or in a sample obtained from a cancer cell from the patient involves detecting a KRAS mutation in a nucleic acid of a cancer cell present in the patient. It is possible, but not necessary, that all cancer cells in the patient comprise a KRAS mutation, e.g., a tumor can be heterogeneous with respect to KRAS mutation status. For example, the KRAS mutation may be present in less than 100%, less than 95%, less than 80%, less than 70%, less than 50%, or less than 25%, of the cancer cells present in the sample and/or in the patient. The presence of an activating KRAS mutation in any proportion of the cancer cells in the sample will indicate that the patient is not likely to respond to EGFR inhibitor treatment.

The presence of an activating KRAS mutation in a k-ras gene of a cancer cell is negatively correlated with a clinically beneficial response to EGFR inhibitor treatment. Exemplary activating mutations are shown in Table 5. Other activating KRAS mutations are found in, e.g., WO 2006/086777 and WO 2007/001868.

As an example, activating KRAS mutations include: 1) a G→T mutation at position 216 of a k-ras nucleotide sequence (e.g., the nucleotide sequence set forth in GenBank Accession No. NM_033360.2); 2) a G→A mutation at position 216 of a k-ras nucleotide sequence; 3) a G→C mutation at position 216 of a k-ras nucleotide sequence; 4) a G→T mutation at position 215 of a k-ras nucleotide sequence; 5) a G→A mutation at position 215 of a k-ras nucleotide sequence; 6) a G→C mutation at position 215 of a k-ras nucleotide sequence; and 7) a G→A mutation at position 219 of a k-ras nucleotide sequence. An example of a KRAS-negative tumor is one that does not include any of the 7 mutations listed above, and shown in Table 5.

The presence of an activating KRAS mutation in a k-ras gene of a cancer cell correlates inversely with clinically beneficial response to EGFR inhibitor treatment.

As noted above, detecting the presence or absence of an activating KRAS mutation can be carried out in combination with assessing a normalized level of a single response indicator gene product, or one or more response gene products, or one or more sets of response indicator gene products. The following are non-limiting examples of possible combinations: 1) KRAS mutation status; PHLDA1 normalized expression level detection; 2) KRAS mutation status; KRT17 normalized expression level detection; 3) KRAS mutation status; SERPINB1 normalized expression level detection; 4) KRAS mutation status; DUSP4 normalized expression level detection; 5) KRAS mutation status; ANXA2P2 normalized expression level detection; 6) KRAS mutation status; EPHA2 normalized expression level detection; 7) KRAS mutation status; PTP4A3 normalized expression level detection; 8) KRAS mutation status; EREG normalized expression level detection; 9) KRAS mutation status; AREG normalized expression level detection; 10) KRAS mutation status; QPRT normalized expression level detection; 11) KRAS mutation status; VAV3 normalized expression level detection; 12) KRAS mutation status; STAB2 normalized expression level detection; and 13) KRAS mutation status; CKMT2 normalized expression level detection.

Additional possible combinations are shown in Tables 6A, 6B, 7A, and 7B.

As noted above, detecting the presence or absence of an activating KRAS mutation (e.g., assessing KRAS mutation status) can be carried out in combination with assaying a normalized level of multiple (e.g., two, three, four, five, six, seven, or more) response indicator gene products. Various possible combinations are depicted in the Tables 8 and 9.

Detection of an activating KRAS mutation can be carried out using any of a variety of methods. Numerous methods are known in the art for detection of sequence variations (polymorphisms and mutations) in nucleic acid samples, and can be used for detecting an activating KRAS mutation. Such methods include methods based on de novo sequencing of nucleic acids as well as methods designed to detect sequence variants (e.g., known variants) at a targeted position in the nucleic acid sequence. Sequence variants are detected using as probes or primers oligonucleotides that hybridize differentially to each variant. Many approaches have been developed to increase the selectivity of hybridization of sequence specific probes to targeted variants; the extent of hybridization of the sequence specific probes is often detected based on detecting and/or quantifying the amount of product formed in a subsequent polymerase chain reaction.

Determining EGFR Inhibitor Responsiveness of an EGFR-Expressing Cancer

The present disclosure provides methods for determining whether an EGFR-expressing cancer is an EGFR inhibitor-responsive or EGFR inhibitor-non-responsive cancer. The methods generally involves: a) assaying a test sample obtained from an EGFR-expressing tumor sample of the patient and determining a normalized expression level of: i) a response indicator gene, or its gene product, that correlates positively with EGFR inhibitor responsiveness, wherein the positively correlating response indicator gene is one or more of ATP5E, TITF1, CLTC, BRCA1, AREG, PTP4A3, EREG, VAV3, SATB2, CEACAM6, EGFR, CHN2, FGFR3, C13orf18, QPRT, AMACR1, CKMT2, ID1, SORBS1, SLC26A3, and ErbB3; and/or ii) a response indicator gene, or its gene product, that correlates negatively with EGFR inhibitor responsiveness, wherein the negatively correlating response indicator is one or more of DUSP6, VDAC2, ANXA2P2, SERPINB1, NT5E, GPC3, DUSP4, PHLDA1, K-ras, DR5, VIL2, LAMC2, SFN, ANXA1, EPHA2, P14ARF, CA9, KRT17, p14ARF, Maspin, PLAUR, LAMA3, and GCNT3, wherein the normalized expression level of the one or more response indicator genes indicates that the EGFR-expressing cancer in a patient is likely to exhibit sensitivity or resistance to treatment with an EGFR inhibitor.

The methods of the present disclosure are particularly useful when the EGFR-expressing cancer is a KRAS-negative cancer. The methods generally involve: a) assaying a test sample obtained from an EGFR-expressing tumor sample from the patient and determining a normalized expression level of: i) a response indicator gene, or its gene product, that correlates positively with EGFR inhibitor responsiveness, wherein the positively correlating response indicator gene is a product of one or more of EGF, ADAM17, PTP4A3, ADAM15, QPRT, SATB2, RASSF1, VAV3, CEACAM6, EREG, AREG, TITF1, SORBS1, C13orf18, CKMT2, BTC, ATP5E, beta-Catenin (also referred to herein as "B.Catenin"), CCNE1, EGFR, Bclx, BRCA1, CDC25B, CHN2, ID1, and SLC26A3; and/or ii) a response indicator gene, or its gene product, that correlates negatively with EGFR inhibitor responsiveness, wherein the negatively correlating response indicator gene is one or more of VDAC2, SERPINB1, PHLDA1, ANXA2P2, KRT17, EPHA2, DUSP4, CGA, CA9, Maspin, NEDD8, DUSP6, GPC3, NT5E, VIL2, and P14ARF, wherein the normalized expression level of the one or more response indicator genes indicates that the EGFR-expressing cancer in a patient is likely to exhibit sensitivity or resistance to treatment with an EGFR inhibitor.

The method can involve determining a normalized expression level of a set of response indicator genes, where exemplary sets are described above. Also as described above, the method can also include determining the presence or the absence of an activating KRAS mutation in nucleic acid obtained from a EGFR-expressing tumor sample.

Methods of Assaying Expression Levels of a Gene Product

The methods and compositions of the present disclosure will employ, unless otherwise indicated, conventional techniques of molecular biology (including recombinant techniques), microbiology, cell biology, and biochemistry, which are within the skill of the art. Exemplary techniques are explained fully in the literature, such as, "Molecular Cloning: A Laboratory Manual", 2$^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4$^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Methods of gene expression profiling include methods based on hybridization analysis of polynucleotides, methods based on sequencing of polynucleotides, and proteomics-based methods. Exemplary methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and PCR-based methods, such as reverse transcription PCT (RT-PCR) (Weis et al., Trends in Genetics 8:263-264 (1992)). Antibodies may be employed that can recognize sequence-specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

Reverse Transcriptase PCR(RT-PCR)

Typically, mRNA is isolated from a test sample. The starting material is typically total RNA isolated from a human tumor, usually from a primary tumor. Optionally, normal tissues from the same patient can be used as an internal control. mRNA can be extracted from a tissue sample, e.g., from a sample that is fresh, frozen (e.g. fresh frozen), or paraffin-embedded and fixed (e.g. formalin-fixed).

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andrés et al., BioTechniques 18:42044 (1995). In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include Master-Pure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

The sample containing the RNA is then subjected to reverse transcription to produce cDNA from the RNA template, followed by exponential amplification in a PCR reaction. The two most commonly used reverse transcriptase enzymes are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

PCR-based methods use a thermostable DNA-dependent DNA polymerase, such as a Taq DNA polymerase. For example, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction product. A third oligonucleotide, or probe, can be designed to facilitate detection of a nucleotide sequence of the amplicon located between the hybridization sites the two PCR primers. The probe can be detectably labeled, e.g., with a reporter dye, and can further be provided with both a fluorescent dye, and a quencher fluorescent dye, as in a Taqman® probe configuration. Where a Taqman® probe is used, during the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as a threshold cycle ("$C_t$"). Fluorescence values are recorded during every cycle and represent the amount of product amplified to that point in the amplification reaction. The threshold cycle ($C_t$) is generally described as the point when the fluorescent signal is first recorded as statistically significant.

To minimize errors and the effect of sample-to-sample variation, RT-PCR is usually performed using an internal standard. The ideal internal standard gene (also referred to as a reference gene) is expressed at a constant level among cancerous and non-cancerous tissue of the same origin (i.e., a level that is not significantly different among normal and cancerous tissues), and is not significantly unaffected by the experimental treatment (i.e., does not exhibit a significant difference in expression level in the relevant tissue as a result of exposure to chemotherapy). For example, reference genes useful in the methods disclosed herein should not exhibit significantly different expression levels in cancerous colon as compared to normal colon tissue. RNAs most frequently used to normalize patterns of gene expression are mRNAs for the housekeeping genes glyceraldehyde-3-phosphate-dehydrogenase (GAPDH) and β-actin. Exemplary reference genes used for normalization comprise one or more of the following genes: ATP5E, GPX1, PGK1, UBB, and VDAC2. Gene expression measurements can be normalized relative to the mean of one or more (e.g., 2, 3, 4, 5, or more) reference genes. Reference-normalized expression measurements can range from 0 to 15, where a one unit increase generally reflects a 2-fold increase in RNA quantity.

Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Res. 6:986-994 (1996).

The steps of a representative protocol for use in the methods of the present disclosure use fixed, paraffin-embedded tissues as the RNA source. mRNA isolation, purification, primer extension and amplification can be preformed according to methods available in the art. (see, e.g., Godfrey et al. J. Molec. Diagnostics 2: 84-91 (2000); Specht et al., Am. J. Pathol. 158: 419-29 (2001)). Briefly, a representative process starts with cutting about 10 μm thick sections of paraffin-embedded tumor tissue samples. The RNA is then extracted, and protein and DNA depleted from the RNA-containing sample. After analysis of the RNA concentration, RNA is reverse transcribed using gene specific primers followed by RT-PCR to provide for cDNA amplification products.

Design of Intron-Based PCR Primers and Probes

PCR primers and probes can be designed based upon exon or intron sequences present in the mRNA transcript of the gene of interest. Primer/probe design can be performed using publicly available software, such as the DNA BLAT software developed by Kent, W. J., Genome Res. 12(4):656-64 (2002), or by the BLAST software including its variations.

Where necessary or desired, repetitive sequences of the target sequence can be masked to mitigate non-specific signals. Exemplary tools to accomplish this include the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Rrawetz S, Misener S (eds.) Bioinformatics Methods and Protocols: Methods in Molecular Biology. Humana Press, Totowa, N.J., pp 365-386).

Other factors that can influence PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases, and exhibit Tm's between 50 and 80° C., e.g. about 50 to 70° C.

For further guidelines for PCR primer and probe design see, e.g. Dieffenbach, C W. et al, "General Concepts for PCR Primer Design" in: PCR Primer, A Laboratory Manual, Cold Spring Harbor Laboratory Press, New York, 1995, pp. 133-155; Innis and Gelfand, "Optimization of PCRs" in: PCR Protocols, A Guide to Methods and Applications, CRC Press, London, 1994, pp. 5-11; and Plasterer, T. N. Primerselect: Primer and probe design. Methods Mol. Biol. 70:520-527 (1997), the entire disclosures of which are hereby expressly incorporated by reference.

Tables A and B provide further information concerning the primer, probe, and amplicon sequences associated with the Examples disclosed herein.

MassARRAY® System

In MassARRAY-based methods, such as the exemplary method developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derived PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details see, e.g. Ding and Cantor, Proc. Natl. Acad. Sci. USA 100:3059-3064 (2003).

Other PCR-Based Methods

Further PCR-based techniques that can find use in the methods disclosed herein include, for example, BeadArray® technology (Illumina, San Diego, Calif.; Oliphant et al., Discovery of Markers for Disease (Supplement to Biotechniques), June 2002; Ferguson et al., Analytical Chemistry 72:5618 (2000)); BeadsArray for Detection of Gene Expression® (BADGE), using the commercially available Luminex 100 LabMAP® system and multiple color-coded microspheres (Luminex Corp., Austin, Tex.) in a rapid assay for gene expression (Yang et al., Genome Res. 11:1888-1898 (2001)); and high coverage expression profiling (HiCEP) analysis (Fukumura et al., Nucl. Acids. Res. 31(16) e94 (2003).

Microarrays

Expression levels of a gene of interest can also be assessed using the microarray technique. In this method, polynucleotide sequences of interest (including cDNAs and oligonucleotides) are arrayed on a substrate. The arrayed sequences are then contacted under conditions suitable for specific hybridization with detectably labeled cDNA generated from mRNA of a test sample. As in the RT-PCR method, the source of mRNA typically is total RNA isolated from a tumor sample, and optionally from normal tissue of the same patient as an internal control or cell lines. mRNA can be extracted, for example, from frozen or archived paraffin-embedded and fixed (e.g. formalin-fixed) tissue samples.

For example, PCR amplified inserts of cDNA clones of a gene to be assayed are applied to a substrate in a dense array. Usually at least 10,000 nucleotide sequences are applied to the substrate. For example, the microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After washing under stringent conditions to remove non-specifically bound probes, the chip is scanned by confocal laser microscopy or by another detection method, such as a CCD camera. Quantitation of hybridization of each arrayed element allows for assessment of corresponding mRNA abundance.

With dual color fluorescence, separately labeled cDNA probes generated from two sources of RNA are hybridized pair wise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et at, Proc. Natl. Acad. Sci. USA 93(2):106-149 (1996)). Microarray analysis can be performed by commercially available equipment, following manufacturer's protocols, such as by using the Affymetrix GenChip® technology.

Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484-487 (1995); and Velculescu et al., Cell 88:243-51 (1997).

Gene Expression Analysis by Nucleic Acid Sequencing

Nucleic acid sequencing technologies are suitable methods for analysis of gene expression. The principle underlying these methods is that the number of times a cDNA sequence is detected in a sample is directly related to the relative expression of the mRNA corresponding to that sequence. These methods are sometimes referred to by the term Digital Gene Expression (DGE) to reflect the discrete numeric property of the resulting data. Early methods applying this principle were Serial Analysis of Gene Expression (SAGE) and Massively Parallel Signature Sequencing (MPSS). See, e.g., S. Brenner, et al., Nature Biotechnology 18(6):630-634 (2000). More recently, the advent of "next-generation" sequencing technologies has made DGE simpler, higher throughput, and more affordable. As a result, more laboratories are able to utilize DGE to screen the expression of more genes in more individual patient samples than previously possible. See, e.g., J. Marioni, Genome Research 18(9):1509-1517 (2008); R. Morin, Genome Research 18(4):610-621 (2008); A. Mortazavi, Nature Methods 5(7):621-628 (2008); N. Cloonan, Nature Methods 5(7):613-619 (2008).

Isolating RNA from Body Fluids

Methods of isolating RNA for expression analysis from blood, plasma and serum (See for example, Tsui N B et al. (2002) 48, 1647-53 and references cited therein) and from urine (See for example, Boom R et al. (1990) J Clin Microbiol. 28, 495-503 and reference cited therein) have been described.

Immunochemical Methods

Immunochemical (also referred to herein as "immunological") methods are also suitable for detecting the expression levels of genes and applied to the method disclosed herein. Antibodies (e.g., monoclonal antibodies) that specifically bind a gene product of a gene of interest can be used in such methods. The antibodies can be detected by direct labeling of the antibodies themselves, for example, with radioactive labels, fluorescent labels, haptene labels such as, biotin, or an enzyme such as horse radish peroxidase or alkaline phosphatase. Alternatively, unlabeled primary antibody can be used in conjunction with a labeled secondary antibody specific for the primary antibody. Immunochemical protocols and kits are well known in the art and are commercially available. Exemplary suitable immunochemical methods include enzyme-linked immunosorbent assays, radioimmunoassays, protein blot methods (also referred to as "Western" blot methods), and enzyme immunoassays.

Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics.

General Description of the mRNA Isolation, Purification and Amplification

The steps of a representative protocol for profiling gene expression using fixed, paraffin-embedded tissues as the RNA source, including mRNA isolation, purification, primer extension and amplification are provided in various published journal articles. (See, e.g., T. E. Godfrey et al., J. Molec. Diagnostics 2: 84-91 (2000); K. Specht et al., Am. J. Pathol. 158: 419-29 (2001), M. Cronin, et al., Am J Pathol 164:35-42 (2004)). Briefly, a representative process starts with cutting a tissue sample section (e.g. about 10 μm thick sections of a paraffin-embedded tumor tissue sample). The RNA is then extracted, and protein and DNA are removed. After analysis of the RNA concentration, RNA repair is performed if desired. The sample can then be subjected to analysis, e.g., by reverse transcribed using gene specific promoters followed by RT-PCR.

Determining a Normalized Level of a Gene Product

As discussed above, the expression level of a response indicator gene is normalized, thereby providing a normalized value. The expression level of a response indicator gene may be normalized relative to the level of an expression product of a reference gene(s).

For example, the expression level of a response indicator gene can be normalized relative to the mean level of gene products of one or more reference genes. As an example, the expression level of a response indicator gene can be normalized relative to the mean level of gene products of all assayed genes, or a subset of the assayed genes, where a subset of the assayed genes can include 1, 2, 3, 4, 5, 6, 7, 8, 9, or more assayed genes.

The expression level of a response indicator gene can be normalized relative to the mean level of the gene products of all of the genes, or a subset of the gene, listed in one or more of Table 1A, Table 1B, Table 2A, Table 2B, Table 6A, Table 6B, Table 7A, and Table 7B. As one non-limiting example, the expression level of a response indicator gene can be normalized to the mean expression level of the following reference genes: ATP5E, PGK1, UBB, VDAC2, and GPX1. Those skilled in the art will readily appreciate that other combinations of genes can be used as reference genes for the purposes of determining a normalized level of a response indicator gene, or its gene product.

Additional suitable reference genes include, but are not limited to, glyceraldehyde-3-phosphate dehydrogenase (GAPDH) (see, e.g., GenBank Accession No. NM_002046; phosphoglycerate kinase 1 (see, e.g., GenBank Accession No. NM_000291); lactate dehydrogenase A (see, e.g., GenBank Accession No. NM_-005566); ribosomal protein L32 (see, e.g., GenBank Accession No. NM_000994); ribosomal protein S18 (see, e.g., GenBank Accession No. NM_022551); tubulin, beta polypeptide (TUBB) (see, e.g., GenBank Accession No. NM_001069); and beta actin (see, e.g., GenBank Accession No. NM_001101). See, e.g., Eisenberg and Levanon (2003) Trends in Genetics 19:362, for a list of additional suitable reference genes.

The level of an RNA transcript as measured by TaqMan® RT-PCR refers to the cycle threshold ($C_t$) value. The lower the $C_t$, the greater the amount of mRNA present in the sample (Relative Quantitation Using Comparative $C_t$; Getting Started Guide, Applied Biosystems, Inc., Part Number 436-4016 Rev. C, 11/2007). The expression value of a RNA transcript in a sample is normalized, e.g., by first determining the mean expression value in Ct of designated reference genes in a sample ($C_{tRef}$). The normalized expression value for a gene ($C_{tGene}$) is then calculated as $C_{tGene} - C_{tRef}$. Optionally, the normalized expression values for all genes can be adjusted, e.g., so that all adjusted normalized Ct have a value >0.

Determining a Probability of Beneficial Response

A normalized level of a response indicator gene, or its gene product, determined for an individual patient can be compared to normalized expression level values for said response indicator gene determined in a population of patients for which the clinical outcome is already known in order to determine an individual patient's probability of beneficial response to EGFR inhibitor therapy. Normalized expression level values (e.g., expressed as $C_t$) correlated with a probability can be used. For example, a normalized level of a response indicator gene, or its gene product, can be compared graphically as shown in FIGS. 3A-10D, to determine the probability of beneficial response to EGFR inhibitor therapy.

The analyses and determinations described herein in connection with a subject method for assessing likelihood of response can be made without the need for assessing any change in the level of a response indicator gene over time.

Analysis Results Reporting

As discussed above, the likelihood that a patient will exhibit a beneficial response to an EGFR inhibitor is assessed by determining a normalized expression level of a response indicator gene or set response indicator genes. The patient's likelihood of response to EGFR inhibitor treatment is provided in a report. The report may further include information regarding the patient's likelihood of response. For example, a subject method can further include a step of generating or outputting a report providing the results of a subject response likelihood assessment, which report can be provided in the form of an electronic medium (e.g., an electronic display on a computer monitor), or in the form of a tangible medium (e.g., a report printed on paper or other tangible medium).

An assessment as to the likelihood that a patient having an EGFR-expressing cancer will respond to treatment with an EGFR inhibitor is referred to below as a "response likelihood assessment" or, simply, "likelihood assessment." A person or entity who prepares a report ("report generator") will also perform the likelihood assessment. The report generator may also perform one or more of sample gathering, sample processing, and data generation, e.g., the report generator may also perform one or more of: a) sample gathering; b) sample processing; c) measuring a level of an indicator response gene product(s); d) measuring a level of a reference gene product(s); e) detecting the presence or absence of an activating KRAS mutation; and f) determining a normalized level of a response indicator gene, or its gene product,(s). Alternatively, an entity other than the report generator can perform one or more sample gathering, sample processing, and data generation.

The person or entity to whom a report is transmitted may be the same person or entity who does one or more of the following: a) collects a sample; b) processes a sample; c) provides a sample or a processed sample; and d) generates data (e.g., level of a response indicator gene, or its gene product,(s); level of a reference gene product(s); normalized level of a response indicator gene, or its gene product,(s)) for use in the likelihood assessment. In some cases, the person(s) or entity(ies) who provides sample collection and/or sample processing and/or data generation, and the person who receives the results and/or report may be different persons, but are both referred to as "users" or "clients" herein to avoid confusion.

In embodiments where the user only executes a portion of the method, the individual who, after computerized data processing according to the methods of the invention, reviews data output (e.g., results prior to release to provide a complete report, a complete, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

Report

A "report," as described herein, is an electronic or tangible document which includes report elements that provide information of interest relating to a subject likelihood assessment and its results. A subject report includes at least a likelihood assessment, e.g., an indication as to the likelihood that a patient having an EGFR-expressing cancer will exhibit a beneficial clinical response to an EGFR inhibitor treatment regimen. A subject report can be completely or partially electronically generated. A subject report can further include one or more of: 1) information regarding the testing facility; 2) service provider information; 3) patient data; 4) sample data; 5) an interpretive report, which can include various information including: a) indication; b) test data, where test data can include: i) normalized level of one or more response indicator gene products; and/or ii) presence or absence of an activating KRAS mutation recommendations; and 6) other features.

Where government regulations or other restrictions apply (e.g., requirements by health, malpractice, or liability insurance), all results, whether generated wholly or partially electronically, are subjected to a quality control routine prior to release to the user.

Testing Facility Information

The report can include information about the testing facility, which information is relevant to the hospital, clinic, or laboratory in which sample gathering and/or data generation was conducted. Sample gathering can include obtaining a cancer cell sample from a biopsy, a surgically removed tumor, surgically removed tissue comprising a tumor, or other tissue or bodily fluid from a patient. Data generation can include one or more of: a) measuring a level of a gene product(s) (e.g., an indicator response gene product(s), a reference gene product(s)); b) detecting the presence or absence of an activating KRAS mutation; and c) determination of a normalized level of an indicator response gene product. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents (e.g., kit, etc.) used in the assay, and the like. Report fields with this information can generally be populated using information provided by the user.

Service Provider Information

The report can include information about the service provider, which may be located outside the healthcare facility at which the user is located, or within the healthcare facility. Examples of such information can include the name and location of the service provider, the name of the reviewer, and where necessary or desired the name of the individual who conducted sample gathering and/or data generation. Report fields with this information can generally be populated using data entered by the user, which can be selected from among pre-scripted selections (e.g., using a drop-down menu). Other service provider information in the report can include contact information for technical information about the result and/or about the interpretive report.

Patient Data

The patient data can include patient medical history (which can include, e.g., data about prior treatment for cancer), personal history; administrative patient data (that is, data that are not essential to the likelihood assessment), such as information to identify the patient (e.g., name, patient date of birth (DOB), gender, mailing and/or residence address, medical record number (MRN), room and/or bed number in a healthcare facility), insurance information, and the like), the name of the patient's physician or other health professional who ordered the response likelihood assessment and, if different from the ordering physician, the name of a staff physician who is responsible for the patient's care (e.g., primary care physician). Report fields with this information can generally be populated using data entered by the user.

Sample Data

The sample data can provide information about the biological sample analyzed in the likelihood assessment, such as the source of biological sample obtained from the patient (e.g., tumor biopsy, surgically removed tumor, unknown, etc.) and the date and time collected. Report fields with this information can generally be populated using data entered by the user, some of which may be provided as pre-scripted selections (e.g., using a drop-down menu).

Interpretive Report

The interpretive report portion of the report includes information generated after processing of the data as described herein. The interpretive report can include an indication of the likelihood that the patient will respond to treatment with an EGFR inhibitor. The interpretive report can include, for example, Indication (e.g., type of EGFR-expressing cancer, etc.); Result of screen for KRAS mutation (e.g., "Negative for mutations tested"); Result of normalized level of response indicator gene(s) (e.g., "normalized level of response indicator gene(s)"); Interpretation; and, optionally, Recommendation(s).

The Interpretation portion of the report can include a Recommendation(s). Where the results indicate a likelihood of beneficial response to an EGFR inhibitor treatment, the recommendation can include a recommendation that an EGFR inhibitor regimen is indicated. Where the results indicate that a beneficial response to an EGFR inhibitor treatment is not likely, the recommendation can include a recommendation for an alternative treatment regimen.

It will be readily appreciated that the report can include all or some of the elements above, with the proviso that the report generally includes at least the elements sufficient to provide the analysis requested by the user (e.g., likelihood assessment).

Additional Features

It will also be readily appreciated that the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting.

Computer-Based Systems and Methods

The methods and systems described herein can be implemented in numerous ways. In one embodiment of particular interest, the methods involve use of a communications infrastructure, for example the internet. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility).

For example, during or after data input by the user, portions of the data processing can be performed in the user-side computing environment. For example, the user-side computing environment can be programmed to provide for defined test codes to denote a likelihood "score," where the score is transmitted as processed or partially processed responses to the reviewer's computing environment in the form of test code for subsequent execution of one or more algorithms to provide a results and/or generate a report in the reviewer's computing environment. The score can be a numerical score (representative of a numerical value) or a non-numerical score representative of a numerical value or range of numerical values (e.g., "A" representative of a 90-95% likelihood of an outcome).

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., level of a response gene, level of a reference gene product(s); normalized level of a response gene; and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing of the present invention.

Where used, the database(s) is usually connected to the database server component and can be any device which will hold data. For example, the database can be a any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Computer-Readable Storage Media

The present disclosure also contemplates a computer-readable storage medium (e.g. CD-ROM, memory key, flash memory card, diskette, etc.) having stored thereon a program which, when executed in a computing environment, provides for implementation of algorithms to carry out all or a portion of the results of a response likelihood assessment as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the invention can be packaged with instructions (e.g., for program installation, use, etc.) recorded on a suitable substrate or a web address where such instructions may be obtained. The computer-readable storage medium can also be provided in combination with one or more reagents for carrying out response likelihood assessment (e.g., primers, probes, arrays, or other such kit components).

Multivariate Model Building

The normalized expression levels of response indicator genes can be used in conducting a multivariate analysis so as to construct a multi-gene model useful in assessing a patient's likelihood of EGFR inhibitor treatment response. Thus, the present disclosure provides a method for conducting a multivariate analysis and/or constructing a multi-gene model.

The method generally involves: a) assembling values of normalized expression levels of two or more response indicator gene products; b) determining whether a mathematical combination of the normalized expression levels of any combination of the response indicator genes is more indicative of a likelihood that a patient will respond to treatment with an EGFR inhibitor than the normalized expression level of any one of the response indicator genes individually; and c) using the mathematical combination to assess the likelihood that a patient will respond to treatment with a EGFR inhibitor (Ambroise C and McLachlan G J (2002) Proc Nat Acad Sci USA 99, 6562-6566).

Treatment and Classification Methods

The present disclosure provides treatment methods, which treatment methods generally involve treating an individual having an EGFR-expressing cancer with a treatment regimen that is selected based on the results of a response likelihood assessment as described herein.

The present disclosure also provides a method for classifying a patient as a "responder" or a "non-responder" based on the results of a subject likelihood assessment. For example, the method involves assaying a test sample obtained from an EGFR-expressing cancer cell from a patient; and determining a normalized level of a gene product of a response indicator gene, as described above. The normalized level of the gene product(s) indicate whether the patient is likely to exhibit a clinically beneficial response to treatment with an EGFR inhibitor, thereby allowing classification of the patient as a "responder" or a "non-responder."

Array and Other Compositions for Use in Prediction Methods

The present disclosure provides arrays for use in carrying out a subject method to predict the likelihood of patient beneficial response to EGFR inhibitor treatment.

Arrays (Gene Panels)

The present disclosure provides an array for use in a subject method. A subject array includes a plurality of polynucleotides immobilized on the surface of an insoluble support. The immobilized polynucleotides comprise nucleotide sequences that are capable of hybridizing with a response indicator gene or a reference gene. As used herein, the term "hybridizing" refers to the complementary base-pairing interaction of one nucleic acid with another nucleic acid that results in formation of a duplex, triplex, or other higher-ordered structure. Typically, the primary interaction is base specific, e.g., A/T and G/C, by Watson/Crick hydrogen bonding. Base stacking and hydrophobic interactions can also contribute to duplex stability. Conditions for hybridizing detector probes and primers to complementary and substantially complementary target sequences are known in the art (see e.g., Nucleic Acid Hybridization, A Practical Approach, B. Hames and S. Higgins, eds., IRL Press, Washington, D.C. (1985) and Wetmur J and Davidson N (1968) Mol Biol 31, 349-37.

For example, an immobilized polynucleotide comprises a nucleotide sequence that hybridizes to a response indicator gene selected from a gene listed in one of Table 1A, Table 1B, Table 2A, Table 2B, Table 6A, Table 6B, Table 7A, and Table 7B, above. Nucleotide sequences of the aforementioned response indicator genes are known in the art. As such, generation of probes that hybridize under suitable hybridization conditions (e.g., stringent hybridization conditions) is well within the skill level of those of ordinary skill in the art.

As an example, a subject array can comprise a probe that provides for detection of one or more gene product(s) encoded by a response indicator gene selected from: ATP5E, TITF1, CLTC, BRCA1, AREG, PTP4A3, EREG, VAV3, SATB2, CEACAM6, EGFR, CHN2, FGFR3, C13orf18, QPRT, AMACR1, CKMT2, ID1, SORBS1, SLC26A3, and ErbB3. As another example, a subject array can comprise a probe that provides for detection of one or more gene product(s) encoded by a response indicator gene selected from: DUSP6, VDAC2, ANXA2P2, SERPINB1, NT5E, GPC3, DUSP4, PHLDA1, K-ras, DR5, VIL2, LAMC2, SFN, ANXA1, EPHA2, P14ARF, CA9, KRT17, p14ARF, Maspin, PLAUR, LAMA3, and GCNT3. As yet another example, a subject array can comprise a probe that provides for detection of one or more gene product(s) encoded by a response indicator gene selected from ATP5E, TITF1, CLTC, BRCA1, AREG, PTP4A3, EREG, VAV3, SATB2, CEACAM6, EGFR, CHN2, FGFR3, C13orf18, QPRT, AMACR1, CKMT2, ID1, SORBS1, SLC26A3, ErbB3, DUSP6, VDAC2, ANXA2P2, SERPINB1, NT5E, GPC3, DUSP4, PHLDA1, K-ras, DR5, VIL2, LAMC2, SFN, ANXA1, EPHA2, P14ARF, CA9, KRT17, p14ARF, Maspin, PLAUR, LAMA3, and GCNT3.

As yet another example, a subject array can comprise a probe that provides for detection of one or more gene product(s) encoded by a response indicator gene selected from EGF, ADAM17, PTP4A3, ADAM15, QPRT, SATB2, RASSF1, VAV3, CEACAM6, EREG, AREG, TITF1, SORBS1, C13orf18, CKMT2, BTC, ATPSE, B.Catenin, CCNE1, EGFR, Bclx, BRCA1, CDC25B, CHN2, ID1, SLC26A3, VDAC2, SERPINB1, PHLDA1, ANXA2P2, KRT17, EPHA2, DUSP4, CGA, CA9, Maspin, NEDD8, DUSP6, GPC3, NTSE, VIL2, and P14ARF. Such an array is particularly useful for predicting the likelihood that a patient having an KRAS-negative, EGFR-expressing cancer will exhibit a beneficial response to an EGFR inhibitor therapy.

As yet another example, a subject array can comprise probes that provides for detection of the gene products of genes included in the above-listed multi-gene sets, or any combination of multi-gene sets (e.g., multi-gene sets 1-64 and 65-167, above).

As noted above, in some cases, the presence or absence of an activating KRAS mutation will be detected. In these cases, one or more probes that provide for detection of known activating KRAS mutations are included in the array.

The response indicator genes are represented in the array by probes immobilized on an insoluble support. The response indicator genes (as represented by immobilized probes) represent at least about 25% of the genes represented on the array. For examples, the response indicator gene represent at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, or at least about 95% of the gene represented on the array.

A probe that hybridizes to a response indicator gene is referred to herein as a "response indicator gene probe." Response indicator gene probes are single stranded nucleic acids, having a length of from about 10 nucleotides (nt) to about 100 nt, e.g., from about 15 nt to about 50 nt, from about 15 nt to about 20 nt, from about 20 nt to about 25 nt, or from about 25 nt to about 30 nt. In this context, the term "about" may be construed to mean 1, 2, 3, 4, 5, 6, 7, 8, 9, 10, 11, 12, 13, 14, 15, 16, 17, 18, 19 or 20 more nucleotides either 5' or 3' from either termini or from both termini.

A subject array comprises one or more response indicator gene probes immobilized on a surface of a solid (insoluble) support. A subject array can include two or more ("a plurality") of response indicator gene probes immobilized on a surface of a solid support. For example, a subject array can include 2, 3, 4, 5, 6, 7-10, 10-12, 12-15, 15-20, 20-25, 25-30, 30-35, 35-40, 40-45, 45-50, or more than 50, distinct response indicator gene probes immobilized on a surface of a solid support.

A probe can be "addressable," e.g., the nucleotide sequence, or perhaps other physical or chemical characteristics, of a probe can be determined from its address, i.e. a one-to-one correspondence between the sequence or other property of the probe and a spatial location on, or characteristic of, the solid phase support to which it is attached. For example, an address of a probe can be a spatial location, e.g. the planar coordinates of a particular region containing copies of the probe.

A subject array includes a solid phase support, which may be planar or a collection of microparticles, that carries or carry probes as described above fixed or immobilized, e.g., covalently, at specific addressable locations. For example, a subject array includes a solid phase support having a planar surface, which carries an plurality of nucleic acids, each member of the plurality comprising identical copies of an oligonucleotide or polynucleotide probe immobilized to a fixed region, which does not overlap with those of other members of the plurality. Typically, the nucleic acid probes are single stranded and are covalently attached to the solid phase support at known, determinable, or addressable, locations. The density of non-overlapping regions containing nucleic acids in a microarray is typically greater than 100 per $cm^2$, e.g., greater than 1000 per $cm^2$.

The substrates of the subject arrays may be fabricated from a variety of materials. The materials from which the substrate is fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, is of particular interest in this embodiment. For rigid substrates, specific materials of interest include: glass; plastics. e.g. polytetrafluoroethylene, polypropylene, polystyrene, polycarbonate, and blends thereof, and the like; metals, e.g. gold, platinum, and the like; etc. Also of interest are composite materials, such as glass or plastic coated with a membrane, e.g. nylon or nitrocellulose, etc.

Hybridization between a probe and a test nucleic acid (where a test nucleic acid includes a nucleic acid sample obtained from a cancer cell from a patient) results in a "readout," where "readout" refers to a parameter, or parameters, which are measured and/or detected that can be converted to a number or value. In some contexts, readout may refer to an actual numerical representation of such collected or recorded data. For example, a readout of fluorescent intensity signals from an array is the address and fluorescence intensity of a signal being generated at each hybridization site of the array; thus, such a readout may be registered or stored in various ways, for example, as an image of the array, as a table of numbers, or the like.

The total number of spots on the substrate will vary depending on the number of different oligonucleotide probe spots (oligonucleotide probe compositions) one wishes to display on the surface, as well as the number of non probe spots, e.g., control spots, orientation spots, calibrating spots and the like, as may be desired depending on the particular application in which the subject arrays are to be employed. The pattern present on the surface of the array can include at least 2 distinct nucleic acid probe spots, at least about 5 distinct nucleic acid probe spots, at least about 10 distinct nucleic acid spots, at least about 20 nucleic acid spots, or at least about 50 nucleic acid spots.

In some cases, it may be desirable to have each distinct probe spot or probe composition be presented in duplicate, i.e. so that there are two duplicate probe spots displayed on the array for a given target. In some cases, each target represented on the array surface is only represented by a single type of oligonucleotide probe. In other words, all of the oligonucleotide probes on the array for a give target represented thereon have the same sequence. In certain embodiments, the number of spots will range from about 200 to 1200. The number of probe spots present in the array can make up a substantial proportion of the total number of nucleic acid spots on the array, where in many embodiments the number of probe spots is at least about 25 number %, at least 50 number %, at least about 80 number %, or at least about 90 number % of the total number of nucleic acid spots on the array.

A subject array can be prepared using any convenient methods and compositions. For example, one method of preparing an array is to first synthesize the oligonucleotides for each spot and then deposit the oligonucleotides as a spot on the support surface. The oligonucleotides may be prepared using any convenient methodology, where chemical synthesis procedures using phosphoramidite or analogous protocols in which individual bases are added sequentially without the use of a polymerase, e.g. such as is found in automated solid phase synthesis protocols, where such techniques are well known to those of skill in the art.

Targets (e.g., a nucleic acid sample from a patient's cancer cell) may be generated by methods known in the art. mRNA can be labeled and used directly as a target, or converted to a labeled cDNA target. mRNA can be labeled non-specifically (randomly) directly using chemically, photochemically or enzymatically activated labeling compounds. An mRNA target can be labeled specifically in the sequences which are complementary to the probes. This specific labeling can be achieved by using covalent or non-covalent binding of additional labeled oligonucleotides to the target sequences which flank the probe complementary sequence or the complementary probe sequence. The hybridized fraction of labeled oligonucleotides with mRNA can be purified or separated from the non-hybridized fraction and then hybridized to the array. Methods for generating labeled cDNA probes are known in the art, and include the use of oligonucleotide primers and labeled nucleotide triphosphate(s). Primers that may be employed include oligo(dT), random primers, e.g. random hexamers and gene specific primers.

Following preparation of the target nucleic acid from the tissue or cell of interest, the target nucleic acid is then contacted with the array under hybridization conditions, where such conditions can be adjusted, as desired, to provide for an optimum level of specificity in view of the particular assay being performed. Suitable hybridization conditions are well known to those of skill in the art and reviewed in Maniatis et al, supra, and WO 95/21944. Of particular interest in many embodiments is the use of stringent conditions during hybridization, i.e. conditions that are optimal in terms of rate, yield and stability for specific probe-target hybridization and provide for a minimum of non-specific probe/target interaction. Stringent conditions are known to those of skill in the art.

Following hybridization, non-hybridized labeled nucleic acid is removed from the support surface, conveniently by washing, generating a pattern of hybridized nucleic acid on the substrate surface. A variety of wash solutions are known to those of skill in the art and may be used. Methods of detecting hybridization between a probe nucleic acid and a target nucleic acid include scintillation counting, autoradiography, fluorescence measurement, calorimetric measurement, light emission measurement, light scattering, and the like.

Non-limiting examples of probes that would be suitable for inclusion in a subject array include the probe sequences set forth in the tables provided in FIGS. 1 and 2.

A subject array can be used in a subject method to predict the likelihood that a patient will respond to an EGFR inhibitor treatment. Thus, the present disclosure provides a method to predict the likelihood that a patient having an EGFR-expressing cancer will exhibit a beneficial response to treatment with an EGFR inhibitor, where the method involves: (a) contacting an array comprising a plurality of distinct response indicator gene nucleic acid probes immobilized on a surface of a solid support with a nucleic acid sample from a cancer cell from the patient, to produce a sample contacted array; and (b) detecting hybridization between the immobilized probes and nucleic acids from the patient. Detection of hybridization provides for determination of a normalized level of a response indicator gene, or its gene product, and therefore allows for an assessment as to the likelihood that the patient will exhibit a beneficial response to EGFR inhibitor treatment.

The instant disclosure also provides methods of preparing a subject array. The methods generally involve immobilizing on a solid support one or more probes that provide for detection of nucleic acid products of at least two genes selected from: ATP5E, TITF1, CLTC, BRCA1, AREG, PTP4A3, EREG, VAV3, SATB2, CEACAM6, EGFR, CHN2, FGFR3, C13orf18, QPRT, AMACR1, CKMT2, ID1, SORBS1, SLC26A3, and ErbB3 and/or at least one gene selected from: DUSP6, VDAC2, ANXA2P2, SERPINB1, NT5E, GPC3, DUSP4, PHLDA1, K-ras, DR5, VIL2, LAMC2, SFN, ANXA1, EPHA2, P14ARF, CA9, KRT17, p14ARF, Maspin, PLAUR, LAMA3, and GCNT3, where the genes comprise at least 25% of the genes represented on the array.

In some cases, a method of preparing a subject array involves immobilizing on a solid support one or more probes that provide for detection of nucleic acid products of at least two genes selected from: EGF, ADAM17, PTP4A3, ADAM15, QPRT, SATB2, RASSF1, VAV3, CEACAM6, EREG, AREG, TITF1, SORBS1, C13orf18, CKMT2, BTC, ATP5E, B.Catenin, CCNE1, EGFR, Bclx, BRCA1, CDC25B, CHN2, ID1, SLC26A3, VDAC2, SERPINB1, PHLDA1, ANXA2P2, KRT17, EPHA2, DUSP4, CGA, CA9, Maspin, NEDD8, DUSP6, GPC3, NT5E, VIL2, and P14ARF, where the genes comprise at least 25% of the genes represented on the array.

Kits

The materials for use in the methods of the present invention are suited for preparation of kits produced in accordance with well known procedures. The invention thus provides kits comprising reagents, which may include gene-specific or gene-selective probes and/or primers useful for assaying the expression of genes disclosed herein and for assessing the likelihood of response to treatment with EGFR inhibitors.

For example, a subject kit can include one or more nucleic acid probes that hybridize specifically to nucleic acid response indicator gene products. A subject kit can include, e.g., one or more nucleic acid probes, where each of the one or more probes hybridizes specifically to a different response indicator gene product. For example, a subject kit can include probes that hybridize specifically to nucleic acid products of response indicator genes set forth in one or more of Tables 1A, 1B, 2A, 2B, 6A, 6B, 7A, and 7B. As another example, a subject kit can include a set of two or more nucleic acid probes, where each probe of the set hybridizes to a nucleic acid product of a different response indicator gene. For example, a subject kit can include a set of two, three, four, five, six, seven, or more, nucleic acid probes, where each probe of the set hybridizes to a nucleic acid product of a different member of a set of response indicator genes, where exemplary sets of response indicator genes are depicted in Tables 8 and 9. For example, a subject kit can comprise probes that provides for detection of the gene products of genes included in the above-listed multi-gene sets (e.g., multi-gene sets 1-64 and 65-167, above).

In some cases, a subject kit will include, in addition to a probe that hybridizes specifically to a nucleic acid product of a response indicator gene, one or more probes that hybridize specifically to a reference gene product. Such probes can be used in determining normalized expression levels of a response indicator gene.

A subject kit can include one or more nucleic acid primer pairs, where the primer pairs, when used as primers in a polymerase chain reaction, amplify a target nucleic acid response indicator gene product, or a target region of a nucleic acid response indicator gene product. A subject kit can include primer pairs for multiple response indicator genes. For example, a subject kit can include primer pairs that provides for amplification of the gene products of genes included in the above-listed multi-gene sets (e.g., multi-gene sets 1-64 and 65-167, above).

Exemplary sequences of nucleic acid primers and probes are set forth in the tables provided in FIGS. 1 and 2. Those skilled in the art will readily appreciate that other probe and primer sequences are also possible, and are readily obtained based on known nucleotide sequences of response indicator genes, and/or based on known nucleotide sequences of reference genes.

A subject kit can further include one or more nucleic acid probes that hybridize to target nucleic acids (e.g., nucleic acid from a cancer cell obtained from a patient) that may include one or more activating KRAS mutations.

In addition to the above-mentioned probes and primers, a subject kit can comprise reagents for the extraction and/or isolation of RNA from tumor samples, in particular fixed paraffin-embedded tissue samples and/or reagents for preparing a cDNA copy of an mRNA, and/or reagents for nucleic acid amplification.

Primers and probes can be designed based on known sequences of response indicator genes, and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) Tetrahedron 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly (A) or poly(C), or other non-complementary nucleotide extensions may be incorporated into probes using these same methods. Hexaethylene oxide extensions may be coupled to probes by methods known in the art. Cload et al. (1991) J. Am. Chem. Soc. 113:6324-6326; U.S. Pat. No. 4,914,210 to Levenson et al.; Durand et al. (1990) Nucleic Acids Res. 18:6353-6359; and Horn et al. (1986) Tet. Lett. 27:4705-4708.

A probe or a primer can include a detectable label. Exemplary labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM), N,N,N',N'-tetramethyl-6-carboxyrhodamine (TAMRA), Cy5, Cy3, and the like; and radioactive labels (e.g., $^{32}P$, etc.).

Probes and primers for inclusion in a subject kit include those useful in various amplification and/or detection systems. Exemplary amplification and/or detection systems include Sunrise™ primer-based systems, Molecular Beacons, the Taqman™ system, an Amplifluor™ hairpin primer-based system, a Scorpions technology (e.g., bi-functional molecules containing a PCR primer element covalently linked to a probe element), and a Light Upon Extension or LUX™-based system. Further exemplary detection systems include those based on a melt-curve analysis, and using intercalating dyes such as the fluorescent dye SYBR Green.

The kits may optionally comprise reagent(s) with an identifying description or label or instructions relating to their use in the methods of the present invention. The kits may comprise containers (including microtiter plates suitable for use in an automated implementation of the method), each with one or more of the various reagents (typically in concentrated form) utilized in the methods of the invention, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention (e.g., appropriate length poly (T) or random primers linked to a promoter reactive with the RNA polymerase). Instructions for the use of mathematical algorithms used to assess the likelihood of patient response to EGFR inhibitors can also be included in a subject kit.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Identification of Markers of Response to an EGFR Inhibitor in Cancer Patients

Gene products that can serve as predictors of response to an EGFR inhibitor ("response indicator genes") were identified by analyzing normalized levels of gene products from tumors obtained from patients that had undergone cetuximab treatment for colon cancer. Expression levels of the gene products were measured; and normalized levels were determined relative to expression levels of one or more reference genes.

Identification of an response indicator gene product was carried out by analyzing gene expression levels in cancer cells from a number of patients for whom the following criteria applied: 1) the patients had cancer and were treated for the cancer with an EGFR inhibitor; and 2) the outcome of treatment was documented, i.e., the patients' response to treatment was documented.

Nucleic acid from cancer cells from the patients was analyzed to measure the expression level of a test gene(s) and a reference gene(s). The expression level of the test gene(s) was then normalized to the expression level of the reference gene(s), thereby generating a normalized expression level (a "normalized expression value") of the test gene. Normalization was carried out to correct for variation in the absolute level of gene product in a cancer cell.

Finally, statistical correlations were made between normalized expression values of each gene and one or more measures of clinical outcome following EGFR inhibitor treatment that reflect a likelihood of response to treatment with an EGFR inhibitor. Directed by this univariate analysis, statistical methods were used to construct multi-gene models that are predictive of likelihood of response to EGFR inhibitor. The model is an algorithm (or equation) that can be used to produce a recurrence score or a response-to-treatment score for an individual patient that is strongly correlated with the likelihood of response to an EGFR inhibitor in the set of samples utilized for the analysis.

The final algorithm can utilize various manipulations of the normalized expression values such as application of thresholds to the expression value (assigning maximum and/or minimum values to particular genes) grouping genes, taking the average value of genes in a group or weighting the genes within a group, weighting the group as a whole or some combination of the above.

INCLUSION AND EXCLUSION CRITERIA

Inclusion Criteria

Tissue from patients who consented to participate in one of the following studies: a) Clinical Protocol CA225045: "An Exploratory Pharmacogenomic Study of Erbitux Monotherapy in Patients with Metastatic Colorectal Carcinoma" (Khambata-Ford et al. (2007) 25: 3230-3237); b) IMCL CP02-0141: "Phase II Study of an Anti-Epidermal Growth Factor Receptor (EGFR) Antibody, Cetuximab, in Patients with Irinotecan-Refractory, Stage 1V Colorectal Carcinoma" (Saltz et al. (2004) J. Clin. Oncol. 22: 1201-1208); c) IMCL CP02-0144: "A Phase II Multicenter Study of Erbitux (Cetuximab) in Patients with Metastatic Colorectal Carcinoma" (Lenz et al. (2006) J. Clin. Oncol. 24: 4914-4921);

2) Adequate tissue from the primary and/or metastatic site, defined as a minimum of three 5-micron sections on unstained slides Exclusion Criteria a) Insufficient tumor in block as assessed by examination of H&E slide (<5% of total tissue on slide)

b) EGFR inhibitor response data from clinical study is unknown c) Insufficient total RNA yield (<400 ng) extracted from available sections Probes and Primers A total of 65 amplicons were tested representing cancer related genes, reference genes and KRAS mutation assays. The sequences of probes and primers used to assay each amplicon are provided in the table depicted in FIG. 1; and the sequences of the resulting amplicons are provided in the table depicted in FIG. 2.

Identification of Genes that are Indicators of Response to EGFR Inhibitor Treatment A number of tumor samples were collected, e.g., from patients enrolled in clinical trials or from case studies where well-curated clinical outcome were available.

A thin section of each tumor sample was hematoxylin & eosin (H&E) stained. The stained slide was used to evaluate the amount of tumor present. If the tumor amount was low, then macrodissection was carried out using the H&E slide as template. The H&E section was also used to confirm physician diagnosis.

RNA was extracted from additional thin sections of the tumor.

Quality control (QC) steps were carried out to confirm adequate RNA and to confirm the absence of contaminating DNA.

An expression value for each test (and reference) gene was assayed using gene-specific probes and primers in quantitative reverse-transcription PCR. (e.g., TaqMan®), resulting in raw expression values (Ct).

The raw Ct data were normalized, using, e.g., a set of 5 reference genes, resulting in normalized expression values (normalized Ct).

Statistical correlations were made between normalized expression values of each gene and one or more measures of clinical outcome that reflect likelihood of recurrence (univariate analysis), or likelihood of response to EGFR inhibitor.

Directed by the results of univariate analysis, statistical methods were used to construct multi-gene models that are predictive of likelihood of response to EGFR inhibitor. The model is an algorithm (or equation) that can be used to produce a recurrence score or a response-to-treatment score for an individual patient that is strongly correlated with the likelihood of response to an EGFR inhibitor in the set of samples utilized for the analysis.

STATISTICAL METHODS

Reference Normalization

For normalization of extraneous effects, cycle threshold ($C_T$) measurements obtained by RT-PCR were normalized relative to the mean expression of a set of five reference genes: ATP5E, PGK1, UBB, VDAC2, and GPX1. A one unit increase in normalized expression measurements generally reflects a 2-fold increase in RNA quantity.

Univariate Analysis

For each of the genes under study, we used univariate logistic regression models (SAS version 9.1.3) to examine the relationship between gene expression and overall response rate (ORR). For each logistic regression model, we generated a p-value under the likelihood ratio test of the hypothesis that the odds ratio is significantly different from one. The minimum false discovery rate (FDR) at which each null hypothesis could be rejected using the method of Benjamini and Hochberg (Benjamini, Y. and Hochberg, Y. (1995) J. R. *Statist. Soc.* B57:289) was also calculated as a conservative statistical adjustment for multiplicity. All analyses were repeated for the alternative endpoint: Disease Control (DC). To examine the relationship between gene expression and progression free survival (PFS), we used univariate Cox Regression models (SAS version 9.1.3). When examining these relationships gene expression levels were treated as continuous variables. PFS was defined as the time from study entry to the date of first evidence of progression for patients with documented progressive disease, or the date of death for patients who died within 90 days of their last tumor assessment without documented progression. Those who did not progress or die were censored at the date of the last tumor assessment. All hypothesis tests were reported using two-sided p-values, and unadjusted p-values of <0.05 were considered statistically significant.

Derivation of Predicted Probability Plots

Another useful measure of effect size is provided by plots of the predicted probabilities of disease control, estimated using logistic regression modeling, as a function of gene expression measurements. As examples, FIGS. 3A-10D display plots of the predicted probability of disease control (on the y-axis) by normalized gene expression in $C_T$ units (on the x-axis).

Multivariate Analysis

Because KRAS mutation status is strongly associated with ORR, we chose to build multigene models in two ways 1) utilizing all patients in model building but including interaction terms between KRAS mutation status and individual gene expression and 2) using the subset of wild type patients (n=144) to identify genes beyond KRAS mutation status that would be predictive of response to cetuximab therapy. In the first scenario, we captured how the KRAS mutation status modifies the relationship of gene expression and outcome by including all possible one-way interaction terms between each individual gene and KRAS mutation status. We followed a supervised approach using only a subset of genes that were identified as significantly associated with outcome based on univariate analyses in all patients for scenario 1. Similarly, we utilized a supervised approach using only a subset of genes that were identified as significantly associated with outcome based on univariate analyses in the subset of wild type patients in scenario 2. To build these models we performed two-layer 5-fold cross-validation separately for scenarios 1 and 2 as follows:

Derivation of Multivariate Models

Derivation of multivariate models was carried out according to the following steps:

1) The data were randomly partitioned into 5 equal subsets A-E (outer layer). 2) The data from 4 outer layer subsets were pooled (Subsets B-E in the example below) and these data were partitioned into 5 equal subsets a1-e1 (inner layer), reserving one outer layer subset (Subset A in the example below). 3) For each of the 5 inner layer subsets, cross validation of forward stepwise logistic regression models was performed in which the maximum number of genes allowed in the final model is 1, 2, 3, 4, 5, 6, 7, 8, 9, and 10 genes. Cross validation is performed as follows (using the example below):

a. Training set (a1-d1) Test set (e1)

b. Training set (b1-e1) Test set (a1)

c. Training set (c1-a1) Test set (b1)

d. Training set (d1-b1) Test set (c1)

e. Training set (e1-c1) Test set (d1)

4) This resulted in 5 models with 1 gene, 5 models with 2 genes, etc.

5) From each of these models, the following model performance measure of the Test Set was obtained: AUC (Area under the receiver operating characteristic curve—used to evaluate the combined sensitivity and specificity of the model). 6) The median AUC of the Test Sets across the 5 models was obtained for each of the 1, 2, 3, 4, 5, 6, 7, 8, 9, and 10 models. 7) Sorting in ascending order by the number of genes in the model, the first median AUC maxima was picked to identify the optimal number of genes in the model. 8) Using the optimal number of genes identified through the inner layer, forward stepwise logistic regression was performed on the entire inner layer (a1-e1), fixing the number of genes in the final model to the optimal number of genes identified in step 7. 8a) Using the model estimated from the full inner layer, the model was tested on the reserved outer layer (Subset A in the example below). 8b) The following model performance measures were obtained: AUC, sensitivity, and specificity.

Partition #1

Outer Layer (n = 144 Samples)

| A = 28 | B = 29 | C = 29 | D = 29 | E = 29 |

Inner Layer (n = 116 Samples)

| a1 = 24 | b1 = 23 | c1 = 23 | d1 = 23 | e1 = 23 |

9) This process was repeated 4 more times, reserving outer layer Subsets B, C, D, and E in a similar manner. This 2-layer process resulted in 5 models tested on the outer layer with the initial random partition of the data. Each of the 5 models had a different number of genes and different genes with different coefficients.

The entire approach described in steps 1-9 was repeated fifty times with different random partitions of the outer layer data. This resulted in 250 models. The models derived for each of four analyses are shown in the Table 3 (all patients, ORR), Table 4 (all patients, DC), Table 7 (KRAS-Negative patients, ORR) and Table 9 (KRAS-Negative patients, DC).

Example 2

Identification of Gene Markers of Response to an EGFR Inhibitor In Colon Cancer Patients (ORR Endpoint)

Tables 1A and 1B show genes whose normalized expression is correlated (univariate analysis) positively (Table 1A) or negatively (Table 1B) with Overall Response Rate (ORR) in colon cancer patients treated with cetuximab. FIGS. 3A-3D show probability curves that correspond to the data reported in Table 1A; FIGS. 4A-4F show probability curves that correspond to the data reported in Table 1B.

TABLE 1A

| Gene | N | Likelihood Ratio Chi-sq | Likelihood Ratio p-value | Odds Ratio | Wald 95% CI for OR |
|---|---|---|---|---|---|
| SATB2 | 226 | 18.9637 | <0.0001 | 2.9534 | (1.68, 5.20) |
| PTP4A3 | 225 | 26.0286 | <0.0001 | 2.8221 | (1.84, 4.33) |
| QPRT | 226 | 23.0849 | <0.0001 | 2.7047 | (1.62, 4.52) |
| VAV3 | 226 | 20.3475 | <0.0001 | 2.4744 | (1.58, 3.88) |
| CEACAM6 | 226 | 9.733 | 0.0018 | 2.3749 | (1.33, 4.26) |
| EREG | 226 | 24.8105 | <0.0001 | 2.0472 | (1.48, 2.82) |
| ErbB3 | 226 | 4.5578 | 0.0328 | 2.0275 | (1.04, 3.97) |
| EGFR | 226 | 7.5416 | 0.006 | 2.015 | (1.20, 3.38) |
| AREG | 226 | 20.3261 | <0.0001 | 2.0087 | (1.44, 2.81) |
| BRCA1 | 226 | 5.1436 | 0.0233 | 1.955 | (1.08, 3.55) |
| TITF1 | 226 | 9.245 | 0.0024 | 1.8605 | (1.25, 2.76) |
| SORBS1 | 226 | 7.7284 | 0.0054 | 1.7668 | (1.17, 2.66) |
| CHN2 | 226 | 7.7635 | 0.0053 | 1.5934 | (1.15, 2.21) |
| C13orf18 | 226 | 7.664 | 0.0056 | 1.5249 | (1.11, 2.10) |
| CKMT2 | 226 | 7.8393 | 0.0051 | 1.4147 | (1.11, 1.80) |
| SLC26A3 | 226 | 7.4754 | 0.0063 | 1.304 | (1.07, 1.58) |

TABLE 1B

| Gene | N | Likelihood Ratio Chi-sq | Likelihood Ratio p-value | Odds Ratio | Wald 95% CI for OR |
|---|---|---|---|---|---|
| VDAC2 | 226 | 8.5381 | 0.0035 | 0.2000 | (0.06, 0.62) |
| SERPINB1 | 226 | 19.1870 | <0.0001 | 0.2276 | (0.11, 0.48) |

TABLE 1B-continued

| Gene | N | Likelihood Ratio Chi-sq | Likelihood Ratio p-value | Odds Ratio | Wald 95% CI for OR |
|---|---|---|---|---|---|
| PHLDA1 | 226 | 29.6796 | <0.0001 | 0.2467 | (0.14, 0.44) |
| K-ras | 226 | 10.8371 | 0.0010 | 0.2577 | (0.11, 0.60) |
| ANXA2P2 | 226 | 13.9775 | 0.0002 | 0.2578 | (0.12, 0.55) |
| GPC3 | 226 | 4.7438 | 0.0294 | 0.2591 | (0.06, 1.17) |
| DUSP6 | 226 | 12.2004 | 0.0005 | 0.3275 | (0.17, 0.63) |
| KRT17 | 226 | 18.7538 | <0.0001 | 0.4037 | (0.24, 0.67) |
| DUSP4 | 226 | 18.6992 | <0.0001 | 0.4284 | (0.28, 0.66) |
| EPHA2 | 226 | 10.3795 | 0.0013 | 0.4435 | (0.26, 0.75) |
| DR5 | 226 | 6.1028 | 0.0135 | 0.4919 | (0.28, 0.88) |
| PLAUR | 226 | 4.7090 | 0.0300 | 0.5990 | (0.38, 0.96) |
| LAMA3 | 226 | 6.8684 | 0.0088 | 0.6103 | (0.42, 0.89) |
| LAMC2 | 226 | 5.3802 | 0.0204 | 0.6338 | (0.43, 0.94) |
| ANXA1 | 226 | 3.8575 | 0.0495 | 0.6395 | (0.41, 1.01) |
| CA9 | 226 | 8.3394 | 0.0039 | 0.6671 | (0.49, 0.90) |
| Maspin | 226 | 6.9632 | 0.0083 | 0.6891 | (0.52, 0.92) |
| GCNT3 | 226 | 4.0035 | 0.0454 | 0.7833 | (0.62, 1.00) |

Example 3

Identification of Gene Markers of Response to an EGFR Inhibitor in Colon Cancer Patients (DC Endpoint)

Tables 2A and 2B show genes whose normalized expression is correlated (univariate analysis) positively (Table 2A) or negatively (Table 2B) with Disease Control in colon cancer patients treated with cetuximab. FIGS. 5A-5E show probability curves that correspond to the data reported in Table 2A; FIGS. 6A-6F shows probability curves that correspond to the data reported in Table 2B.

TABLE 2A

| Gene | N | Likelihood Ratio Chi-sq | Likelihood Ratio p-value | Odds Ratio | Wald 95% CI for OR |
|---|---|---|---|---|---|
| ATP5E | 226 | 6.8380 | 0.0089 | 2.6122 | (1.25, 5.46) |
| TITF1 | 226 | 14.1821 | 0.0002 | 2.6063 | (1.33, 5.11) |
| CLTC | 226 | 3.9206 | 0.0477 | 2.2407 | (1.00, 5.04) |
| BRCA1 | 226 | 13.3432 | 0.0003 | 2.1392 | (1.39, 3.29) |
| AREG | 226 | 38.6000 | <0.0001 | 1.9568 | (1.55, 2.48) |
| PTP4A3 | 225 | 18.2969 | <0.0001 | 1.8994 | (1.39, 2.60) |
| EREG | 226 | 43.3856 | <0.0001 | 1.8979 | (1.54, 2.34) |
| VAV3 | 226 | 25.3219 | <0.0001 | 1.8784 | (1.43, 2.46) |
| SATB2 | 226 | 18.0834 | <0.0001 | 1.8534 | (1.36, 2.53) |
| CEACAM6 | 226 | 10.7223 | 0.0011 | 1.8100 | (1.24, 2.63) |
| EGFR | 226 | 7.9284 | 0.0049 | 1.7682 | (1.16, 2.69) |
| CHN2 | 226 | 9.2413 | 0.0024 | 1.4595 | (1.14, 1.87) |

TABLE 2A-continued

| Gene | N | Likelihood Ratio Chi-sq | Likelihood Ratio p-value | Odds Ratio | Wald 95% CI for OR |
|---|---|---|---|---|---|
| FGFR3 | 226 | 4.8531 | 0.0276 | 1.4321 | (1.03, 1.98) |
| C13orf18 | 226 | 12.3329 | 0.0004 | 1.4219 | (1.16, 1.75) |
| QPRT | 226 | 11.3648 | 0.0007 | 1.4045 | (1.14, 1.73) |
| AMACR1 | 226 | 7.3968 | 0.0065 | 1.3774 | (1.09, 1.75) |
| CKMT2 | 226 | 10.4841 | 0.0012 | 1.3646 | (1.12, 1.66) |
| ID1 | 226 | 6.6866 | 0.0097 | 1.3422 | (1.07, 1.69) |
| SORBS1 | 226 | 4.0375 | 0.0445 | 1.3366 | (1.00, 1.78) |
| SLC26A3 | 226 | 12.3503 | 0.0004 | 1.2744 | (1.11, 1.46) |

TABLE 2B

| Gene | N | Likelihood Ratio Chi-sq | Likelihood Ratio p-value | Odds Ratio | Wald 95% CI for OR |
|---|---|---|---|---|---|
| DUSP6 | 226 | 28.9122 | <0.0001 | 0.2867 | (0.18, 0.47) |
| VDAC2 | 226 | 8.8433 | 0.0029 | 0.3326 | (0.16, 0.70) |
| ANXA2P2 | 226 | 15.7199 | 0.0001 | 0.3762 | (0.23, 0.63) |
| SERPINB1 | 226 | 17.4287 | <0.0001 | 0.4071 | (0.26, 0.64) |
| NT5E | 226 | 25.7449 | <0.0001 | 0.4798 | (0.35, 0.65) |
| GPC3 | 226 | 5.5891 | 0.0181 | 0.4926 | (0.25, 0.96) |
| DUSP4 | 226 | 25.0584 | <0.0001 | 0.5403 | (0.42, 0.70) |
| PHLDA1 | 226 | 14.7168 | 0.0001 | 0.5431 | (0.39, 0.75) |
| K-ras | 226 | 4.7480 | 0.0293 | 0.5510 | (0.32, 0.95) |
| DR5 | 226 | 8.2890 | 0.0040 | 0.5640 | (0.38, 0.84) |
| VIL2 | 226 | 5.4978 | 0.0190 | 0.5898 | (0.38, 0.93) |
| LAMC2 | 226 | 11.8210 | 0.0006 | 0.6184 | (0.46, 0.82) |
| SFN | 226 | 7.5520 | 0.0060 | 0.6232 | (0.44, 0.88) |
| ANXA1 | 226 | 7.5088 | 0.0061 | 0.6433 | (0.46, 0.89) |
| EPHA2 | 226 | 6.0724 | 0.0137 | 0.6641 | (0.48, 0.93) |
| P14ARF | 226 | 7.2707 | 0.0070 | 0.6889 | (0.52, 0.92) |
| CA9 | 226 | 11.8606 | 0.0006 | 0.7375 | (0.62, 0.88) |
| KRT17 | 226 | 8.3190 | 0.0039 | 0.7385 | (0.60, 0.92) |
| p14ARF | 226 | 3.9325 | 0.0474 | 0.7580 | (0.57, 1.00) |
| Maspin | 226 | 7.9126 | 0.0049 | 0.7589 | (0.62, 0.92) |

Example 4

Multigene Models of Response to an EGFR Inhibitor in Colon Cancer Patients (ORR Endpoint)

Table 3 presents a table that shows genes and gene combinations whose expression levels can be combined in multi-gene models that significantly correlate with Overall Response Rate in colon cancer patients treated with cetuximab. Note: "aregereg" is the average of the normalized AREG value and the normalized EREG value. Note: "MutInd" is the K-Ras mutation status indicator variable that is included as an interaction variable with each gene.

TABLE 3

| Genes | # Models | % of Models | Mean AUC | SD AUC | Median AUC |
|---|---|---|---|---|---|
| 1-Gene Models | | | | | |
| PTP4A3 | 18 | 64% | 0.71 | 0.11 | 0.74 |
| PHLDA1 | 6 | 21% | 0.71 | 0.06 | 0.73 |
| Aregereg | 2 | 7% | 0.67 | 0.05 | 0.67 |
| EREG | 2 | 8% | 0.81 | 0.07 | 0.81 |
| Total | 28 | 11% | 0.72 | 0.07 | 0.74 |
| 2-Gene Models | | | | | |
| PHLDA1 PTP4A3 | 64 | 52% | 0.82 | 0.08 | 0.83 |
| PHLDA1 aregereg | 31 | 25% | 0.86 | 0.05 | 0.85 |

TABLE 3-continued (ORR)

| Genes | # Models | % of Models | Mean AUC | SD AUC | Median AUC |
|---|---|---|---|---|---|
| EREG PHLDA1 | 18 | 15% | 0.83 | 0.06 | 0.84 |
| AREG PHLDA1 | 2 | 2% | 0.84 | 0.10 | 0.84 |
| CHN2 PTP4A3 | 2 | 2% | 0.69 | 0.02 | 0.69 |
| PTP4A3 SATB2 | 2 | 2% | 0.66 | 0.03 | 0.66 |
| EPHA2 aregereg | 1 | 1% | 0.76 | — | 0.76 |
| EREG PTP4A3 | 1 | 1% | 0.70 | — | 0.70 |
| PTP4A3 SLC26A3 | 1 | 1% | 0.74 | — | 0.74 |
| Total | 122 | 49% | 0.77 | 0.06 | 0.77 |
| 3-Gene Models | | | | | |
| PHLDA1 PTP4A3 aregereg | 10 | 19% | 0.87 | 0.04 | 0.89 |
| EGFR PHLDA1 PTP4A3 | 5 | 9% | 0.83 | 0.06 | 0.85 |
| PHLDA1 PTP4A3 SATB2 | 5 | 9% | 0.76 | 0.03 | 0.77 |
| AREG PHLDA1 PTP4A3 | 3 | 6% | 0.91 | 0.04 | 0.89 |
| EGFR PHLDA1 aregereg | 3 | 6% | 0.81 | 0.11 | 0.87 |
| EREG KRT17 PHLDA1 | 3 | 6% | 0.81 | 0.08 | 0.79 |
| EREG PHLDA1 PTP4A3 | 3 | 6% | 0.86 | 0.04 | 0.88 |
| EREG PHLDA1 SATB2 | 3 | 6% | 0.79 | 0.09 | 0.82 |
| EREG PHLDA1 SORBS1 | 3 | 6% | 0.82 | 0.02 | 0.81 |
| KRT17 PHLDA1 aregereg | 3 | 6% | 0.82 | 0.05 | 0.79 |
| MutInd_PTP4A3 PHLDA1 PTP4A3 | 2 | 4% | 0.78 | 0.02 | 0.78 |
| PHLDA1 SATB2 aregereg | 2 | 4% | 0.75 | 0.00 | 0.75 |
| AREG CEACAM6 PHLDA1 | 1 | 2% | 0.74 | — | 0.74 |
| AREG EGFR PHLDA1 | 1 | 2% | 0.79 | — | 0.79 |
| DUSP6 PTP4A3 SORBS1 | 1 | 2% | 0.52 | — | 0.52 |
| EGFR EPHA2 PTP4A3 | 1 | 2% | 0.76 | — | 0.76 |
| EGFR EREG PHLDA1 | 1 | 2% | 0.86 | — | 0.86 |
| EREG KRT17 PTP4A3 | 1 | 2% | 0.81 | — | 0.81 |
| MutInd_DUSP6 MutInd_EGFR PTP4A3 | 1 | 2% | 0.79 | — | 0.79 |
| PHLDA1 PTP4A3 SORBS1 | 1 | 2% | 0.82 | — | 0.82 |
| Total | 53 | 21% | 0.80 | 0.05 | 0.80 |
| 4-Gene Models | | | | | |
| AREG EGFR PHLDA1 PTP4A3 | 3 | 13% | 0.87 | 0.02 | 0.88 |
| AREG MutInd_PTP4A3 PHLDA1 PTP4A3 | 3 | 13% | 0.74 | 0.01 | 0.74 |
| PHLDA1 PTP4A3 SATB2 aregereg | 3 | 13% | 0.81 | 0.12 | 0.84 |
| PHLDA1 PTP4A3 SORBS1 aregereg | 3 | 13% | 0.79 | 0.07 | 0.79 |
| KRT17 PHLDA1 SORBS1 aregereg | 2 | 8% | 0.82 | 0.05 | 0.82 |
| CEACAM6 PHLDA1 PTP4A3 aregereg | 1 | 4% | 0.74 | — | 0.74 |
| EGFR EPHA2 PHLDA1 aregereg | 1 | 4% | 0.73 | — | 0.73 |
| EGFR EREG KRT17 PHLDA1 | 1 | 4% | 0.76 | — | 0.76 |
| EGFR EREG PHLDA1 PTP4A3 | 1 | 4% | 0.82 | — | 0.82 |
| EGFR KRT17 PHLDA1 PTP4A3 | 1 | 4% | 0.73 | — | 0.73 |
| EPHA2 PHLDA1 PTP4A3 aregereg | 1 | 4% | 0.69 | — | 0.69 |
| EREG KRT17 PHLDA1 SORBS1 | 1 | 4% | 0.79 | — | 0.79 |
| EREG PHLDA1 PLAUR SATB2 | 1 | 4% | 0.74 | — | 0.74 |
| KRT17 MutInd_PTP4A3 PHLDA1 aregereg | 1 | 4% | 0.75 | — | 0.75 |
| KRT17 PHLDA1 PTP4A3 SATB2 | 1 | 4% | 0.83 | — | 0.83 |
| Total | 24 | 10% | 0.77 | 0.06 | 0.78 |
| 5-Gene Models | | | | | |
| CEACAM6 KRT17 PHLDA1 SORBS1 aregereg | 2 | 13% | 0.84 | 0.10 | 0.84 |
| PHLDA1 PTP4A3 SATB2 SORBS1 aregereg | 2 | 13% | 0.86 | 0.04 | 0.86 |
| AREG EGFR EPHA2 PHLDA1 PTP4A3 | 1 | 7% | 0.89 | — | 0.89 |
| CEACAM6 EGFR KRT17 PHLDA1 aregereg | 1 | 7% | 0.80 | — | 0.80 |
| CEACAM6 KRT17 PHLDA1 PTP4A3 SORBS1 | 1 | 7% | 0.81 | — | 0.81 |
| EGFR EPHA2 EREG PHLDA1 SATB2 | 1 | 7% | 0.73 | — | 0.73 |
| EGFR EREG KRT17 PHLDA1 SATB2 | 1 | 7% | 0.81 | — | 0.81 |
| EGFR EREG KRT17 PHLDA1 SORBS1 | 1 | 7% | 0.77 | — | 0.77 |
| EGFR KRT17 PHLDA1 PTP4A3 aregereg | 1 | 7% | 0.79 | — | 0.79 |
| EGFR KRT17 PHLDA1 PTP4A3 SATB2 | 1 | 7% | 0.71 | — | 0.71 |
| EGFR PHLDA1 PTP4A3 SORBS1 aregereg | 1 | 7% | 0.83 | — | 0.83 |
| EREG PHLDA1 QPRT SATB2 SORBS1 | 1 | 7% | 0.57 | — | 0.57 |
| KRT17 PHLDA1 SORBS1 aregereg mutant_ind | 1 | 7% | 0.75 | — | 0.75 |
| Total | 15 | 6% | 0.78 | 0.07 | 0.78 |

TABLE 3-continued (ORR)

| Genes | # Models | % of Models | Mean AUC | SD AUC | Median AUC |
|---|---|---|---|---|---|
| 6-Gene Models | | | | | |
| AREG EGFR EPHA2 LAMA3 PHLDA1 PTP4A3 | 1 | 20% | 0.88 | — | 0.88 |
| AREG EGFR KRT17 PHLDA1 PTP4A3 SORBS1 | 1 | 20% | 0.85 | — | 0.85 |
| EGFR EPHA2 EREG PHLDA1 PLAUR SATB2 | 1 | 20% | 0.72 | — | 0.72 |
| KRT17 MutInd_DUSP6 MutInd_EGFR PTP4A3 SORBS1 aregereg | 1 | 20% | 0.92 | — | 0.92 |
| KRT17 MutInd_PTP4A3 PHLDA1 PTP4A3 SORBS1 aregereg | 1 | 20% | 0.77 | — | 0.77 |
| Total | 5 | 2% | 0.83 | | 0.83 |

Example 5

Multigene Models of Response to an EGFR Inhibitor in Colon Cancer Patients (DC Endpoint)

Table 4 presents a table that shows genes and gene combinations whose expression levels can be combined in multigene models that significantly correlate with Disease Control in colon cancer patients treated with cetuximab. Note: "aregereg" is the average of the normalized AREG value and the normalized EREG value. Note: "MutInd" is the K-Ras mutation status indicator variable that is included as an interaction variable with each gene.

TABLE 4

(DCS)

| Genes | # Models | % of Models | Mean AUC | SD AUC | Median AUC |
|---|---|---|---|---|---|
| 1-Gene Models | | | | | |
| aregereg | 22 | 65% | 0.70 | 0.06 | 0.71 |
| EREG | 12 | 35% | 0.72 | 0.05 | 0.72 |
| Total | 34 | 14% | 0.71 | 0.05 | 0.71 |
| 2-Gene Models | | | | | |
| MutInd_EREG aregereg | 73 | 61% | 0.78 | 0.07 | 0.80 |
| EREG MutInd_EREG | 28 | 24% | 0.78 | 0.06 | 0.80 |
| DUSP6 aregereg | 4 | 3% | 0.73 | 0.03 | 0.73 |
| DUSP6 EREGjh | 3 | 3% | 0.75 | 0.08 | 0.71 |
| MutInd_EPHA2 aregereg | 3 | 3% | 0.78 | 0.05 | 0.75 |
| EREG MutInd_EPHA2 | 2 | 2% | 0.76 | 0.07 | 0.76 |
| EPHA2 aregereg | 1 | 1% | 0.84 | — | 0.84 |
| EREG MutInd_EGFR | 1 | 1% | 0.73 | — | 0.73 |
| EREG MutInd_SLC26A3 | 1 | 1% | 0.73 | — | 0.73 |
| MutInd_EGFR aregereg | 1 | 1% | 0.91 | — | 0.91 |
| MutInd_SFN aregereg | 1 | 1% | 0.79 | — | 0.79 |
| MutInd_SLC26A3 aregereg | 1 | 1% | 0.80 | — | 0.80 |
| Total | 119 | 48% | 0.78 | 0.06 | 0.78 |
| 3-Gene Models | | | | | |
| DUSP6 MutInd_EREG aregereg | 27 | 42% | 0.79 | 0.06 | 0.80 |
| MutInd_EREG VIL2 aregereg | 7 | 11% | 0.80 | 0.02 | 0.81 |
| DUSP6 EREG MutInd_EREG | 6 | 9% | 0.81 | 0.05 | 0.78 |
| EPHA2 MutInd_EREG aregereg | 5 | 8% | 0.79 | 0.09 | 0.77 |
| EREG MutInd_EREG MutInd_ID1 | 4 | 6% | 0.80 | 0.05 | 0.81 |
| EPHA2 EREG MutInd_EREG | 2 | 3% | 0.73 | 0.01 | 0.73 |
| DR5 MutInd_EREG aregereg | 1 | 2% | 0.71 | — | 0.71 |
| DUSP4 MutInd_EREG aregereg | 1 | 2% | 0.83 | — | 0.83 |
| DUSP6 MutInd_SORBS1 aregereg | 1 | 2% | 0.82 | — | 0.82 |
| EREG MutInd_AMACR1 MutInd_EREG | 1 | 2% | 0.71 | — | 0.71 |
| EREG MutInd_BRCA1 MutInd_EREG | 1 | 2% | 0.74 | — | 0.74 |
| EREG MutInd_EREG MutInd_GPC3 | 1 | 2% | 0.63 | — | 0.63 |
| EREG MutInd_EREG MutInd_PHLDA1 | 1 | 2% | 0.71 | — | 0.71 |
| EREG MutInd_EREG MutInd_SERPINB1 | 1 | 2% | 0.77 | — | 0.77 |
| EREG MutInd_EREG SFN | 1 | 2% | 0.78 | — | 0.78 |
| EREG MutInd_EREG VIL2 | 1 | 2% | 0.76 | — | 0.76 |
| MutInd_AMACR1 MutInd_EREG aregereg | 1 | 2% | 0.69 | — | 0.69 |

TABLE 4-continued (DCS)

| Genes | # Models | % of Models | Mean AUC | SD AUC | Median AUC |
|---|---|---|---|---|---|
| MutInd_EREG MutInd_ID1 aregereg | 1 | 2% | 0.74 | — | 0.74 |
| MutInd_EREG NT5E aregereg | 1 | 2% | 0.70 | — | 0.70 |
| Total | 64 | 26% | 0.75 | 0.05 | 0.75 |
| 4-Gene Models | | | | | |
| DUSP6 MutInd_EREG MutInd_ID1 | 5 | 18% | 0.78 | 0.09 | 0.79 |
| MutInd_EREG MutInd_ID1 VIL2 aregereg | 3 | 11% | 0.82 | 0.02 | 0.82 |
| DUSP6 MutInd_AMACR1 MutInd_EREG | 2 | 7% | 0.87 | 0.04 | 0.87 |
| DUSP6 MutInd_EREG MutInd_FGFR3 | 2 | 7% | 0.76 | 0.01 | 0.76 |
| DUSP6 MutInd_EREG MutInd_SERPINB1 | 2 | 7% | 0.76 | 0.03 | 0.76 |
| MutInd_EREG MutInd_SERPINB1 VIL2 | 2 | 7% | 0.84 | 0.07 | 0.84 |
| CA9 DUSP6 MutInd_EREG aregereg | 1 | 4% | 0.86 | — | 0.86 |
| DUSP6 EPHA2 NT5E aregereg | 1 | 4% | 0.69 | — | 0.69 |
| DUSP6 EREG ID1 MutInd_EREG | 1 | 4% | 0.83 | — | 0.83 |
| DUSP6 EREG MutInd_AMACR1 | 1 | 4% | 0.86 | — | 0.86 |
| DUSP6 EREG MutInd_EREG | 1 | 4% | 0.82 | — | 0.82 |
| DUSP6 EREG MutInd_EREG | 1 | 4% | 0.83 | — | 0.83 |
| DUSP6 EREG MutInd_EREG | 1 | 4% | 0.76 | — | 0.76 |
| DUSP6 MutInd_EREG MutInd_LAMC2 | 1 | 4% | 0.70 | — | 0.70 |
| DUSP6 MutInd_EREG MutInd_Maspin | 1 | 4% | 0.69 | — | 0.69 |
| DUSP6 MutInd_EREG VIL2 aregereg | 1 | 4% | 0.78 | — | 0.78 |
| EPHA2 MutInd_EREG MutInd_GPC3 | 1 | 4% | 0.72 | — | 0.72 |
| EPHA2 MutInd_EREG MutInd_ID1 | 1 | 4% | 0.74 | — | 0.74 |
| Total | 28 | 11% | 0.78 | 0.04 | 0.78 |
| 5-Gene Models | | | | | |
| AMACR1 DUSP6 MutInd_EREG | 1 | 33% | 0.89 | — | 0.89 |
| CA9 DUSP6 MutInd_EREG | 1 | 33% | 0.82 | — | 0.82 |
| DUSP6 MutInd_EGFR MutInd_EREG | 1 | 33% | 0.79 | — | 0.79 |
| Total | 3 | 1% | 0.83 | — | 0.83 |
| 6-Gene Models | | | | | |
| AMACR1 DUSP6 EREG MutInd_EREG | 1 | 50% | 0.67 | — | 0.67 |
| DUSP6 EREG MutInd_EREG | 1 | 50% | 0.66 | — | 0.66 |
| Total | 2 | 1% | 0.66 | | 0.66 |

Example 6

Determination of KRAS Mutation Status

We estimated a probability of each K-Ras SNP variant for each sample using a logistic model. The model was developed using samples from an external training dataset in which KRAS mutation status of each sample was known. The model was then applied to the colon cetuximab dataset. When the predicted probability of a mutation was greater than 0.5 the sample was classified as positive for the particular KRAS mutation variant. Overall, KRAS mutations were observed in 82 of the 226 cases in this study (36.3%).

Table 5 presents a table that depicts activating KRAS mutations. Those tumors that tested positive for one or more of these mutations were classified KRAS-positive and all other tumors were classified KRAS-negative.

TABLE 5

Tested Activating Mutations in KRAS

| Name | Exon | Position on NM_033360 | KRAS Codon | WT codon | Event | Mutant codon |
|---|---|---|---|---|---|---|
| snp1 | 2 | 216 | 12 | GGT | G->T | GTT |
| snp2 | 2 | 216 | 12 | GGT | G->A | GAT |
| snp3 | 2 | 219 | 13 | GGC | G->A | GAC |
| snp4 | 2 | 215 | 12 | GGT | G->A | AGT |
| snp5 | 2 | 215 | 12 | GGT | G->T | TGT |
| snp6 | 2 | 215 | 12 | GGT | G->C | CGT |
| snp7 | 2 | 216 | 12 | GGT | G->C | GCT |

Example 7

Identification of Gene Markers of Response to an EGFR Inhibitor in KRAS-Negative Colon Cancer Patients (ORR Endpoint)

Figure 7A:
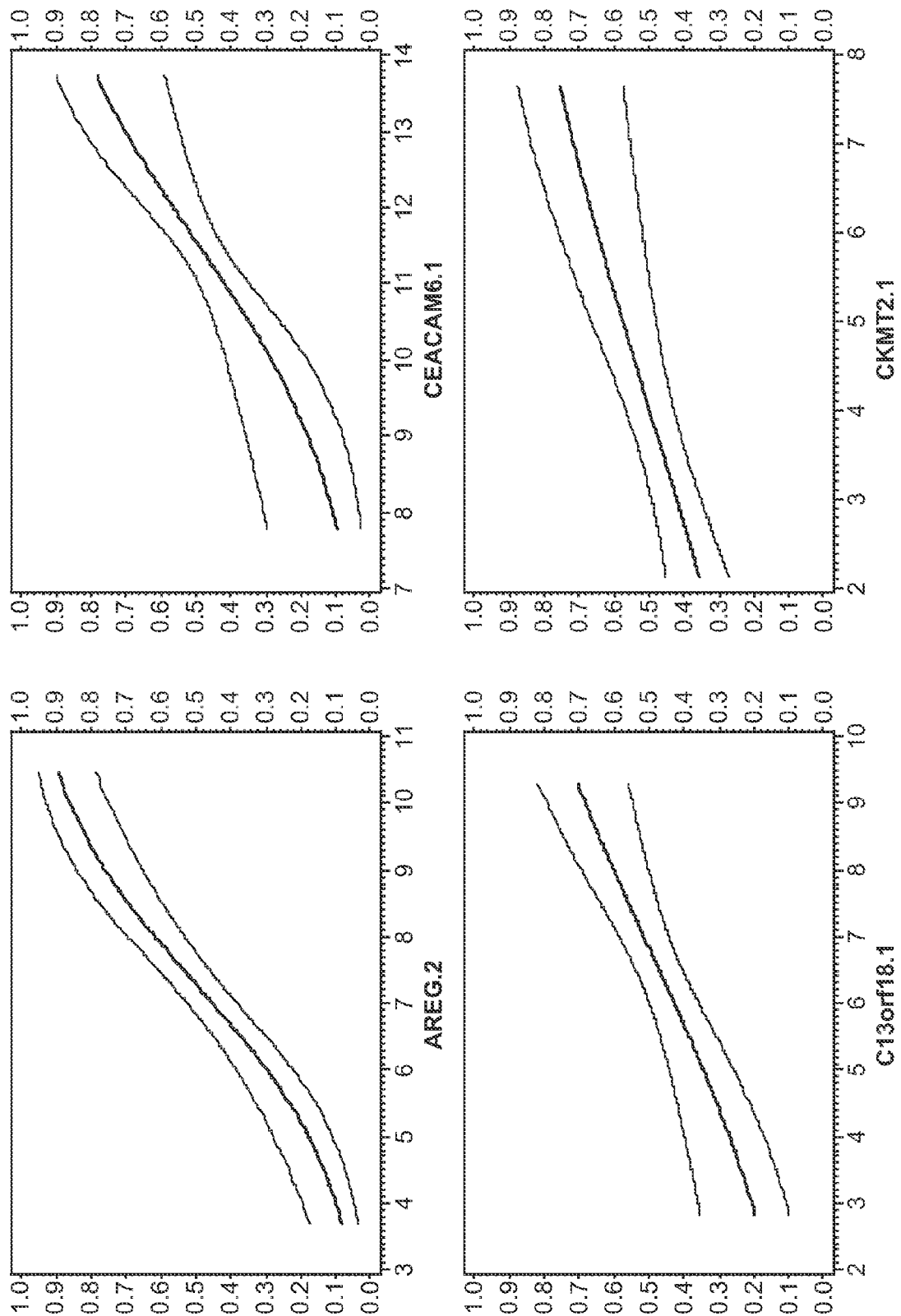
Figure 7C:
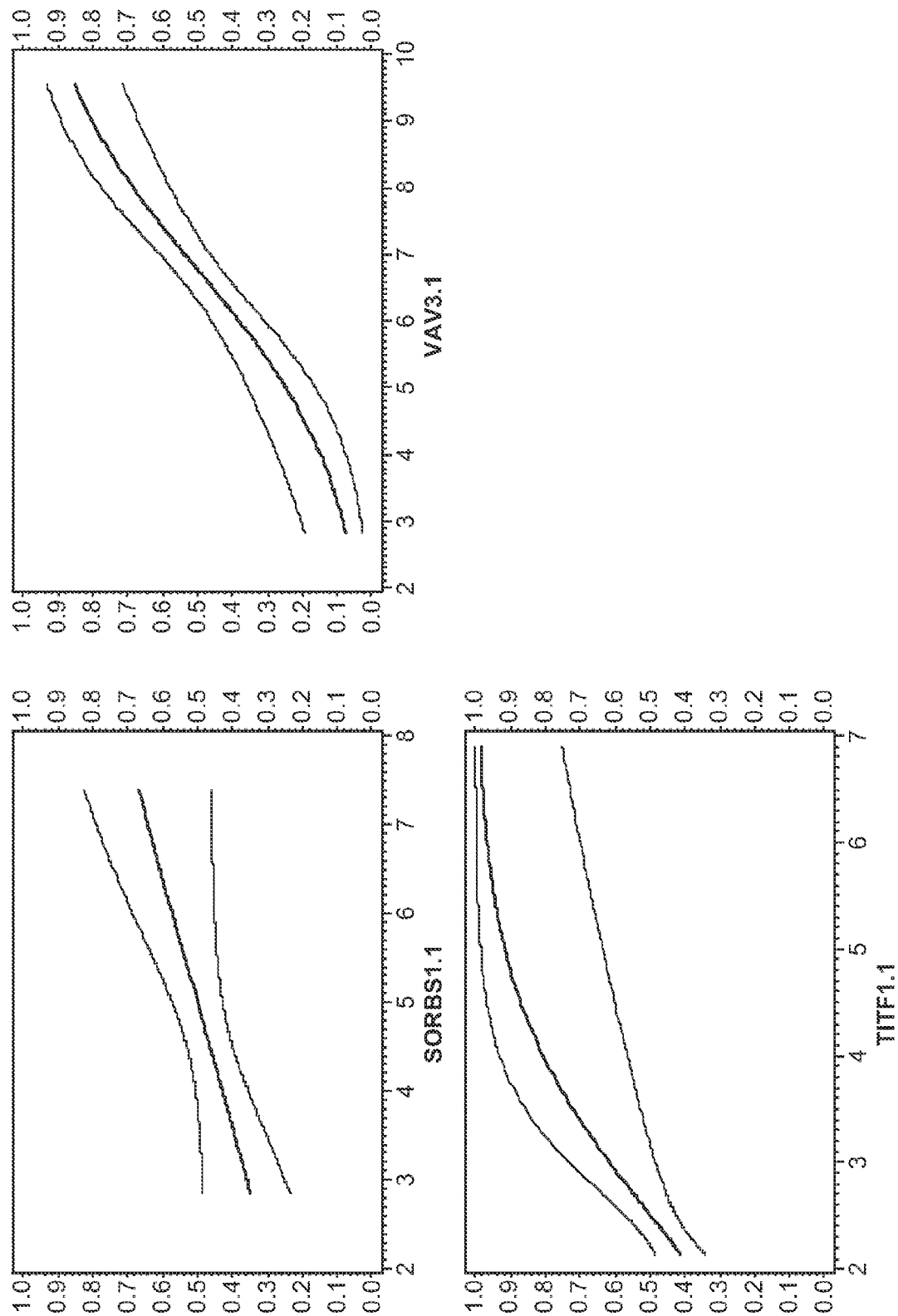
Figure 8A:
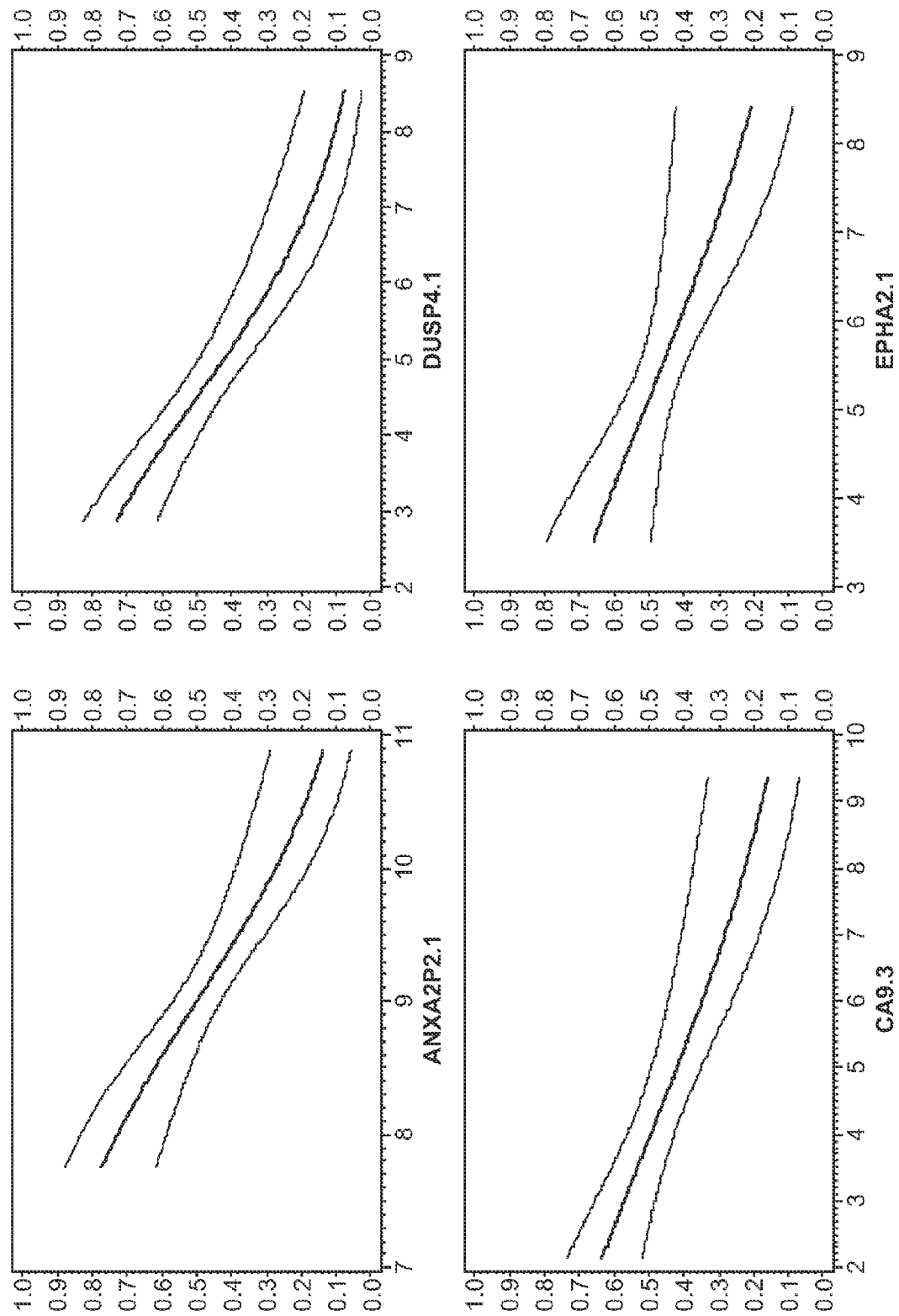
FIGS. 8A-8C show probability curves that correspond to the data reported in Table 6B for analysis of ORR in K-ras negative patients; Odds Ratio<1.
Figure 8B:
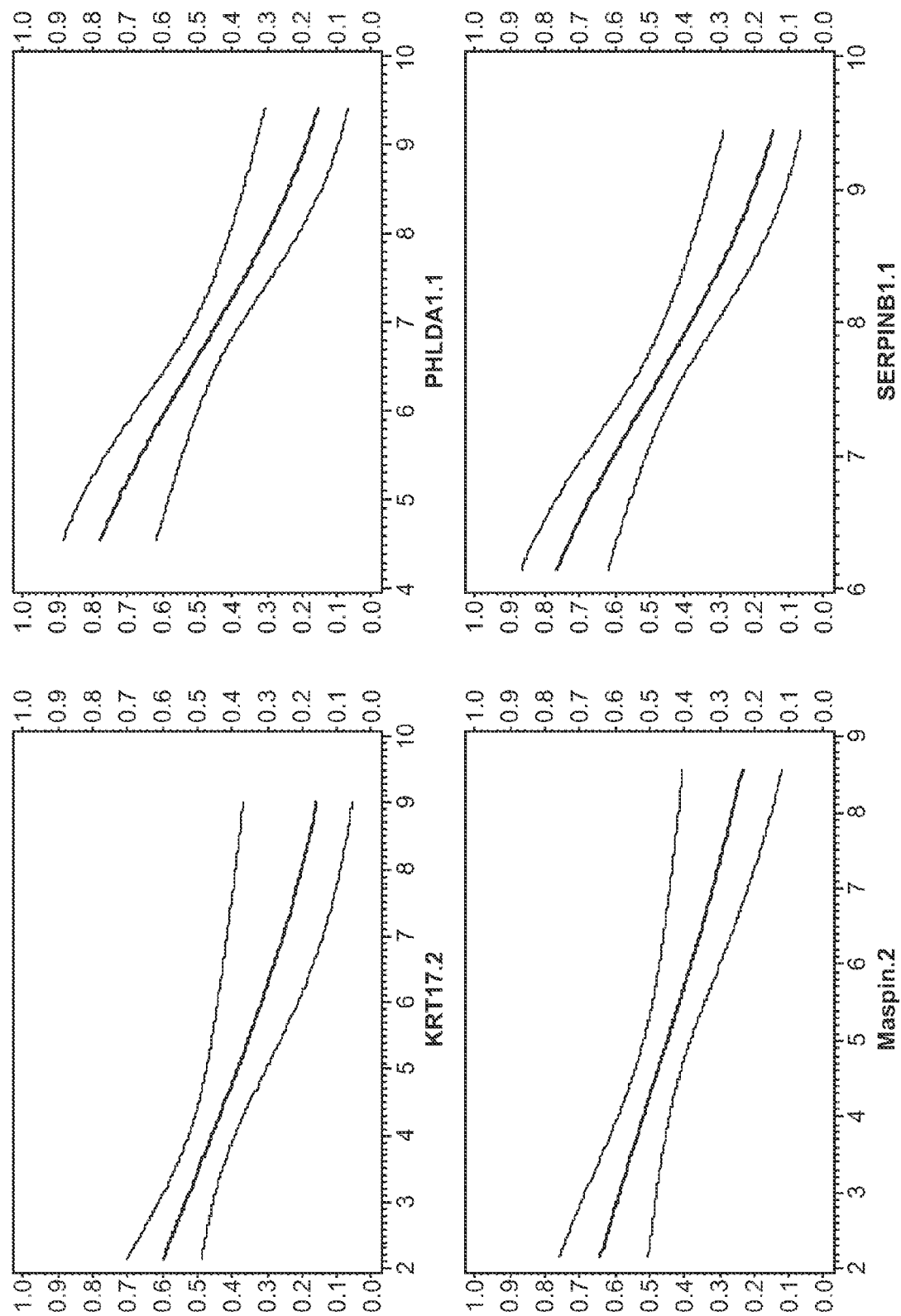
Figure 8C:
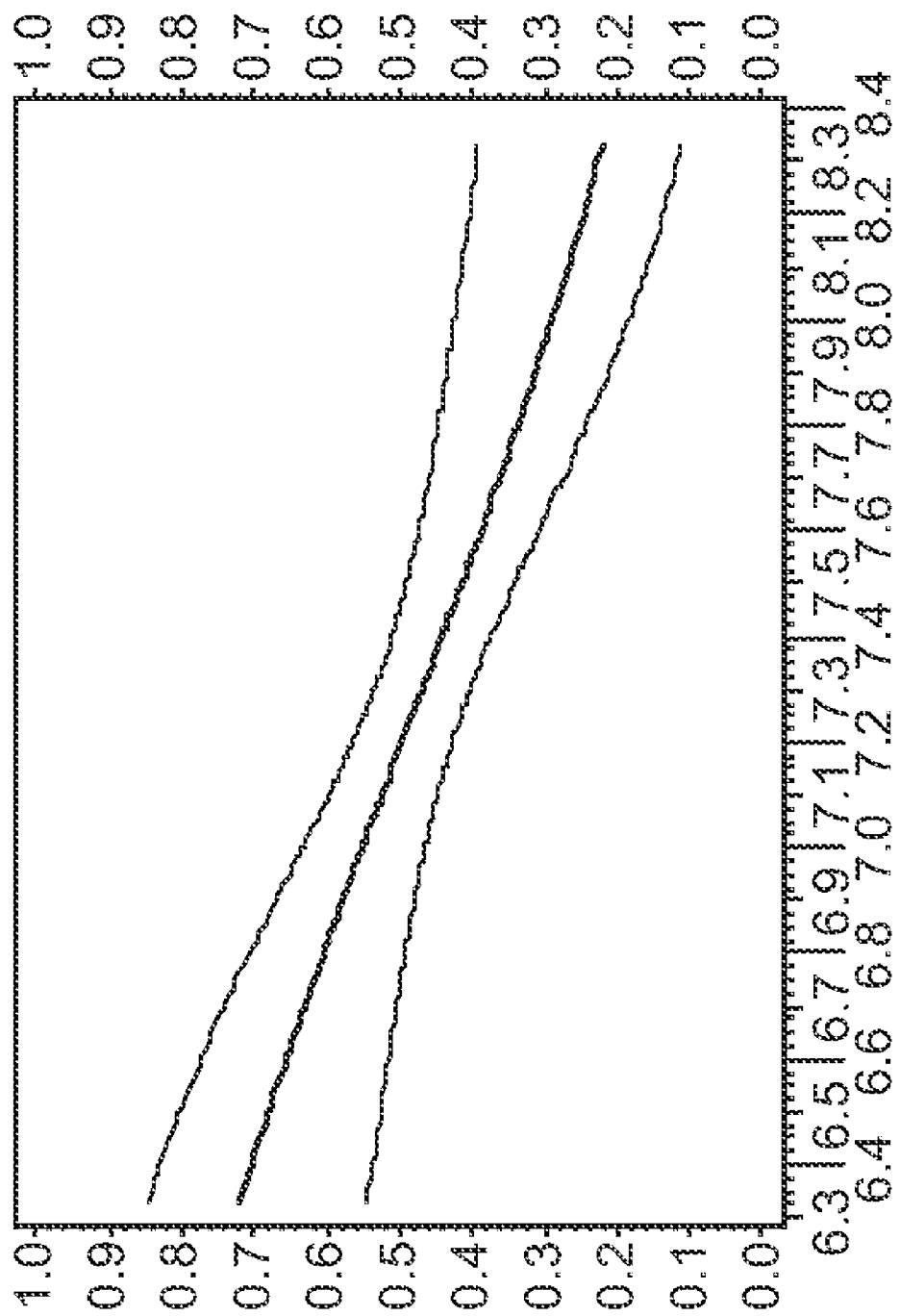
Figure 9A:
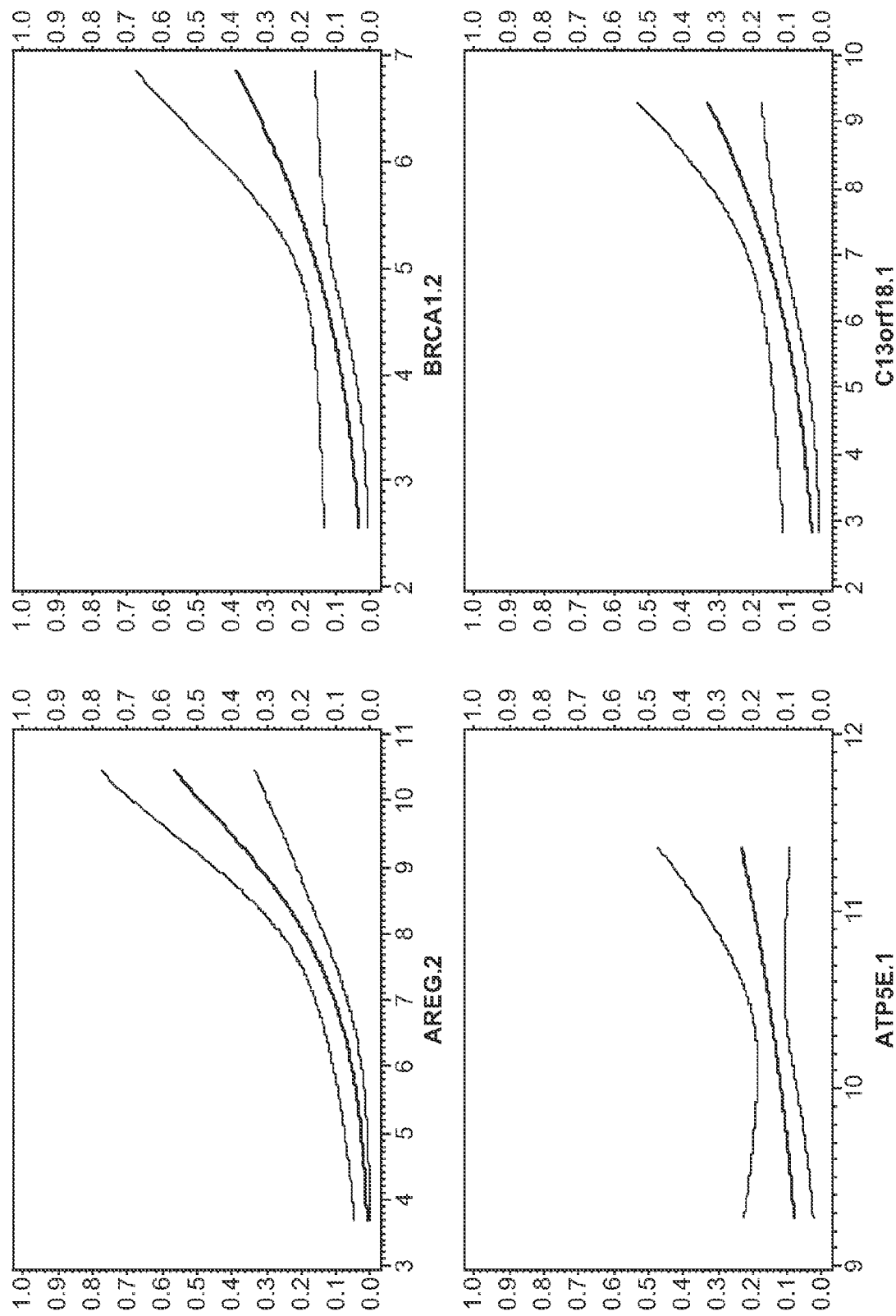
FIGS. 9A-9E show probability curves that correspond to the data reported in Table 7A for analysis of DC in K-ras negative patients; Odds Ratio>1.
Figure 9B:
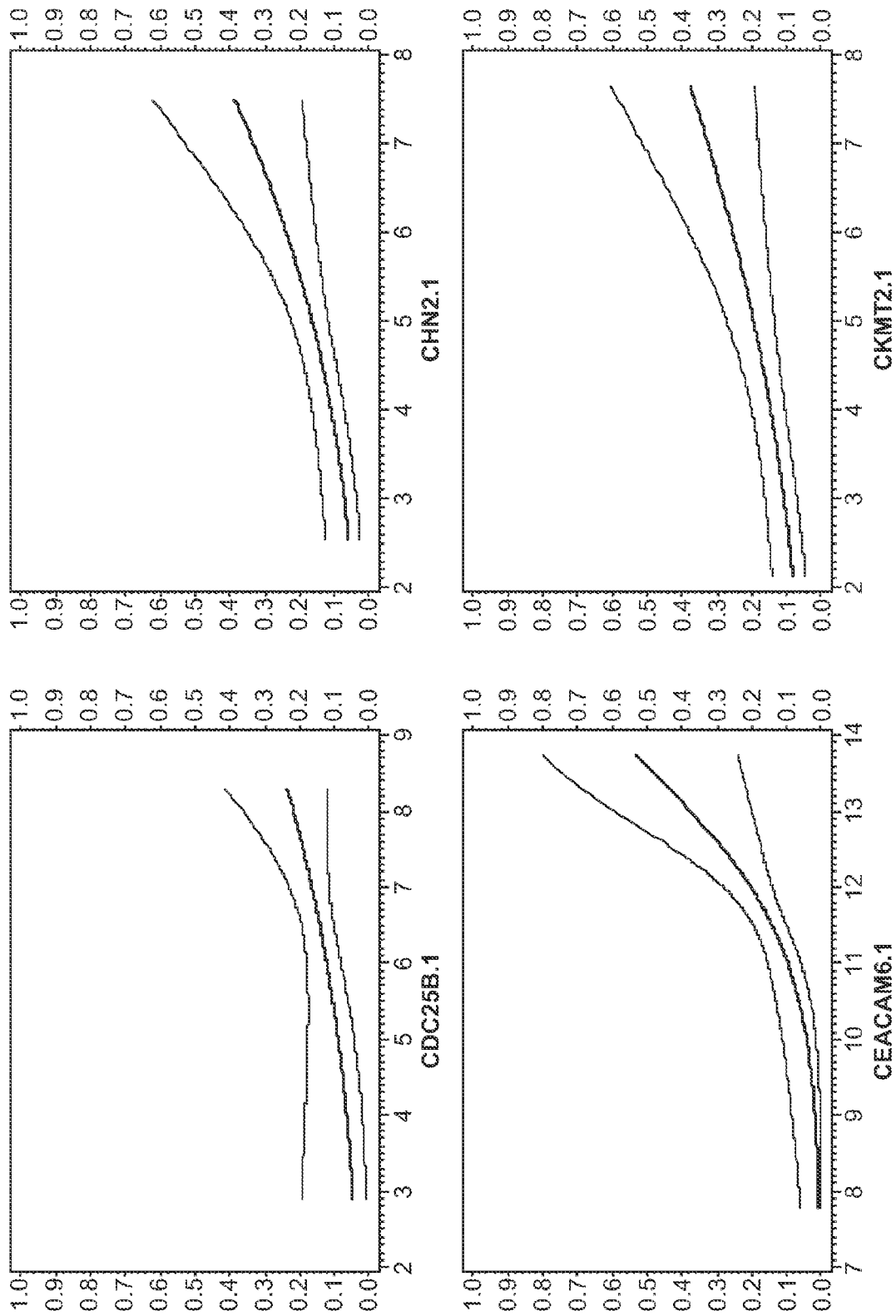
Figure 9C:
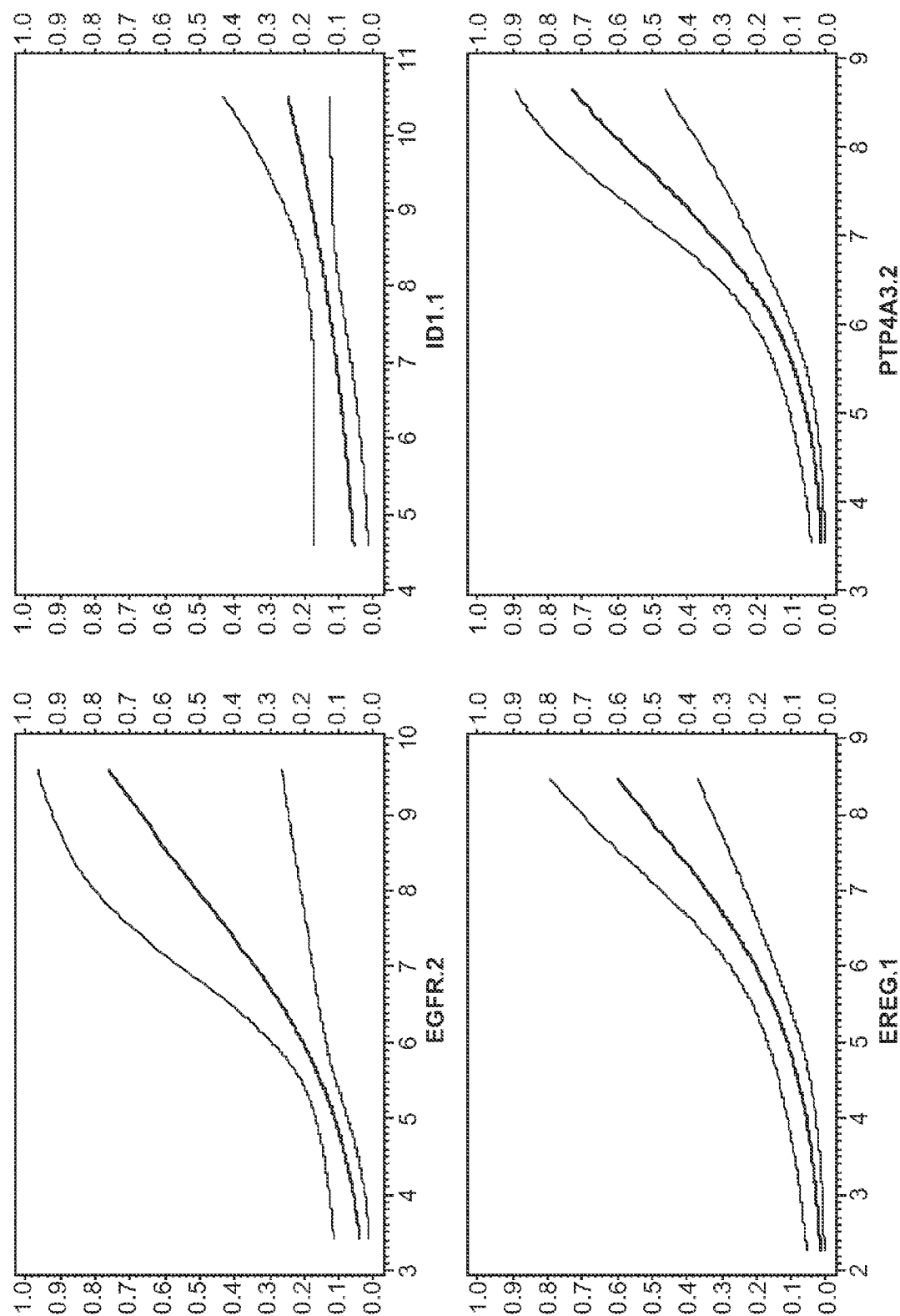
Figure 9D:
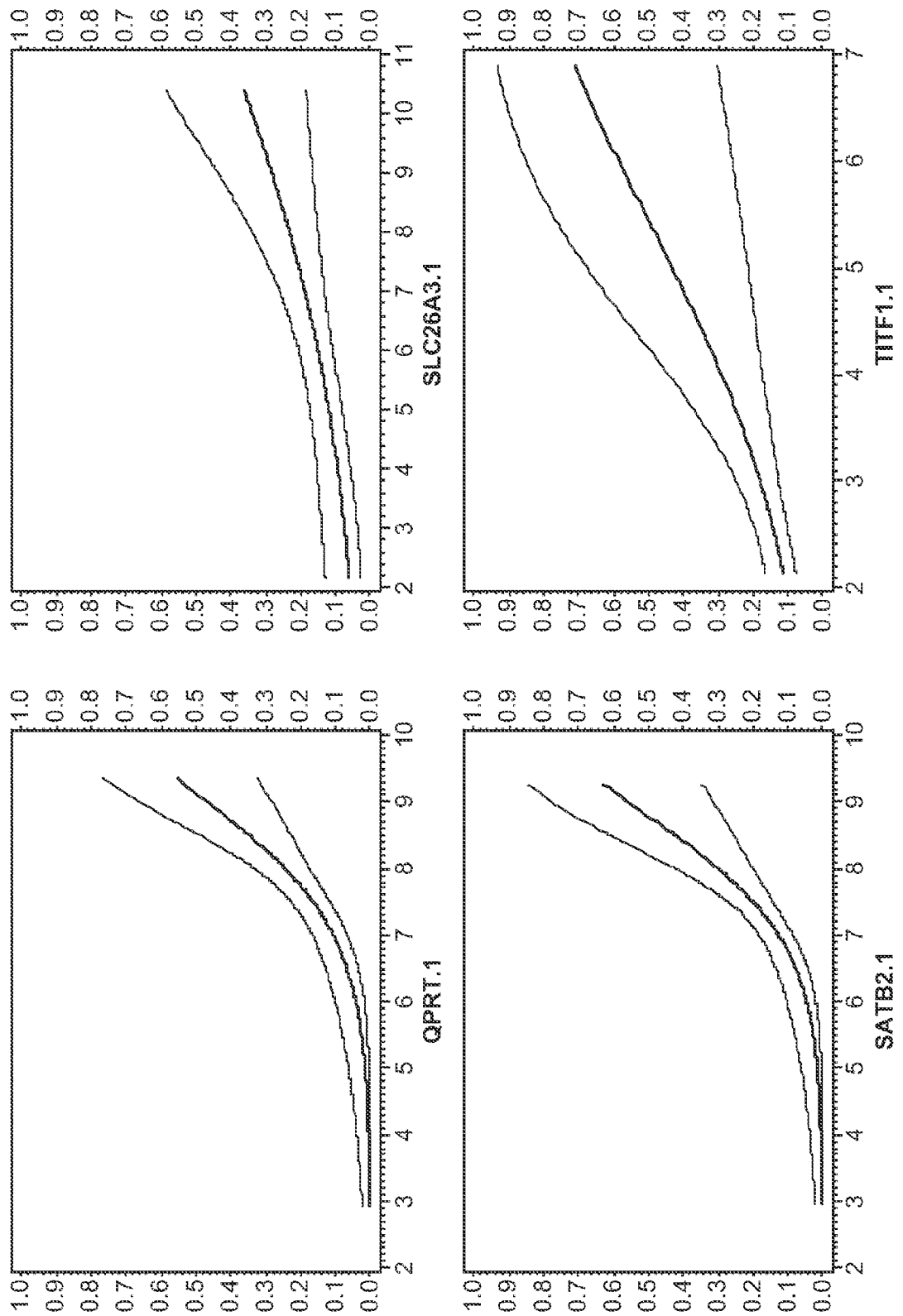
Figure 9E:
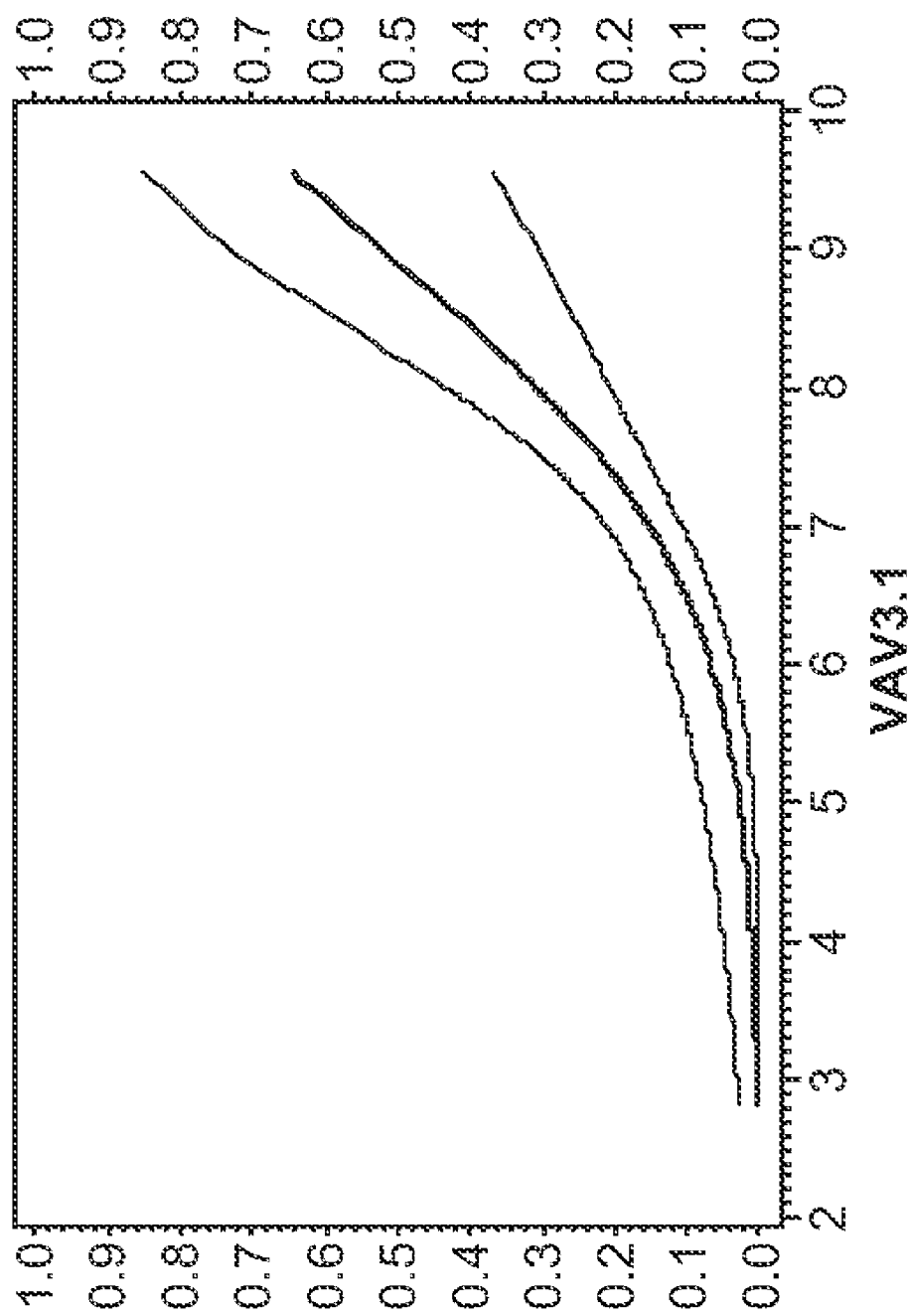
Figure 10A:
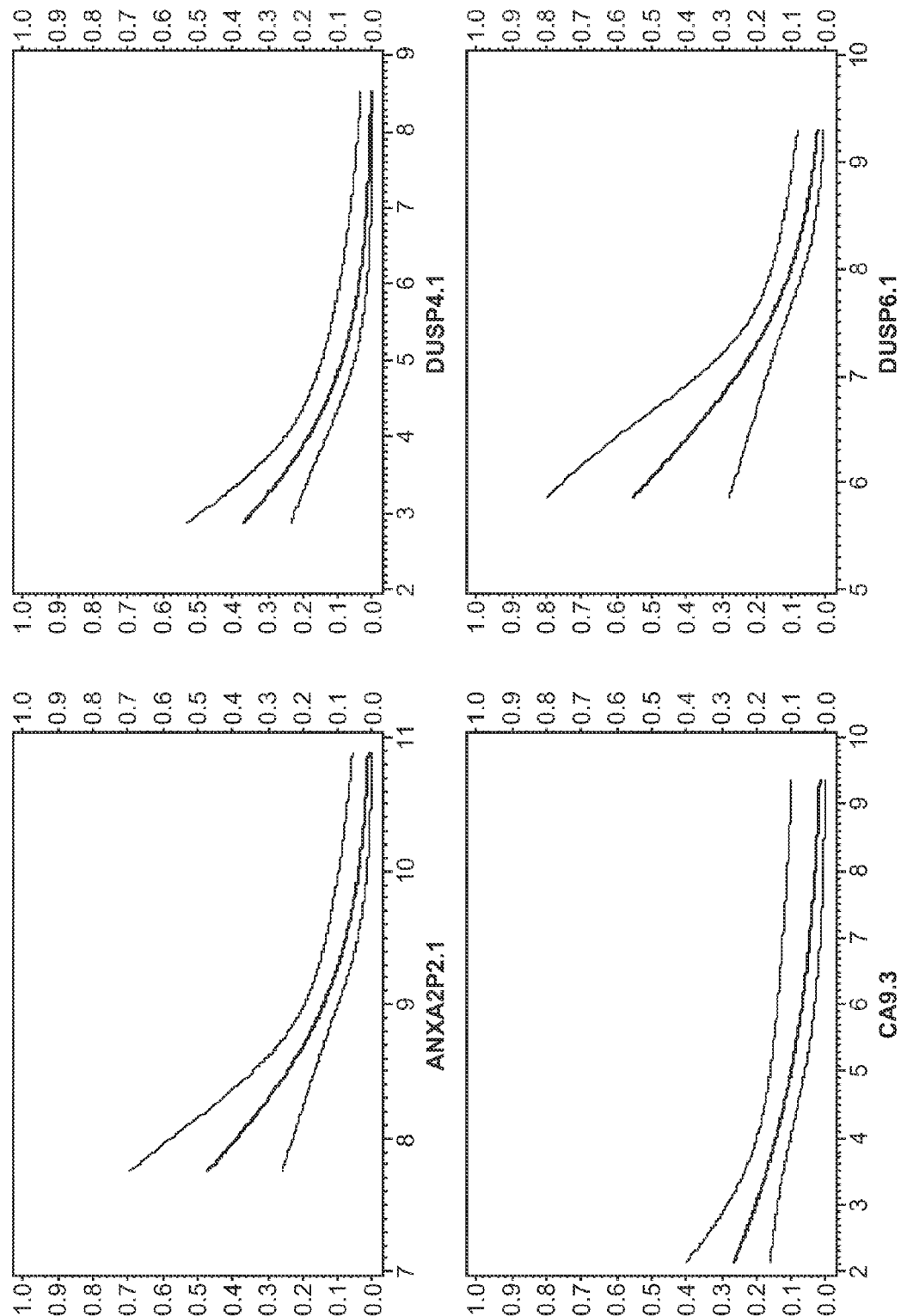
Figure 10B:
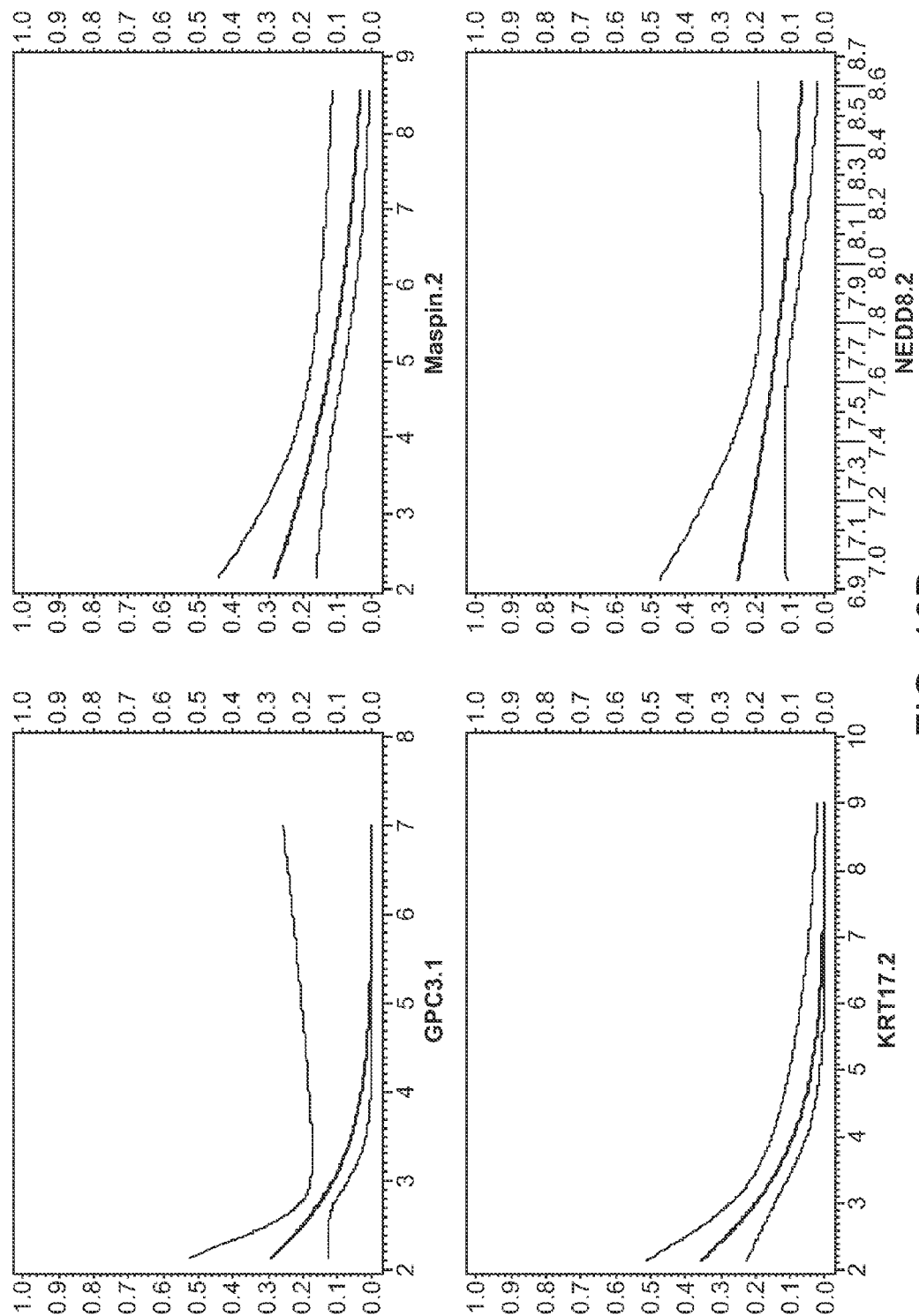
Figure 10C:
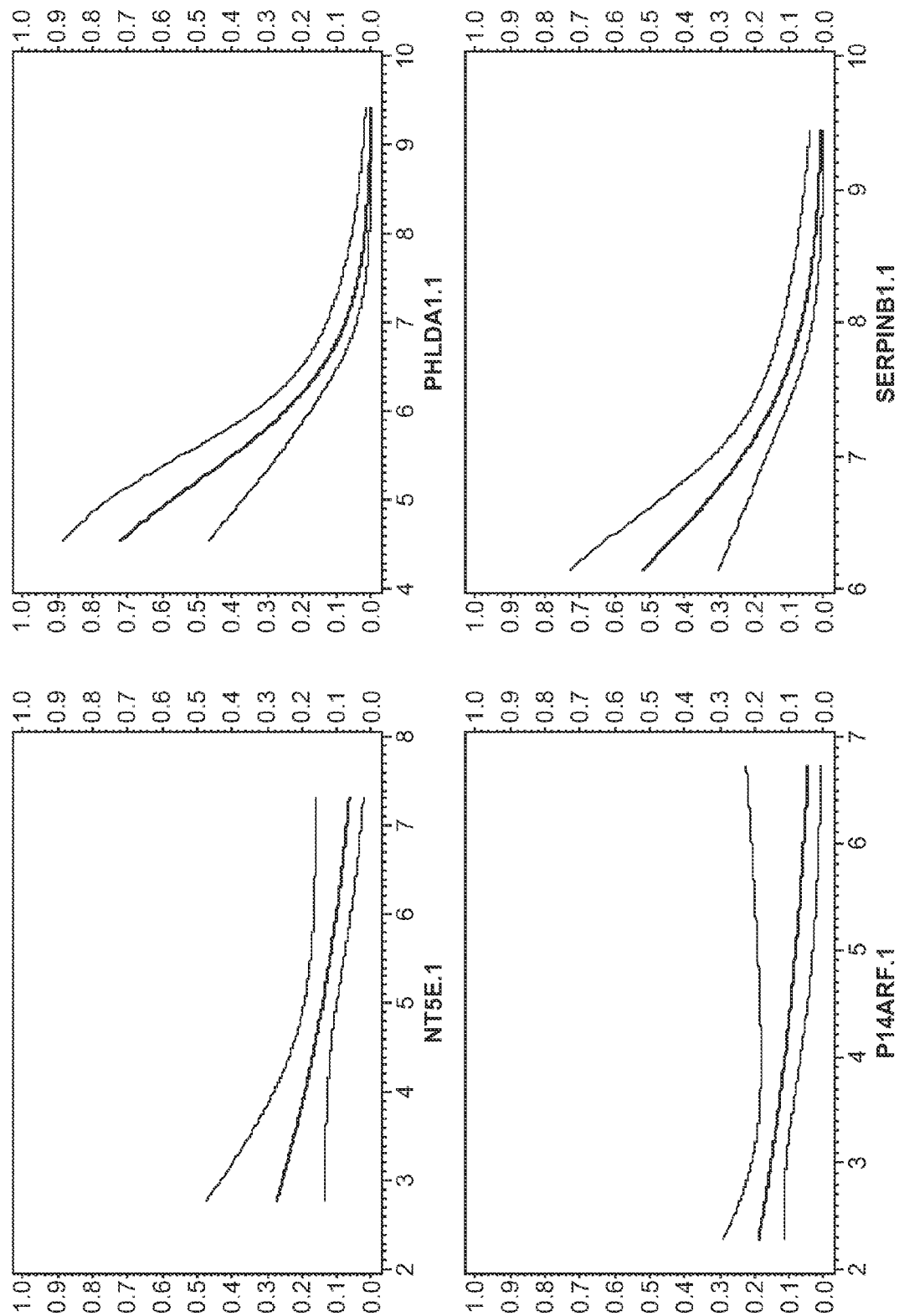
Figure 10D:
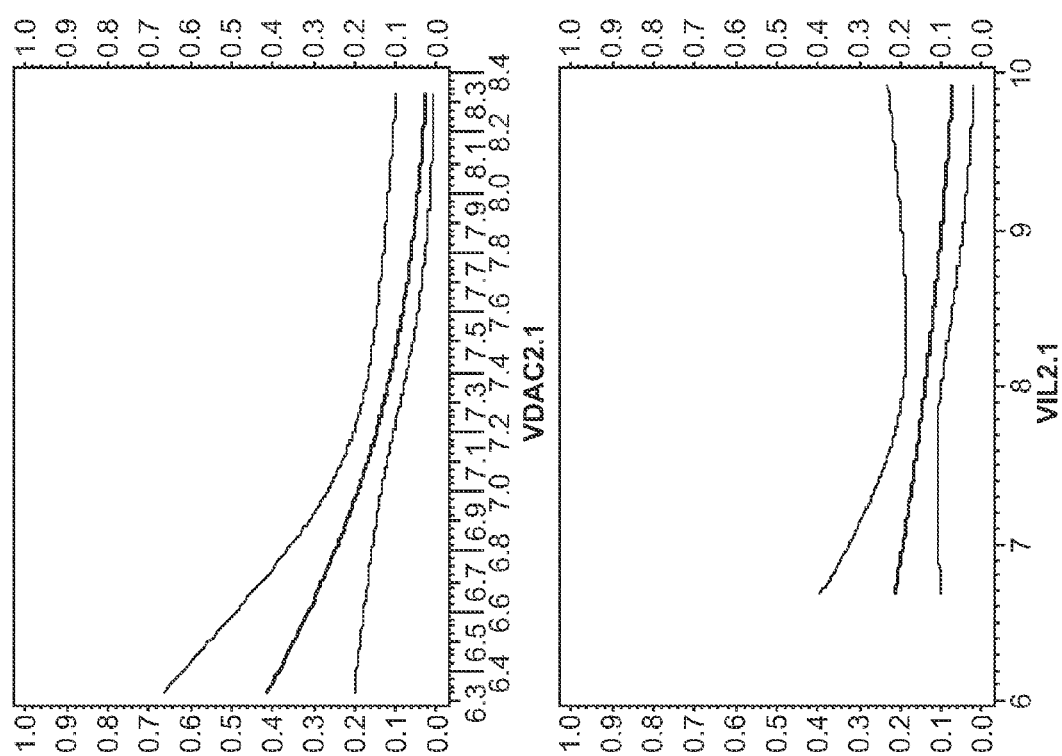

Tables 6A and 6B present tables that show genes for which the normalized expression is correlated (univariate analysis) positively (Table 6A) or negatively (Table 6B) with Overall Response Rate in KRAS-Negative colon cancer patients treated with cetuximab. FIGS. 7A-7C show probability curves that correspond to the data reported in Table 6A; FIGS. 8A-8C show probability curves that correspond to the data reported in Table 6B.

TABLE 6A

| Gene | N | Likelihood Ratio Chi-sq | Likelihood Ratio p-value | Odds Ratio | Wald 95% CI for OR |
|---|---|---|---|---|---|
| EGF | 144 | 9.4751 | 0.0021 | 9.2269 | (2.05, 41.48) |
| ADAM17 | 144 | 6.4427 | 0.0111 | 3.0131 | (1.22, 7.42) |
| PTP4A3 | 143 | 18.1613 | <0.0001 | 2.5136 | (1.59, 3.97) |
| ADAM15 | 144 | 6.1496 | 0.0131 | 2.3126 | (1.17, 4.58) |
| QPRT | 144 | 13.2414 | 0.0003 | 2.2400 | (1.32, 3.79) |
| SATB2 | 144 | 8.3216 | 0.0039 | 2.1358 | (1.21, 3.75) |
| RASSF1 | 144 | 4.7588 | 0.0291 | 2.0634 | (1.04, 4.11) |
| VAV3 | 144 | 9.8051 | 0.0017 | 1.9745 | (1.24, 3.15) |
| CEACAM6 | 144 | 6.0508 | 0.0139 | 1.9605 | (1.10, 3.50) |
| EREG | 144 | 16.2494 | 0.0001 | 1.8354 | (1.32, 2.56) |
| AREG | 144 | 13.6972 | 0.0002 | 1.8113 | (1.28, 2.57) |
| TITF1 | 144 | 5.7005 | 0.0170 | 1.6256 | (1.09, 2.42) |
| SORBS1 | 144 | 4.2346 | 0.0396 | 1.5921 | (1.01, 2.50) |
| C13orf18 | 144 | 4.1806 | 0.0409 | 1.3947 | (1.00, 1.95) |
| CKMT2 | 144 | 6.3844 | 0.0115 | 1.3876 | (1.08, 1.79) |

TABLE 6B

| Gene | N | Likelihood Ratio Chi-sq | Likelihood Ratio p-value | Odds Ratio | Wald 95% CI for OR |
|---|---|---|---|---|---|
| VDAC2 | 144 | 5.3929 | 0.0202 | 0.2638 | (0.08, 0.85) |
| SERPINB1 | 144 | 13.1397 | 0.0003 | 0.2651 | (0.12, 0.59) |
| PHLDA1 | 144 | 18.6782 | <0.0001 | 0.2794 | (0.14, 0.54) |
| ANXA2P2 | 144 | 8.3899 | 0.0038 | 0.3144 | (0.14, 0.72) |
| KRT17 | 144 | 14.1475 | 0.0002 | 0.4140 | (0.24, 0.72) |
| EPHA2 | 144 | 6.8218 | 0.0090 | 0.4954 | (0.28, 0.86) |
| DUSP4 | 144 | 10.6961 | 0.0011 | 0.5045 | (0.32, 0.80) |
| CGA | 144 | 4.6113 | 0.0318 | 0.6350 | (0.40, 1.02) |
| CA9 | 144 | 4.6837 | 0.0304 | 0.7263 | (0.53, 0.99) |
| Maspin | 144 | 4.1275 | 0.0422 | 0.7325 | (0.54, 1.00) |

Example 8

Identification of Gene Markers of Response to an EGFR Inhibitor in KRAS-Negative Colon Cancer Patients (DC Endpoint)

Tables 7A and 7B present tables that show genes for which the normalized expression is correlated (univariate analysis) positively (Table 7A) or negatively (Table 7B) with Disease Control in KRAS-Negative colon cancer patients treated with cetuximab. FIGS. 9A-9E shows probability curves that correspond to the data reported in Table 7A; FIGS. 10A-10D shows probability curves that correspond to the data reported in Table 7B.

TABLE 7A

| Gene | N | Likelihood Ratio Chi-sq | Likelihood Ratio p-value | Odds Ratio | Wald 95% CI for OR |
|---|---|---|---|---|---|
| BTC | 144 | 5.3672 | 0.0205 | 6.1503 | (1.07, 35.43) |
| ATP5E | 144 | 9.0584 | 0.0026 | 3.9235 | (1.55, 9.94) |
| ADAM17 | 144 | 10.1802 | 0.0014 | 3.0447 | (1.49, 6.24) |
| B. Catenin | 144 | 8.5174 | 0.0035 | 2.7911 | (1.36, 5.72) |
| EREG | 144 | 47.5095 | <0.0001 | 2.4680 | (1.82, 3.34) |
| AREG | 144 | 40.8964 | <0.0001 | 2.4514 | (1.77, 3.40) |
| CCNE1 | 144 | 4.0422 | 0.0444 | 2.4162 | (0.95, 6.13) |
| SATB2 | 144 | 16.5332 | <0.0001 | 2.3352 | (1.49, 3.66) |
| EGFR | 144 | 9.6293 | 0.0019 | 2.3261 | (1.30, 4.17) |
| VAV3 | 144 | 21.8405 | <0.0001 | 2.2939 | (1.55, 3.40) |
| TITF1 | 144 | 8.0228 | 0.0046 | 2.2678 | (1.05, 4.88) |
| PTP4A3 | 143 | 17.1734 | <0.0001 | 2.2669 | (1.47, 3.48) |
| CEACAM6 | 144 | 9.2498 | 0.0024 | 1.9068 | (1.22, 2.97) |
| Bclx | 144 | 5.5095 | 0.0189 | 1.8321 | (1.09, 3.09) |
| BRCA1 | 144 | 5.0594 | 0.0245 | 1.7790 | (1.06, 2.98) |
| C13orf18 | 144 | 13.0916 | 0.0003 | 1.6136 | (1.23, 2.13) |
| CKMT2 | 144 | 11.7838 | 0.0006 | 1.5504 | (1.18, 2.04) |
| CDC25B | 144 | 5.0597 | 0.0245 | 1.4596 | (1.04, 2.04) |
| CHN2 | 144 | 5.2658 | 0.0217 | 1.4339 | (1.04, 1.97) |
| QPRT | 144 | 5.7732 | 0.0163 | 1.3853 | (1.05, 1.82) |
| ID1 | 144 | 5.1205 | 0.0236 | 1.3698 | (1.04, 1.81) |
| SLC26A3 | 144 | 11.8812 | 0.0006 | 1.3611 | (1.13, 1.64) |

TABLE 7B

| Gene | N | Likelihood Ratio Chi-sq | Likelihood Ratio p-value | Odds Ratio | Wald 95% CI for OR |
|---|---|---|---|---|---|
| NEDD8 | 144 | 7.4988 | 0.0062 | 0.2196 | (0.07, 0.67) |
| VDAC2 | 144 | 8.6138 | 0.0033 | 0.2504 | (0.10, 0.65) |
| SERPINB1 | 144 | 16.9744 | <0.0001 | 0.3055 | (0.17, 0.56) |
| DUSP6 | 144 | 13.8060 | 0.0002 | 0.3191 | (0.17, 0.61) |
| GPC3 | 144 | 6.6733 | 0.0098 | 0.3497 | (0.13, 0.94) |
| ANXA2P2 | 144 | 7.6631 | 0.0056 | 0.4116 | (0.21, 0.79) |
| NT5E | 144 | 16.6993 | <0.0001 | 0.4617 | (0.31, 0.69) |
| DUSP4 | 144 | 17.4132 | <0.0001 | 0.5194 | (0.37, 0.72) |
| VIL2 | 144 | 4.1446 | 0.0418 | 0.5608 | (0.32, 0.99) |
| PHLDA1 | 144 | 7.4036 | 0.0065 | 0.5656 | (0.37, 0.86) |
| P14ARF | 144 | 7.2519 | 0.0071 | 0.6121 | (0.42, 0.89) |
| KRT17 | 144 | 8.3225 | 0.0039 | 0.6501 | (0.48, 0.88) |
| CA9 | 144 | 6.8230 | 0.0090 | 0.7422 | (0.59, 0.93) |
| Maspin | 144 | 5.3058 | 0.0213 | 0.7451 | (0.58, 0.96) |

Example 9

Multigene Models of Response to an EGFR Inhibitor in KRAS-Negative Colon Cancer Patients (ORR Endpoint)

Table 8 shows genes and gene combinations, the expression levels of which can be combined in multigene models to correlate with Overall Response Rate in KRAS-Negative colon cancer patients treated with Cetuximab. Note: "aregereg" is the average of the normalized AREG value and the normalized EREG value.

TABLE 8

(ORR)

| | # of Models | % of Models | Mean AUC | SD AUC | Median AUC |
|---|---|---|---|---|---|
| 1-gene | | | | | |
| PTP4A3 | 40 | 71% | 0.69 | 0.07 | 0.68 |
| EREG | 8 | 14% | 0.62 | 0.08 | 0.64 |

TABLE 8-continued

| (ORR) | | | | | |
|---|---|---|---|---|---|
| | # of Models | % of Models | Mean AUC | SD AUC | Median AUC |
| PHLDA1 | 5 | 9% | 0.65 | 0.11 | 0.65 |
| aregereg | 3 | 5% | 0.70 | 0.10 | 0.70 |
| Total 2-gene | 56 | 100% | 0.66 | 0.09 | 0.67 |
| PHLDA1 PTP4A3 | 45 | 46% | 0.77 | 0.08 | 0.78 |
| KRT17 PTP4A3 | 13 | 13% | 0.72 | 0.09 | 0.76 |
| EREG PHLDA1 | 10 | 10% | 0.77 | 0.06 | 0.78 |
| aregereg PHLDA1 | 9 | 9% | 0.76 | 0.06 | 0.77 |
| EREG KRT17 | 6 | 6% | 0.75 | 0.08 | 0.74 |
| aregereg KRT17 | 5 | 5% | 0.68 | 0.16 | 0.73 |
| AREG PHLDA1 | 3 | 3% | 0.76 | 0.01 | 0.76 |
| KRT17 SERPINB1 | 2 | 2% | 0.58 | 0.04 | 0.58 |
| CEACAM6 PTP4A3 | 1 | 1% | 0.58 | — | 0.58 |
| EREG PTP4A3 | 1 | 1% | 0.70 | — | 0.70 |
| KRT17 SORBS1 | 1 | 1% | 0.60 | — | 0.60 |
| PHLDA1 SORBS1 | 1 | 1% | 0.53 | — | 0.53 |
| SATB2 SERPINB1 | 1 | 1% | 0.52 | — | 0.52 |
| Total 3-gene | 98 | 100% | 0.67 | 0.07 | 0.68 |
| AREG PHLDA1 PTP4A3 | 7 | 13% | 0.80 | 0.06 | 0.80 |
| aregereg KRT17 PHLDA1 | 7 | 13% | 0.85 | 0.06 | 0.86 |
| aregereg PHLDA1 PTP4A3 | 5 | 10% | 0.79 | 0.07 | 0.77 |
| EREG PHLDA1 SORBS1 | 5 | 10% | 0.69 | 0.06 | 0.71 |
| EGFR PHLDA1 PTP4A3 | 4 | 8% | 0.59 | 0.09 | 0.62 |
| KRT17 PTP4A3 SORBS1 | 4 | 8% | 0.62 | 0.12 | 0.58 |
| aregereg KRT17 PTP4A3 | 3 | 6% | 0.80 | 0.06 | 0.79 |
| EREG KRT17 PHLDA1 | 3 | 6% | 0.69 | 0.14 | 0.70 |
| PHLDA1 PTP4A3 SORBS1 | 3 | 6% | 0.73 | 0.12 | 0.67 |
| EGFR EREG PHLDA1 | 2 | 4% | 0.66 | 0.04 | 0.66 |
| EREG PHLDA1 SATB2 | 2 | 4% | 0.62 | 0.01 | 0.62 |
| AREG KRT17 PHLDA1 | 1 | 2% | 0.63 | — | 0.63 |
| CEACAM6 PHLDA1 PTP4A3 | 1 | 2% | 0.73 | — | 0.73 |
| EGFR EPHA2 EREG | 1 | 2% | 0.65 | — | 0.65 |
| EREG KRT17 SLC26A3 | 1 | 2% | 0.47 | — | 0.47 |
| EREG PHLDA1 PTP4A3 | 1 | 2% | 0.71 | — | 0.71 |
| EREG PHLDA1 QPRT | 1 | 2% | 0.58 | — | 0.58 |
| PHLDA1 PTP4A3 SATB2 | 1 | 2% | 0.66 | — | 0.66 |
| Total 4-gene | 52 | 100% | 0.68 | 0.08 | 0.68 |
| EREG KRT17 PHLDA1 SORBS1 | 6 | 19% | 0.76 | 0.10 | 0.74 |
| AREG KRT17 PHLDA1 PTP4A3 | 2 | 6% | 0.92 | 0.05 | 0.92 |
| aregereg KRT17 PHLDA1 PTP4A3 | 2 | 6% | 0.80 | 0.03 | 0.80 |
| aregereg PHLDA1 PTP4A3 SATB2 | 2 | 6% | 0.72 | 0.06 | 0.72 |
| aregereg PHLDA1 PTP4A3 SORBS1 | 2 | 6% | 0.84 | 0.12 | 0.84 |
| DUSP6 EREG KRT17 SORBS1 | 2 | 6% | 0.60 | 0.05 | 0.60 |
| AREG EGFR EPHA2 PHLDA1 | 1 | 3% | 0.74 | — | 0.74 |
| aregereg CEACAM6 KRT17 SORBS1 | 1 | 3% | 0.79 | — | 0.79 |
| aregereg EGFR KRT17 PHLDA1 | 1 | 3% | 0.78 | — | 0.78 |
| aregereg KRT17 PHLDA1 SORBS1 | 1 | 3% | 0.80 | — | 0.80 |
| aregereg KRT17 PTP4A3 SORBS1 | 1 | 3% | 0.84 | — | 0.84 |
| CEACAM6 EREG PHLDA1 SORBS1 | 1 | 3% | 0.81 | — | 0.81 |
| CEACAM6 KRT17 PHLDA1 PTP4A3 | 1 | 3% | 0.73 | — | 0.73 |
| CEACAM6 KRT17 PTP4A3 SORBS1 | 1 | 3% | 0.78 | — | 0.78 |
| EGFR EPHA2 PHLDA1 PTP4A3 | 1 | 3% | 0.63 | — | 0.63 |
| EGFR EREG KRT17 PHLDA1 | 1 | 3% | 0.74 | — | 0.74 |
| EGFR KRT17 PHLDA1 PTP4A3 | 1 | 3% | 0.69 | — | 0.69 |
| EREG KRT17 PTP4A3 SORBS1 | 1 | 3% | 0.57 | — | 0.57 |
| EREG LAMA3 PHLDA1 QPRT | 1 | 3% | 0.57 | — | 0.57 |
| EREG PHLDA1 PTP4A3 QPRT | 1 | 3% | 0.66 | — | 0.66 |
| KRT17 PHLDA1 PTP4A3 SORBS1 | 1 | 3% | 0.85 | — | 0.85 |
| KRT17 PTP4A3 SORBS1 VDAC2 | 1 | 3% | 0.77 | — | 0.77 |
| Total 5-gene | 32 | 100% | 0.74 | 0.07 | 0.74 |
| AREG EGFR KRT17 PHLDA1 PTP4A3 | 1 | 11% | 0.79 | — | 0.79 |
| AREG KRT17 PHLDA1 PTP4A3 SORBS1 | 2 | 22% | 0.87 | 0.10 | 0.87 |
| aregereg CEACAM6 KRT17 PHLDA1 | 2 | 22% | 0.76 | 0.10 | 0.76 |
| aregereg EGFR KRT17 PHLDA1 PTP4A3 | 1 | 11% | 0.80 | — | 0.80 |

TABLE 8-continued (ORR)

| | # of Models | % of Models | Mean AUC | SD AUC | Median AUC |
|---|---|---|---|---|---|
| aregereg EPHA2 KRT17 PTP4A3 SORBS1 | 1 | 11% | 0.81 | — | 0.81 |
| CEACAM6 KRT17 PHLDA1 PTP4A3 | 1 | 11% | 0.69 | — | 0.69 |
| EREG KRT17 PHLDA1 PLAUR SORBS1 | 1 | 11% | 0.72 | — | 0.72 |
| Total | 9 | 100% | 0.78 | 0.10 | 0.78 |
| 6-gene | | | | | |
| AREG EPHA2 KRT17 LAMC2 PHLDA1 | 1 | 100% | 0.74 | — | — |
| 7-gene | | | | | |
| ANXA1 BRCA1 CHN2 PHLDA1 PTP4A3 | 1 | 50% | 0.44 | — | — |
| CEACAM6 KRT17 LAMA3 PHLDA1 PTP4A3 | 1 | 50% | 0.76 | — | — |
| Total | 2 | 100% | 0.60 | | |

Example 10

Multigene Models of Response to an EGFR Inhibitor in KRAS-Negative Colon Cancer Patients (DC Endpoint)

Table 9 presents a table that shows genes and gene combinations, the expression levels of which can be combined in multigene models to correlate with Disease Control in KRAS-Negative colon cancer patients treated with Cetuximab. Note: "aregereg" is the average of the normalized AREG value and the normalized EREG value.

TABLE 9

(DC)

| | # of Models | % of Models | Mean AUC | SD AUC | Median AUC |
|---|---|---|---|---|---|
| 1-Gene Models | | | | | |
| Aregereg | 96 | 53% | 0.81 | 0.08 | 0.82 |
| EREG | 84 | 47% | 0.8 | 0.07 | 0.81 |
| Total | 180 | 100% | 0.8 | 0.08 | 0.81 |
| 2-Gene Models | | | | | |
| SLC26A3 aregereg | 12 | 29% | 0.8 | 0.05 | 0.81 |
| DUSP6 EREG | 10 | 24% | 0.78 | 0.08 | 0.76 |
| DUSP6 aregereg | 8 | 19% | 0.84 | 0.05 | 0.84 |
| EREG SLC26A3 | 5 | 12% | 0.84 | 0.04 | 0.83 |
| VIL2 aregereg | 2 | 5% | 0.83 | 0.07 | 0.83 |
| DR5 aregereg | 1 | 2% | 0.78 | — | 0.78 |
| EPHA2 aregereg | 1 | 2% | 0.71 | — | 0.71 |
| EREG NT5E | 1 | 2% | 0.72 | — | 0.72 |
| KRT17 aregereg | 1 | 2% | 0.84 | — | 0.84 |
| SATB2 aregereg | 1 | 2% | 0.63 | — | 0.63 |
| Total | 42 | 100% | 0.78 | 0.06 | 0.77 |
| 3-Gene Models | | | | | |
| DUSP6 EREG SLC26A3 | 7 | 33% | 0.8 | 0.06 | 0.82 |
| DUSP6 SLC26A3 aregereg | 6 | 29% | 0.81 | 0.07 | 0.83 |
| CA9 EREG NT5E | 1 | 5% | 0.59 | — | 0.59 |
| CLTC DUSP6 aregereg | 1 | 5% | 0.68 | — | 0.68 |
| DR5 SLC26A3 aregereg | 1 | 5% | 0.79 | — | 0.79 |
| DUSP6 VIL2 aregereg | 1 | 5% | 0.82 | — | 0.82 |
| EPHA2 EREG SLC26A3 | 1 | 5% | 0.65 | — | 0.65 |
| EREG SLC26A3 VIL2 | 1 | 5% | 0.75 | — | 0.75 |
| KRT17 SLC26A3 aregereg | 1 | 5% | 0.8 | — | 0.8 |
| SLC26A3 VIL2 aregereg | 1 | 5% | 0.95 | — | 0.95 |
| Total | 21 | 100% | 0.76 | 0.07 | 0.77 |
| 4-Gene Models | | | | | |
| aregereg DR5 DUSP6 SLC26A3 | 1 | 20% | 0.93 | — | — |
| AMACR1 aregereg DUSP6 SATB2 | 1 | 20% | 0.69 | — | — |
| aregereg CLTC DUSP6 SLC26A3 | 1 | 20% | 0.84 | — | — |
| aregereg DUSP6 KRT17 SLC26A3 | 1 | 20% | 0.76 | — | — |
| EGFR EREG SLC26A3 VIL2 | 1 | 20% | 0.92 | — | — |
| 5-Gene Model | | | | | |
| DUSP6 EREG QPRT SLC26A3 VIL2 | | | | | |
| Total | 1 | 100% | 0.74 | — | — |

Example 11

Observed Versus Predicted ORR Using a 4-Gene Logistic Model AREG, EREG, SLC26A3 AND DUSP6

Table 10 presents a table that compares observed patient response (DC endpoint) to treatment with cetuximab and response predicted using a 4-gene model based on expression levels of AREG, EREG, SLC26A3 and DUSP6. The threshold for the 4-gene model was determined by identifying the cutpoint that yielded the highest number of true negatives plus true positives on the DC endpoint. Table 10 illustrates the number of patients who would be classified as responders versus non-responders using the 4-gene model. The percentages are row percents, summarizing the number of patients with observed DC status given the predicted DC status from the 4-gene model.

TABLE 10

|  |  | Observed DC Status | | Predicted DC Total |
|---|---|---|---|---|
|  |  | No | Yes |  |
| Predicted DC Status using 4-gene logistic model | No | 44 (36, 50)<br>73% (60%, 84%) | 16 (10, 24)<br>27% (16%, 40%) | 60 (42%) |
|  | Yes | 13 (8, 21)<br>15% (9%, 25%) | 71 (63, 77)<br>85% (75%, 92%) | 84 (58%) |
|  | Observed DC Total | 57 (40%) | 87 (60%) | 144 |

Table 11 presents a table that compares the progression free survival time for patients for all KRAS-positive patients, for all KRAS-negative patients, for patients predicted by the four-gene classifier as having a high likelihood of response to treatment with an EGFR inhibitor and for patients predicted by the four-gene classifier as having a low likelihood of response to treatment with an EGFR inhibitor. The four gene classifier identifies a subset of KRAS-Negative patients that have a higher likelihood of response to treatment with an EGFR inhibitor (longer progression free survival (PFS) than the unclassified KRAS-Negative patients. The four gene classifier also identifies a subset of KRAS-Negative patients that have a lower likelihood of response (shorter progression free survival) than the unclassified KRAS-Negative patients; in these patients, PFS is similar to that seen in KRAS-Positive patients, who are generally resistant to treatment.

TABLE 11

|  | No. of Patients | Median Survival (95% CI) |
|---|---|---|
| KRAS-Positive | 82 | 41 (40, 51) |
| KRAS-Negative with Low | 60 | 40 (38, 46) |

TABLE 11-continued

|  | No. of Patients | Median Survival (95% CI) |
|---|---|---|
| Predicted Likelihood of Response |  |  |
| KRAS-Negative with High Predicted Likelihood of Response | 84 | 163 (126, 180) |
| All KRAS-Negative | 144 | 103 (78, 126) |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for predicting a likelihood that a human patient with an epidermal growth factor receptor (EGFR)—expressing colorectal cancer will exhibit a beneficial response to an EGFR inhibitor comprising:
   (a) measuring, in a tumor sample obtained from the patient, a level of an RNA transcript, or its expression product, for each of solute carrier family 26, member 3 (SLC26A3), amphiregulin (AREG), epiregulin (EREG) and dual specificity phosphatase 6 (DUSP6),
   (b) normalizing the level of the RNA transcript, or its expression product, for each of SLC26A3, AREG, EREG, and DUSP6 to obtain a normalized expression level for each of SLC26A3, AREG, EREG, and DUSP6; and
   (c) using the normalized expression level to determine the likelihood that the patient will exhibit a beneficial response to an EGFR inhibitor,
   wherein the normalized expression levels of SLC26A3, AREG, and EREG are positively correlated with the likelihood that the patient will exhibit a beneficial response to the EGFR inhibitor, and wherein the normalized expression level of DUSP6 is negatively correlated with the likelihood that the patient will exhibit a beneficial response to the EGFR inhibitor.

2. The method of claim 1, wherein the tumor sample is obtained from a tissue biopsy.

3. The method of claim 1, wherein the EGFR inhibitor is an antibody specific for EGFR.

4. The method of claim 3, wherein the EGFR inhibitor is cetuximab.

5. The method of claim 1, wherein the EGFR inhibitor is a small molecule.

6. The method of claim 5, wherein the small molecule is an EGFR-selective tyrosine kinase inhibitor.

7. The method of claim 1, wherein the normalized expression level is determined relative to an expression level of at least one reference gene.

8. The method of claim 1, wherein the levels of the SLC26A3, AREG, EREG, and DUSP6 RNA transcripts are measured.

9. The method of claim 8, wherein the levels of the SLC26A3, AREG, EREG, and DUSP6 RNA transcripts are measured by reverse transcriptase polymerase chain reaction (RT-PCR).

10. The method of claim 1, wherein beneficial response is expressed in terms of Overall Response Rate (ORR) or Disease Control (DC).

11. The method of claim 1, wherein the normalized expression level is weighted by its contribution to response to the EGFR inhibitor.

12. The method of claim 1, further comprising the step of creating a report summarizing said prediction.

* * * * *